(12) United States Patent
McChesney et al.

(10) Patent No.: US 10,064,823 B2
(45) Date of Patent: Sep. 4, 2018

(54) NANOPARTICULATE COMPOSITIONS FOR TARGETED DELIVERY OF ACID LABILE, LIPOPHILIC PRODRUGS OF CANCER CHEMOTHERAPEUTICS AND THEIR PREPARATION

(71) Applicant: Arbor Therapeutics, LLC, Etta, MS (US)

(72) Inventors: James D. McChesney, Etta, MS (US); Igor Nikoulin, San Diego, CA (US); Steve J. Bannister, Tampa, FL (US); Douglas L. Rodenburg, Thaxton, MS (US)

(73) Assignee: Veiled Therapeutics LLC, Etta, MS (US)

( * ) Notice: Subject to any disclaimer, the term of this patent is extended or adjusted under 35 U.S.C. 154(b) by 0 days.

(21) Appl. No.: 15/243,659

(22) Filed: Aug. 22, 2016

(65) Prior Publication Data
US 2017/0042815 A1    Feb. 16, 2017

Related U.S. Application Data

(62) Division of application No. 14/485,713, filed on Sep. 13, 2014, now Pat. No. 9,468,603.

(60) Provisional application No. 61/877,521, filed on Sep. 13, 2013.

(51) Int. Cl.
| | |
|---|---|
| *A61K 9/12* | (2006.01) |
| *A61K 31/337* | (2006.01) |
| *A61K 31/365* | (2006.01) |
| *A61K 31/366* | (2006.01) |
| *A61K 31/427* | (2006.01) |
| *A61K 31/4745* | (2006.01) |
| *A61K 31/475* | (2006.01) |
| *A61K 31/5685* | (2006.01) |
| *A61K 31/575* | (2006.01) |
| *A61K 31/704* | (2006.01) |
| *A61K 31/7056* | (2006.01) |
| *A61K 45/06* | (2006.01) |
| *A61K 9/127* | (2006.01) |
| *A61K 31/7068* | (2006.01) |
| *A61K 31/7076* | (2006.01) |
| *A61K 9/00* | (2006.01) |
| *A61K 9/51* | (2006.01) |
| *A61K 31/357* | (2006.01) |
| *A61K 47/54* | (2017.01) |

(52) U.S. Cl.
CPC .......... *A61K 9/1275* (2013.01); *A61K 9/0019* (2013.01); *A61K 9/5123* (2013.01); *A61K 31/337* (2013.01); *A61K 31/357* (2013.01); *A61K 31/365* (2013.01); *A61K 31/366* (2013.01); *A61K 31/427* (2013.01); *A61K 31/475* (2013.01); *A61K 31/4745* (2013.01); *A61K 31/5685* (2013.01); *A61K 31/575* (2013.01); *A61K 31/704* (2013.01); *A61K 31/7056* (2013.01); *A61K 31/7068* (2013.01); *A61K 31/7076* (2013.01); *A61K 45/06* (2013.01); *A61K 47/545* (2017.08)

(58) Field of Classification Search
CPC .............. A61K 31/365; A61K 31/4745; A61K 31/475; A61K 31/5685; A61K 31/704; A61K 31/7056; A61K 31/7068; A61K 31/7076; A61K 45/06; A61K 9/1275; A61K 31/337; A61K 31/357; A61K 31/366; A61K 31/427; A61K 31/575; A61K 47/48061
See application file for complete search history.

(56) References Cited

PUBLICATIONS

Harisa et al (Saudi Pharmaceutical Journal, 2014, vol. 22, pp. 504-515).*
Wang et al (Cancer Letters, 2013, vol. 331, pp. 139-146).*
J.A. Moura et al, Novel Formulation of a Methotrexate Derivative with a Lipid Nanoemulsion, International Journal of Nanomedicine, 2011; 6, pp. 2285-2295.
J-H. Yang et al., In Vitro Anticancer Activity of Paclitaxel Incorporated in Low-Melting SOlid Lipid Nanoparticles, J. Kor. Pharm. Sci, vol. 39, No. 3, 201-205, 2009.

* cited by examiner

*Primary Examiner* — Mark V Stevens
(74) *Attorney, Agent, or Firm* — Hamilton DeSanctis & Cha, LLP; Sam L. Nguyen

(57) ABSTRACT

In one embodiment, the present application discloses synthetic LDL nanoparticles comprising mixtures of components selected from the group consisting of phospholipids, triglycerides, cholesterol ester and free cholesterol; optionally further comprising an agent selected from the group consisting of natural antioxidants, ubiquinol and vitamin E, and methods for preparing the synthetic nanoparticles. The disclosed synthetic LDL nanoparticles are capable of selectively delivering lipophilic drugs and prodrugs to cellular targets expressing LDL receptors after intra venous injection.

11 Claims, 45 Drawing Sheets

Figure 1: Particle size reaches the 55-60 nm plateau after 40 discrete passes.
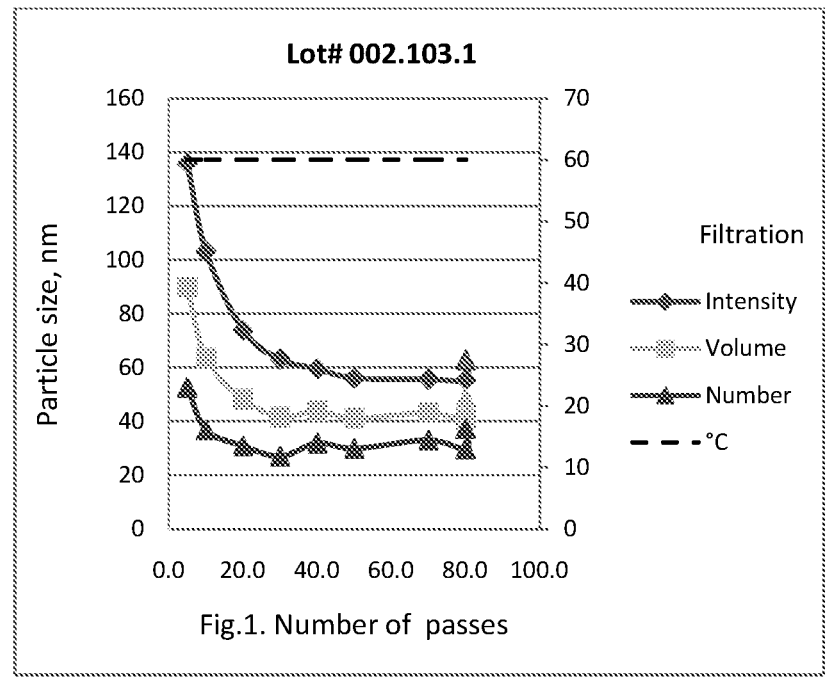
Figure 2: Particle size and stability of drug free formulation.
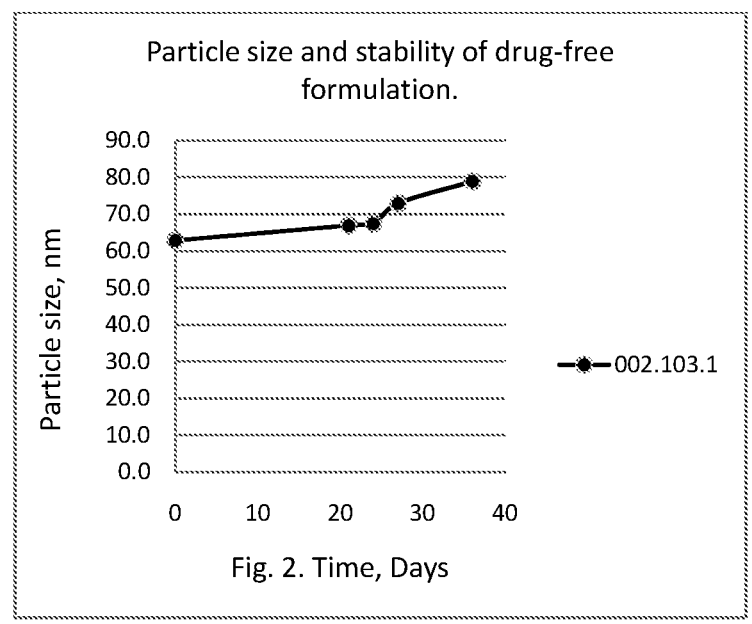

Figure 3: Cooling conditions allowed further decreasing of the particle size to 43 nm
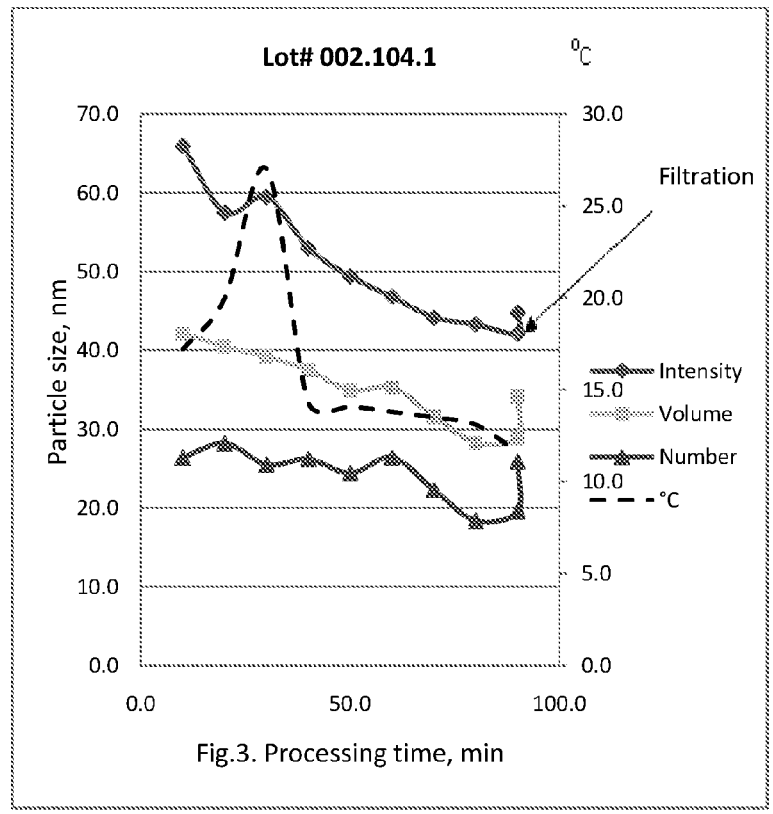
Figure 4: Representative graph showing a particle size analysis of drug-free formulation.
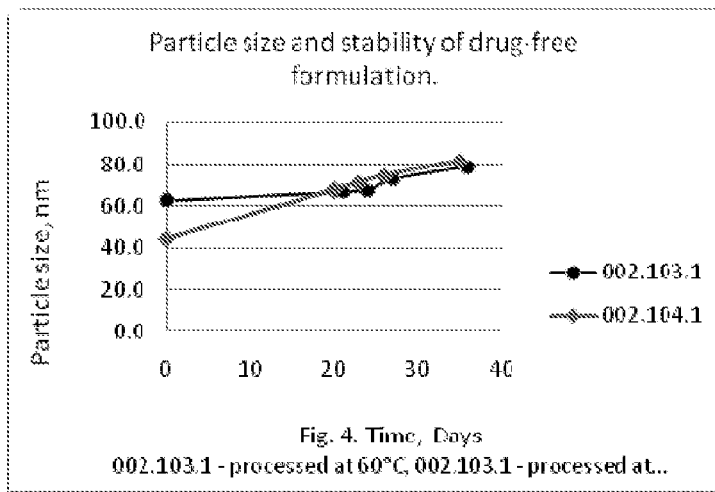

Figure 5: Representative graph showing particle size reaches the plateau or resistance.
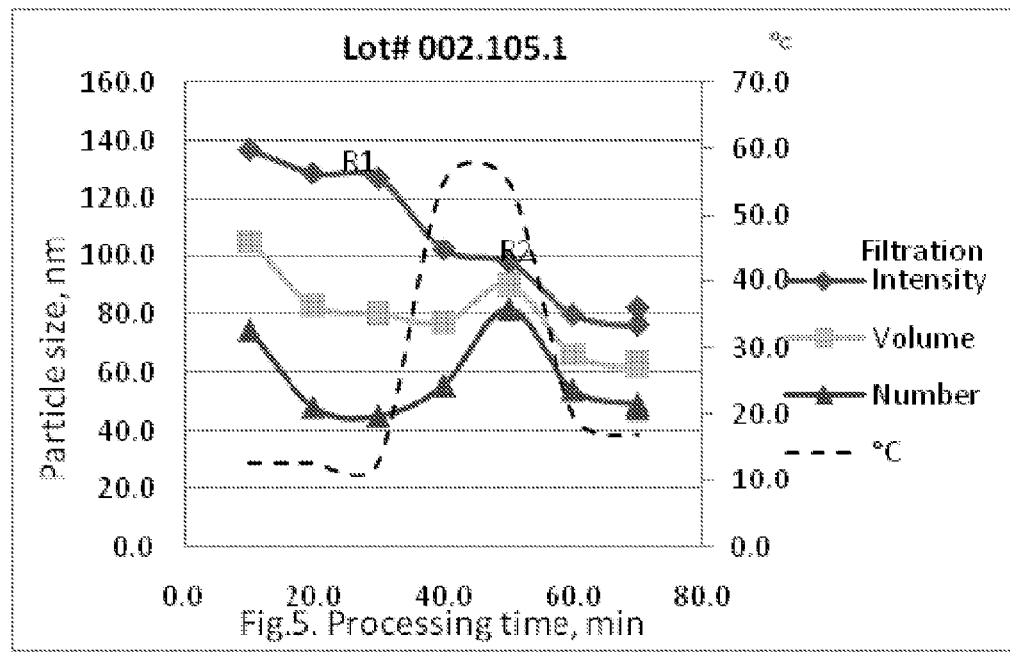
Figure 6: Representative graph showing different particle size and stability over time.
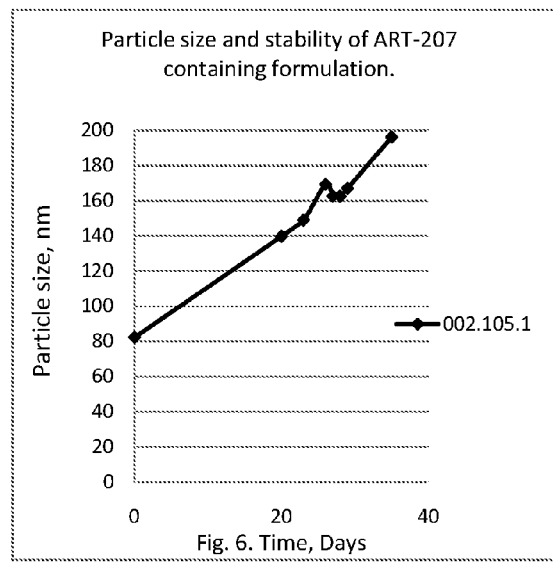

Figure 7: Representative graph showing particle size at different temperatures.
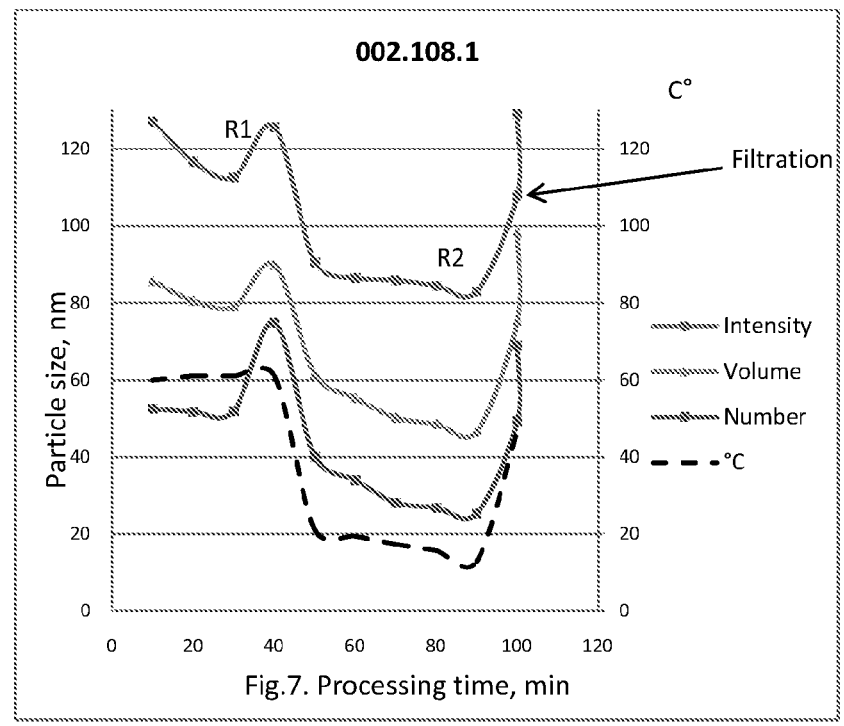
Figure 8: Representative graph showing particle size increase over time.
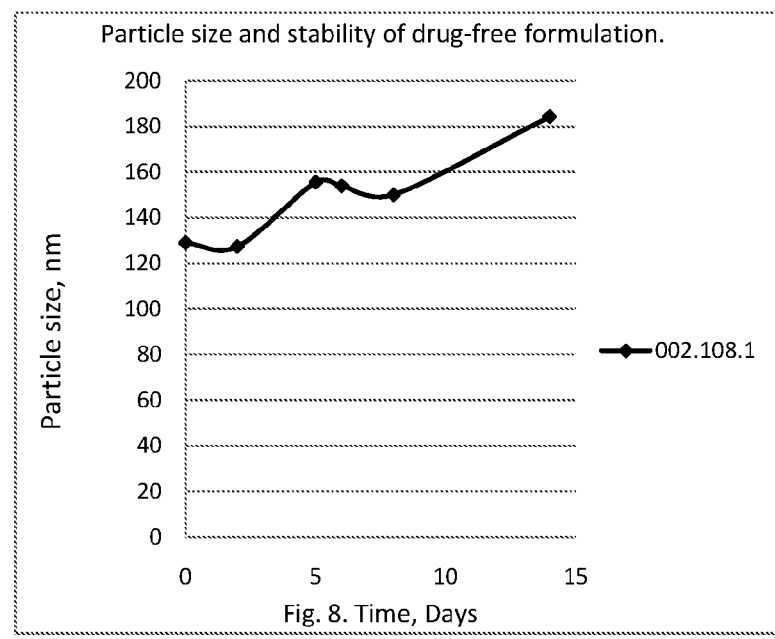

Figure 9: Representative graph showing change in particle size over time and temperature.
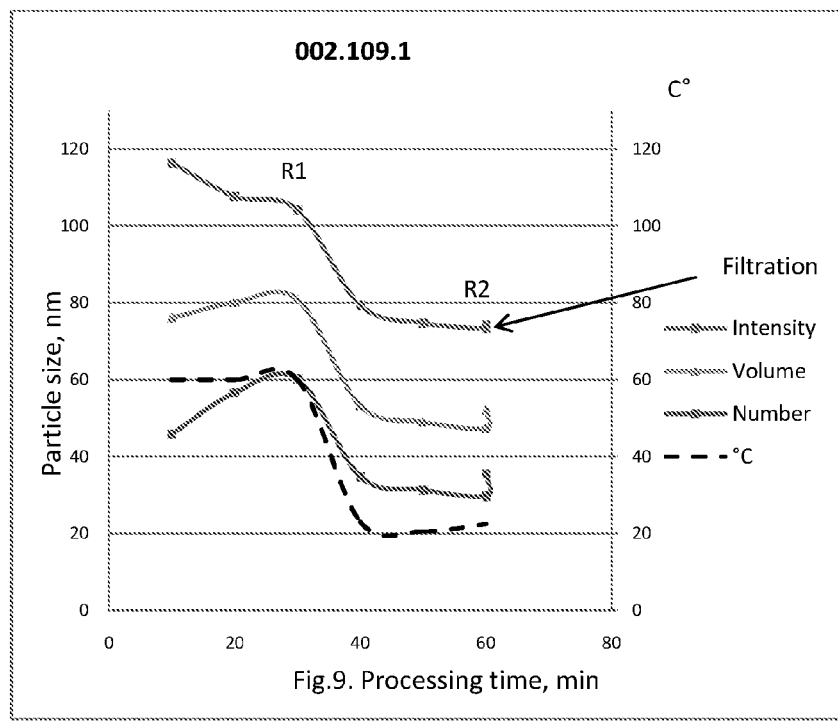
Figure 10: Representative graph showing stability of ART-207 formulation over time.
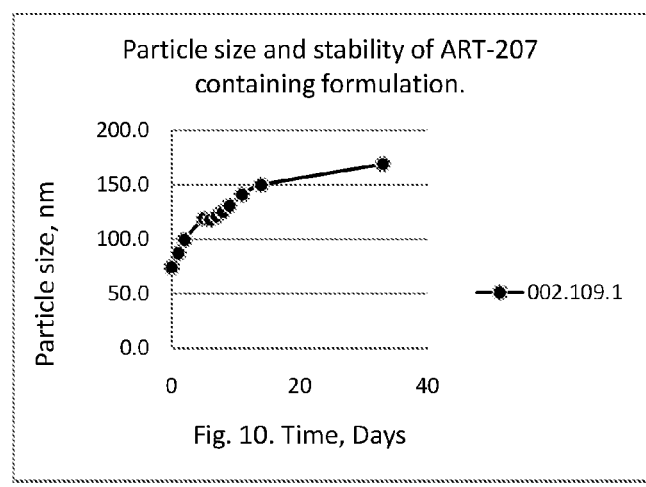

Figure 11: Representative graph showing relative particle size over processing time and temperatures
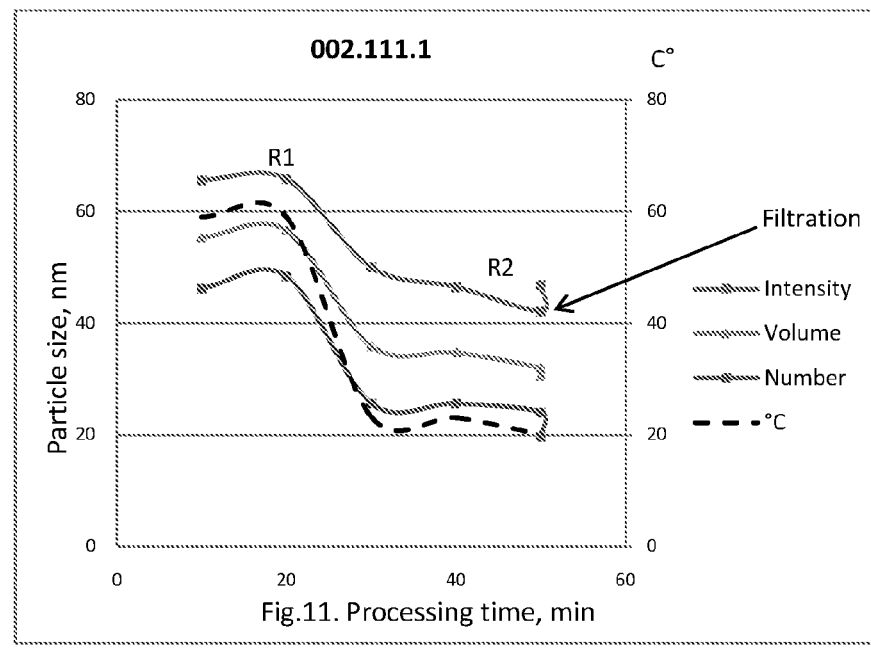
Figure 12: Representative graph showing particle size and stability over time
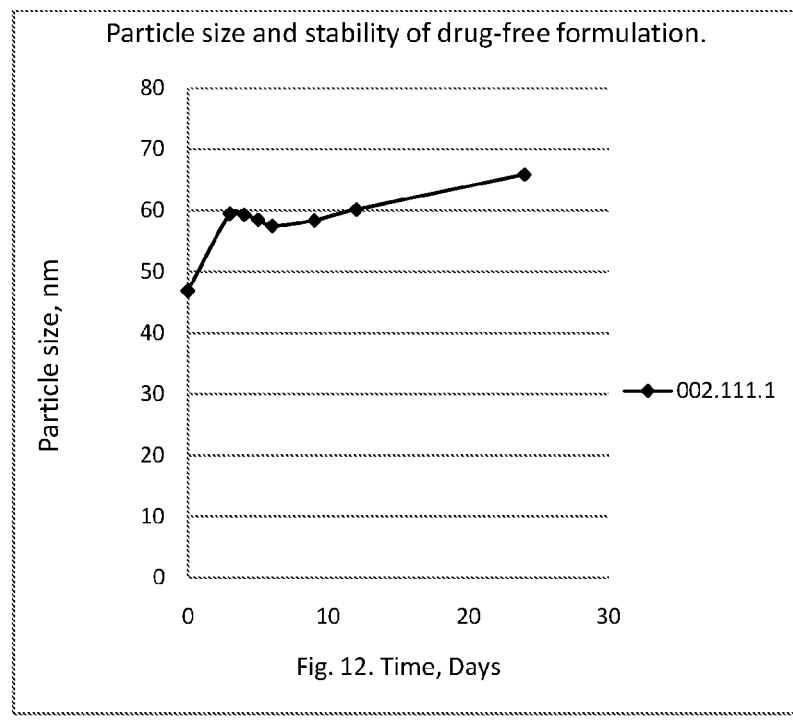

Figure 13: Representative graph showing particle size over time and temperature
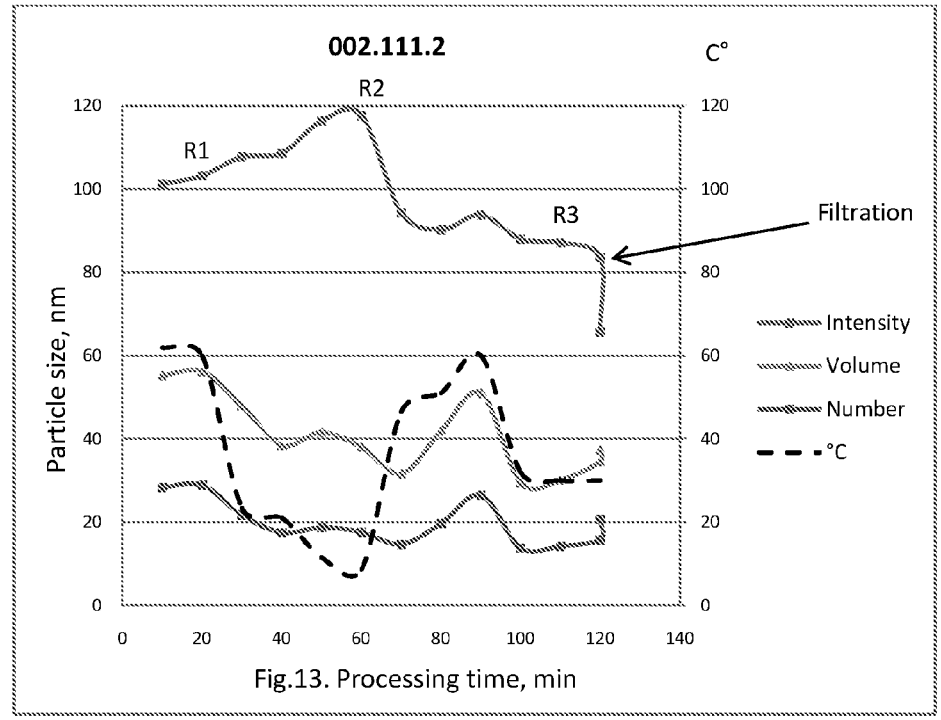
Figure 14: Representative graph showing particle size and stability of ART-207 over time.
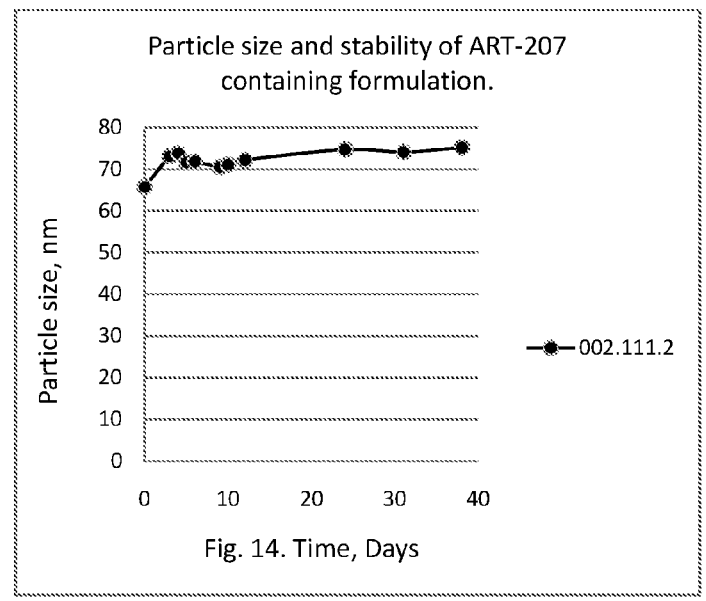

Figure 15: Representative graph showing particle size over time and temperature
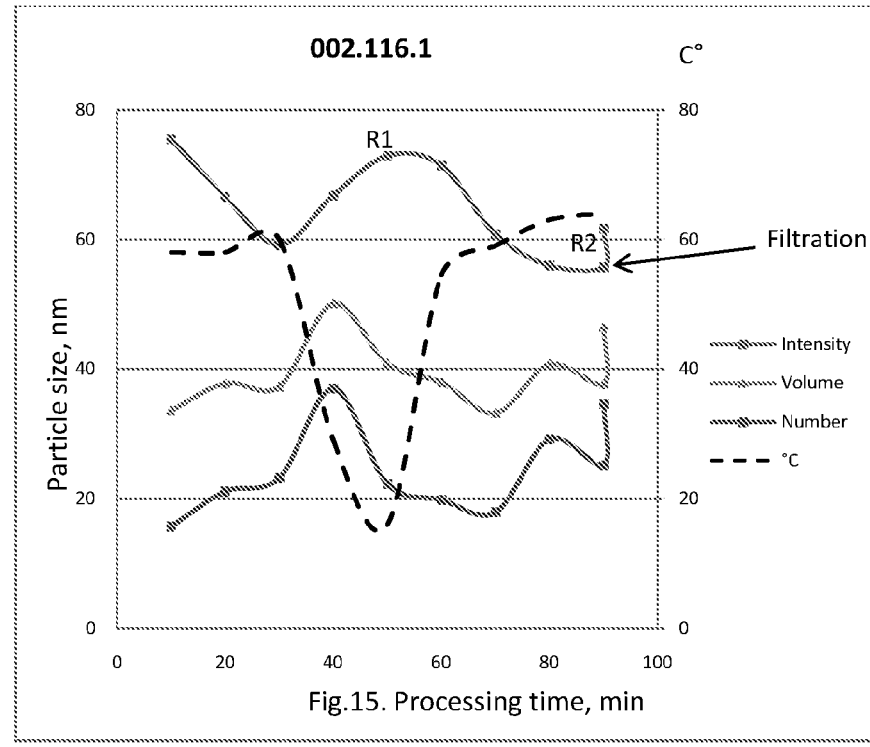
Figure 16: Representative graph showing particle size and stability of ART-207 formulation
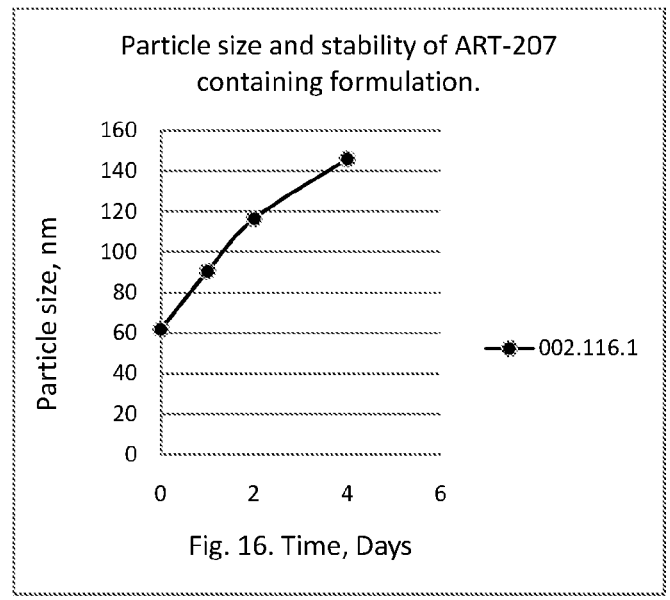

Figure 17: Representative graph showing particle size and processing times
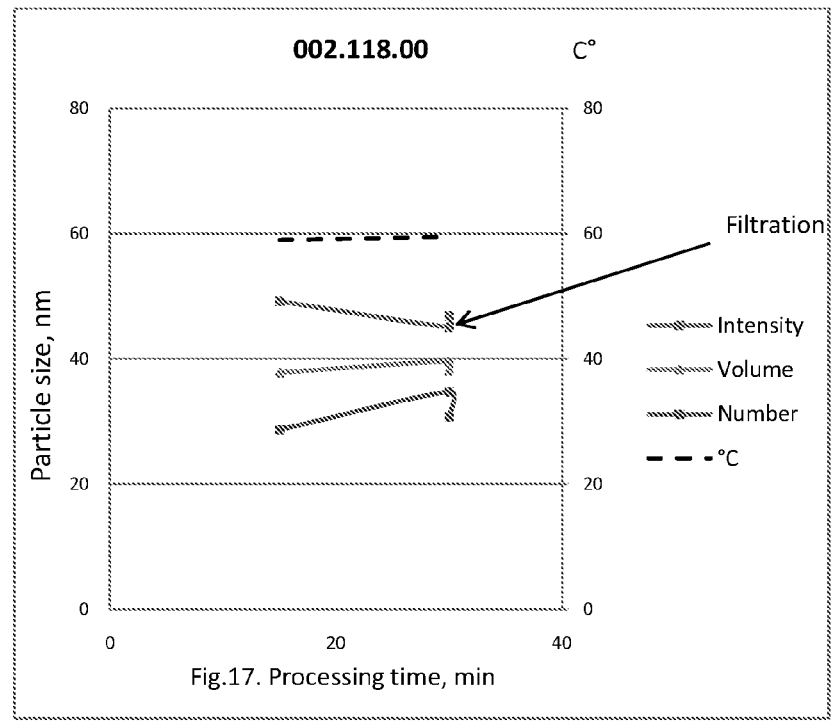
Figure 18: Representative graph showing particle size and stability of drug-free formulations
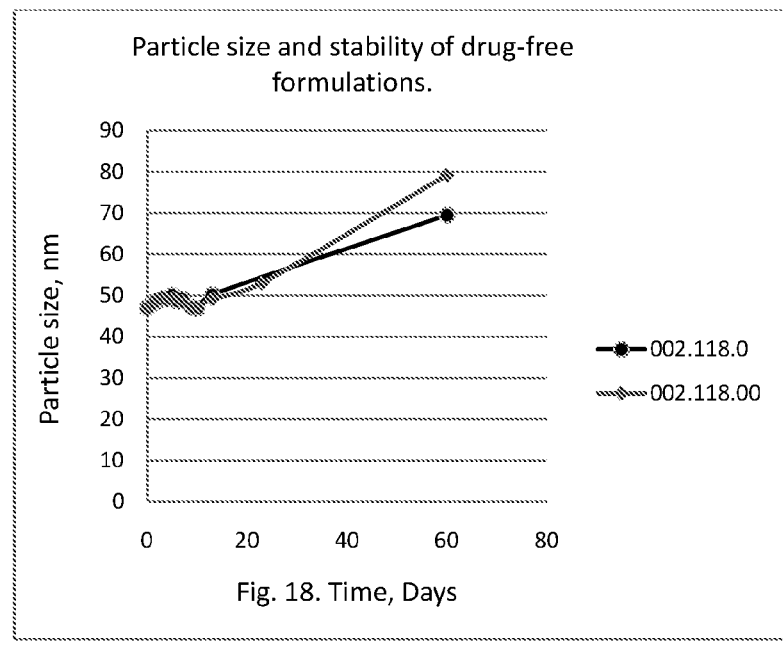

Figure 19: Representative graph showing particle size over processing times and temperatures
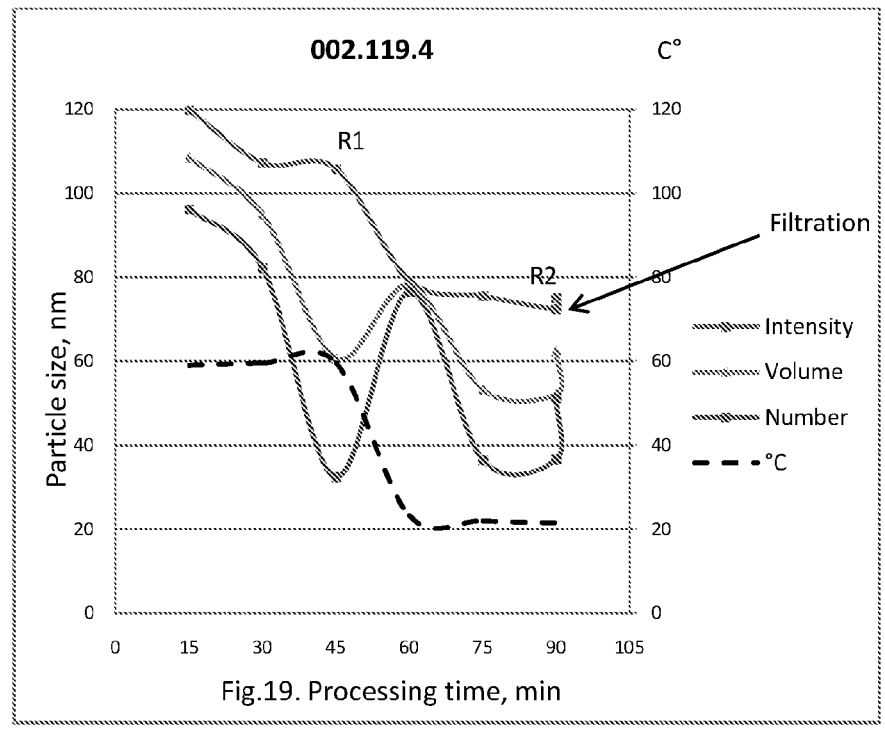
Figure 20: Representative graph showing particle size and stability over time
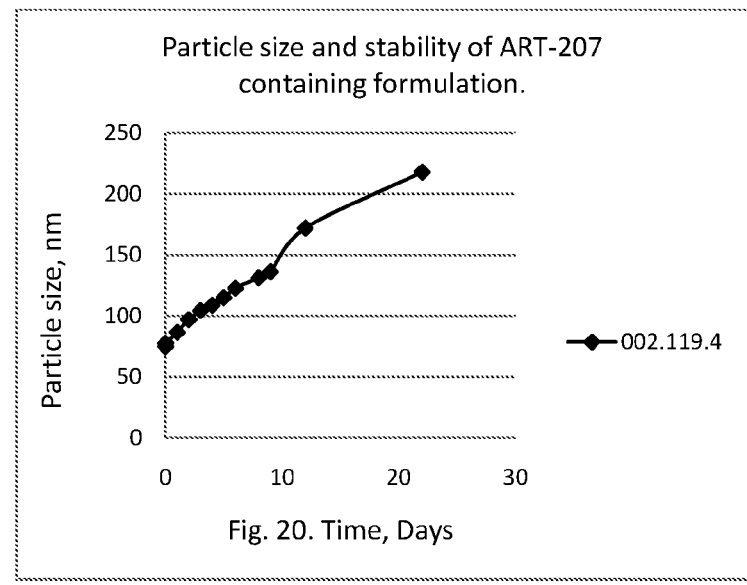

Figure 21: Representative graph showing stability of drug-free and ART-207 containing formulations
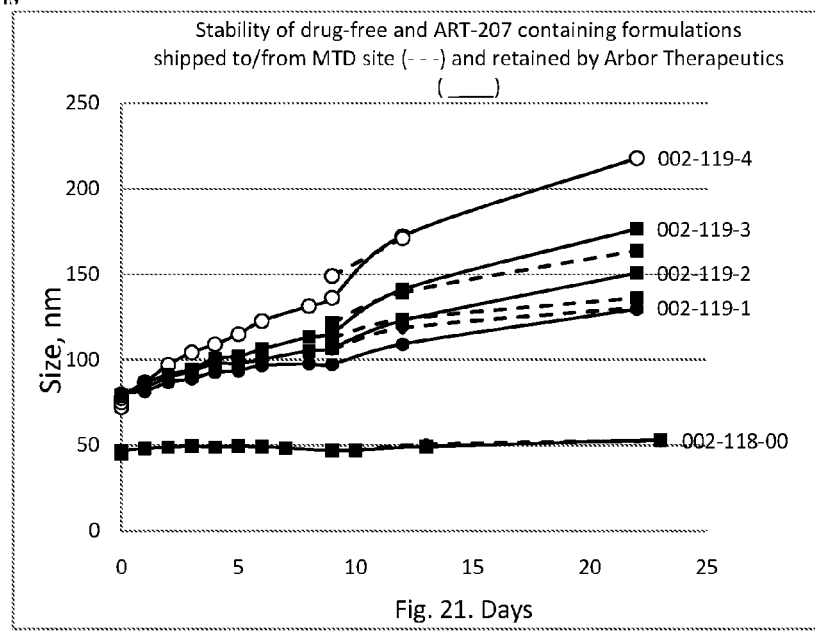
Figure 22: Representative graph of effect of paclitaxel and formulated ART-207 on non-tumored mouse weight
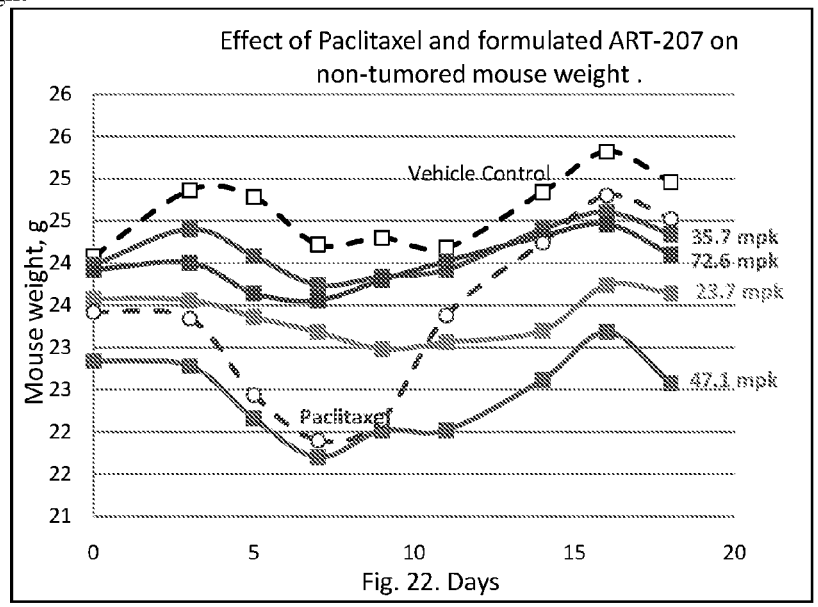

Figure 23: Representative graph of effect of paclitaxel and formulated ART-207 on tumored mouse weight
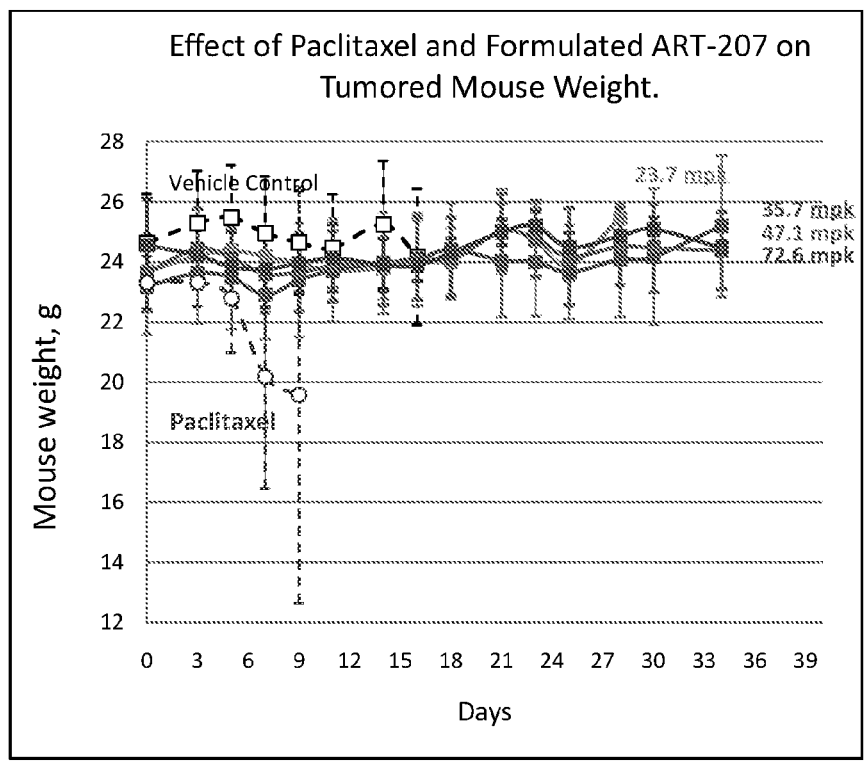
Figure 24: Representative graph of paclitaxel and formulated ART-207 on tumor weight
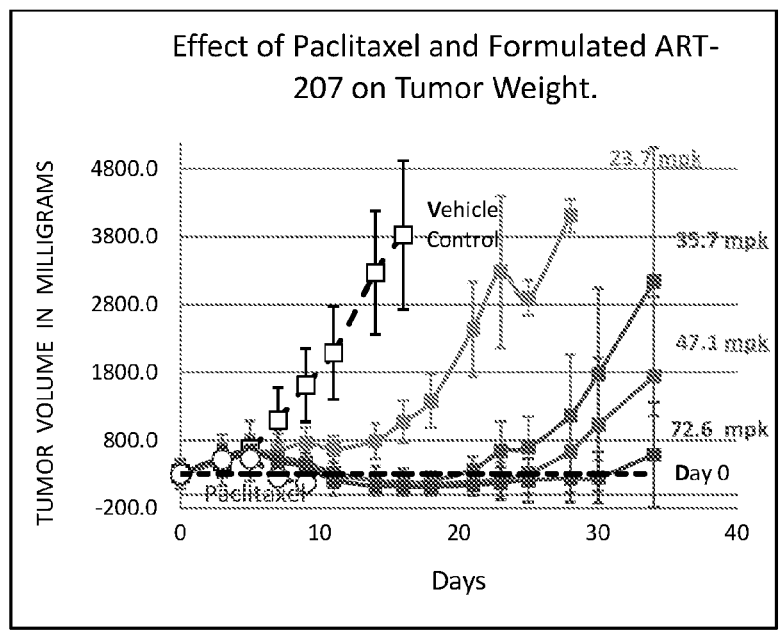

Figure 25: Representative graph of mouse death rate in control and Rx treated groups
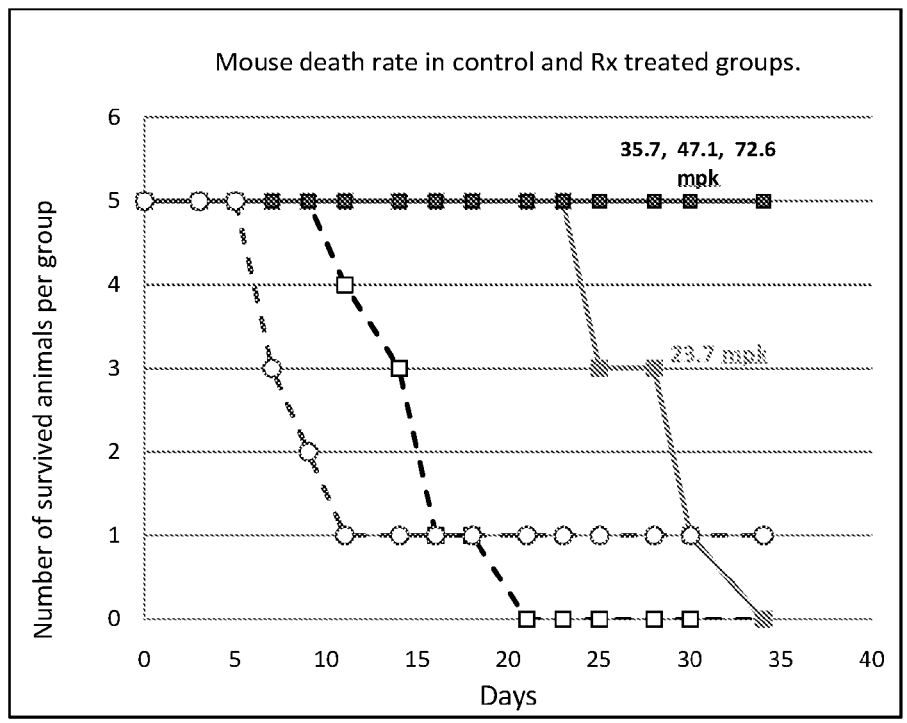
Figure 26: Representative graph showing MF processing time
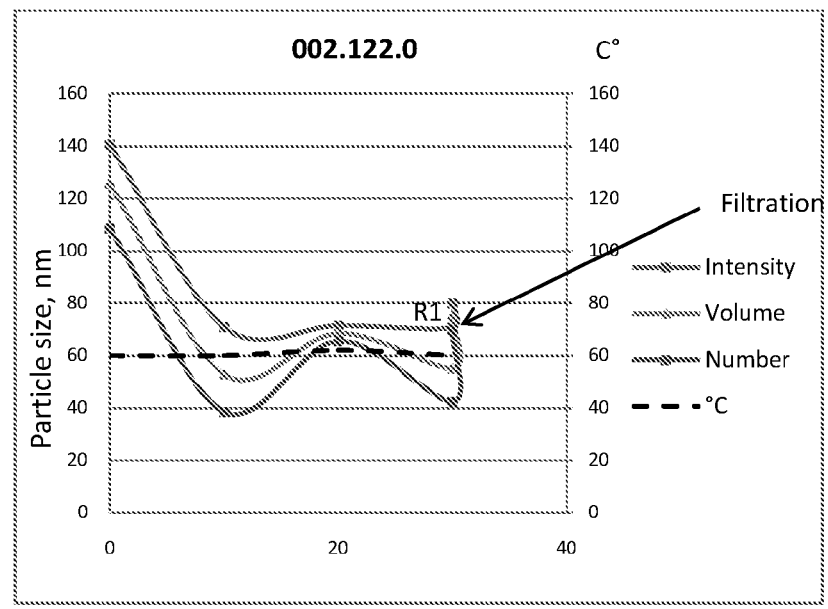

Figure 27: Representative graph showing particle size and stability of ART-207 with formulation
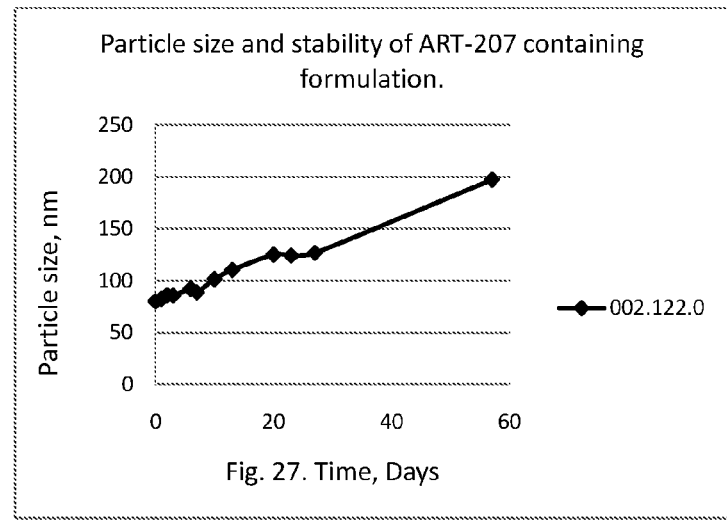
Figure 28: Representative graph showing particle size and processing times
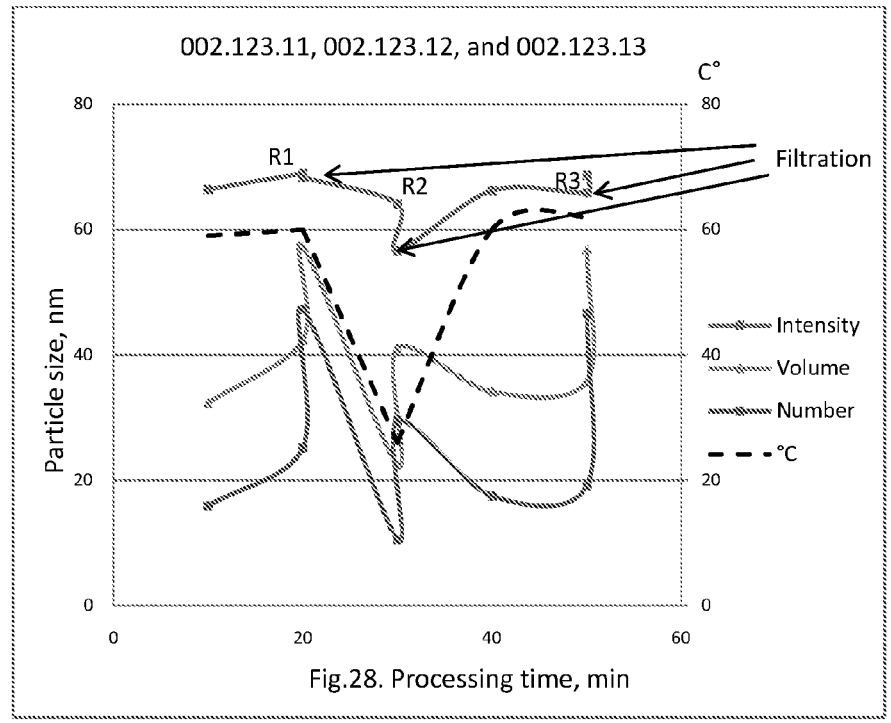

Figure 29: Representative graph showing particle size and stability of ART-207 containing formulation
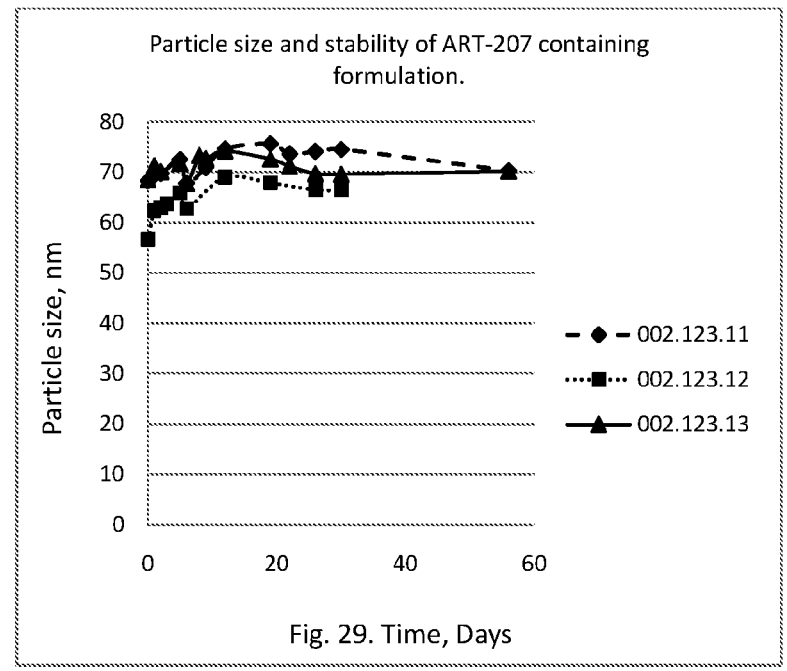
Figure 30: Representative graph showing particle size and processing time
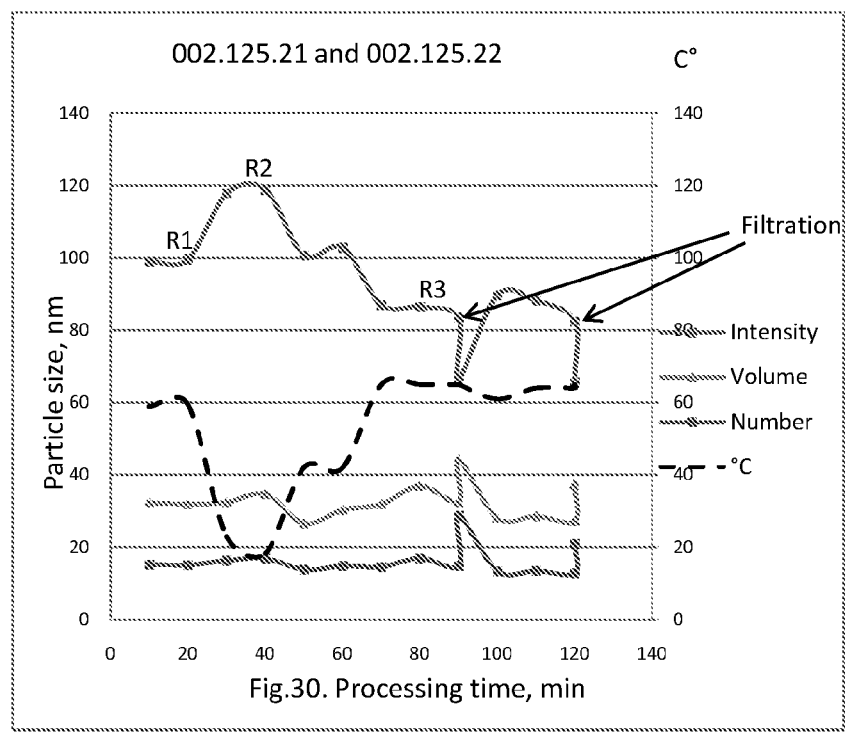

Figure 31: Representative graph showing particle size and stability of ART-207 containing formulation
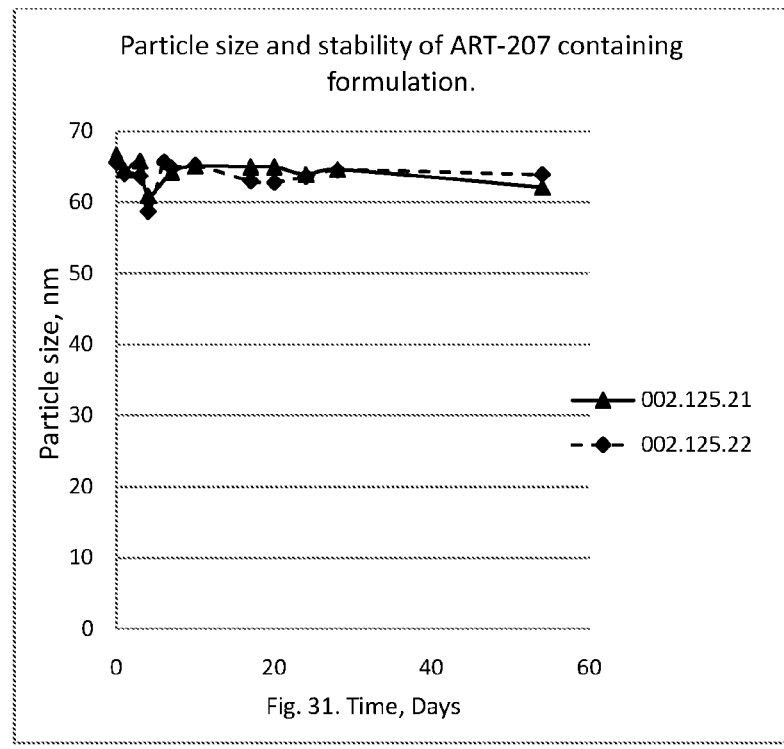
Figure 32: Representative graph showing particle size over processing time.
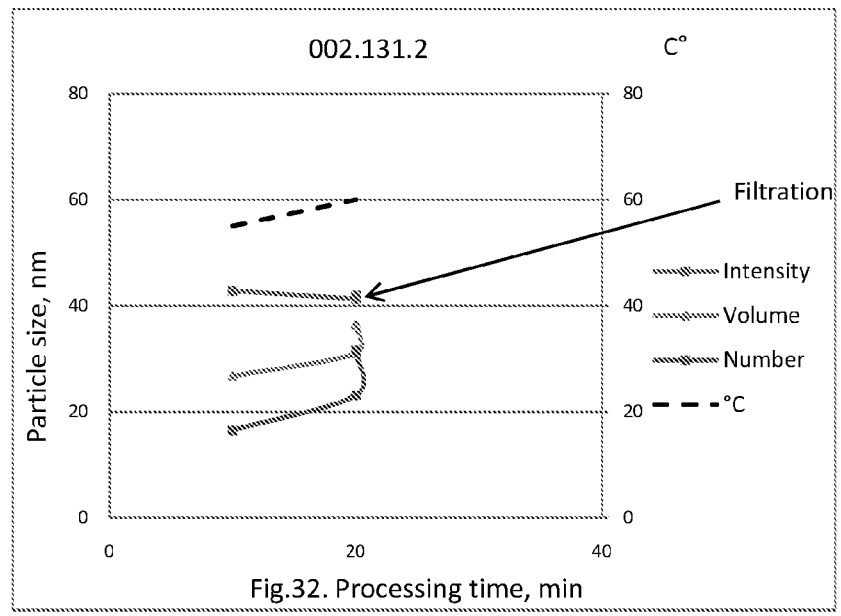

Figure 33: Representative graph showing particle size and stability of drug free formulation
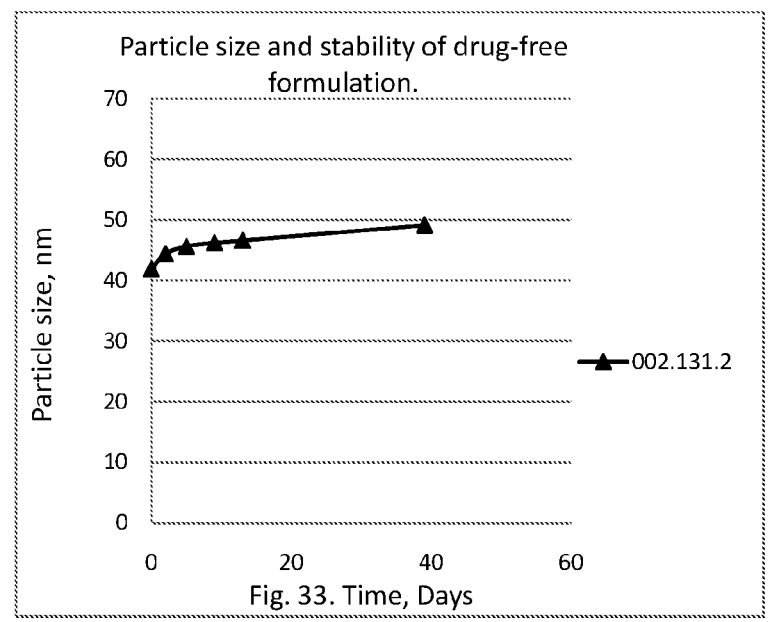
Figure 34: Representative graph showing particle size and processing times
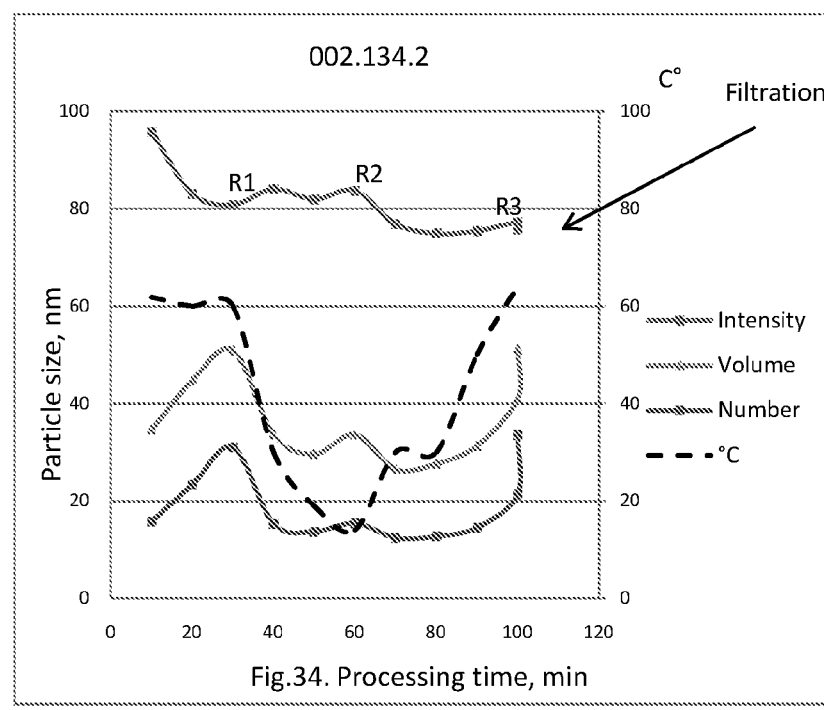

Figure 35: Representative graph showing particle size and stability of ART-207 containing formulation
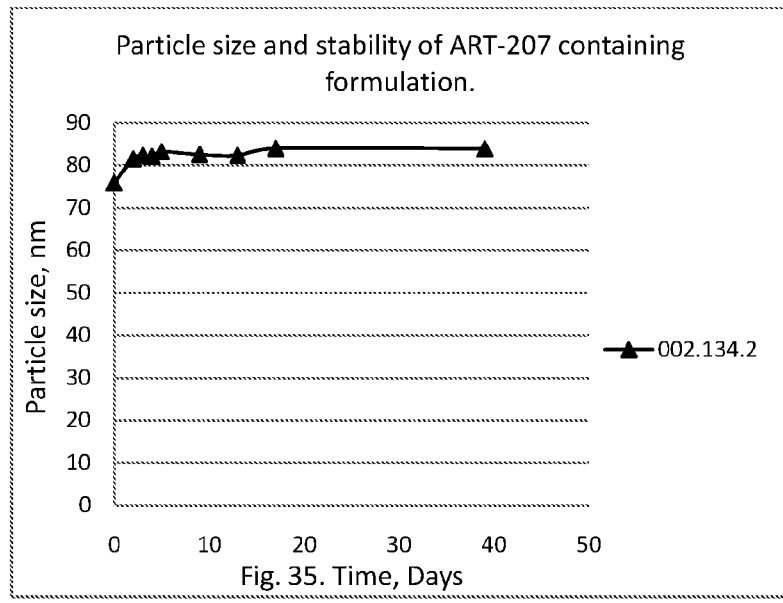
Figure 36: Representative graph showing particle size and processing time.
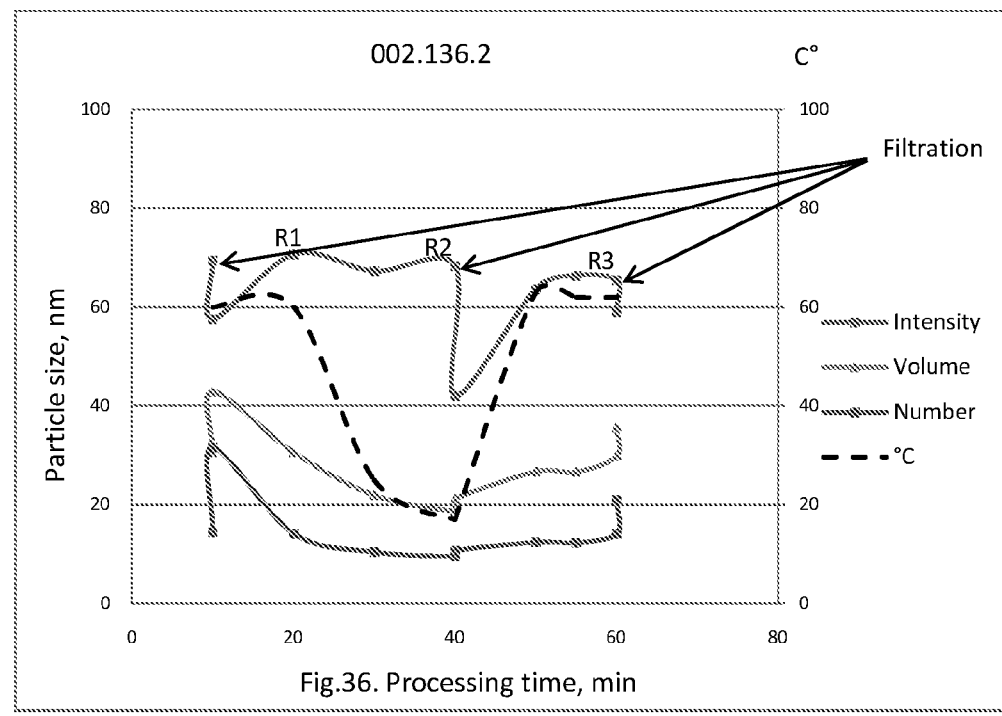

Figure 37: Representative graph showing particle size and stability of ART-207 containing formulation
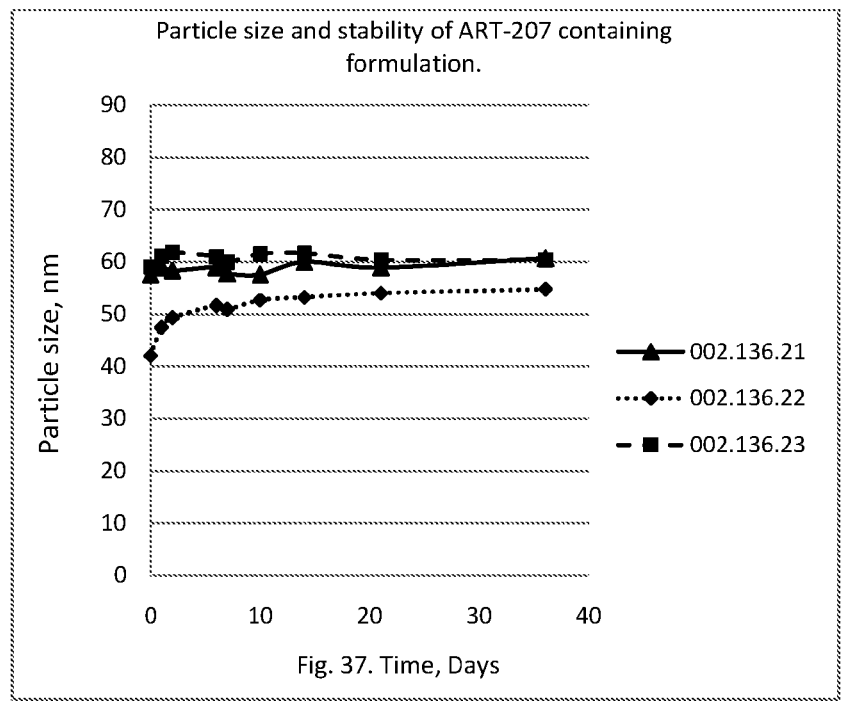
Figure 38: Representative graph showing particle size and processing time
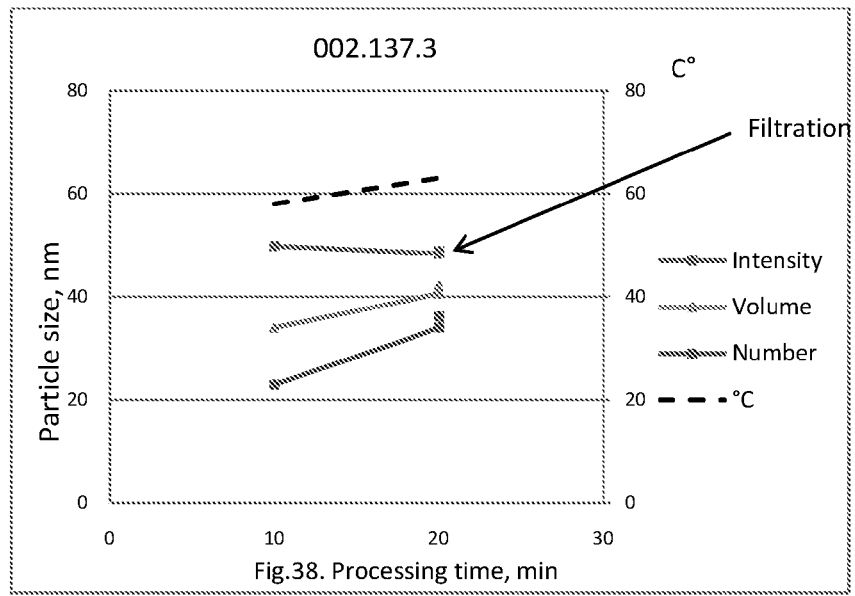

Figure 39: Representative graph showing particle size and stability of ART-207 containing formulation
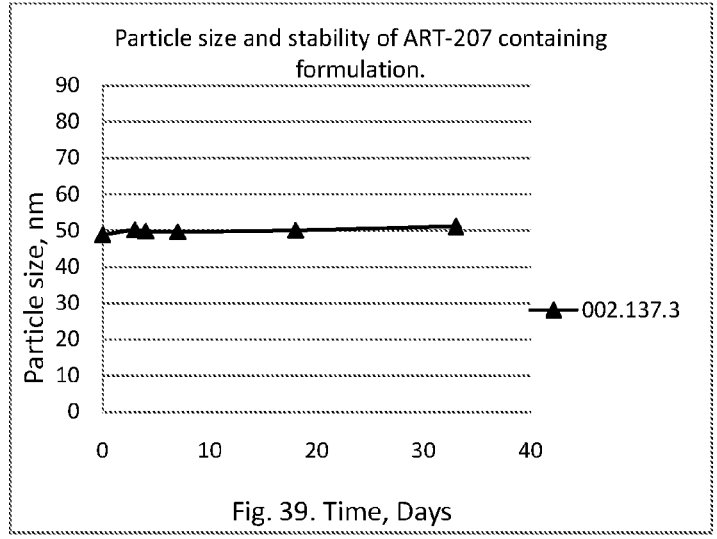
Figure 40: Representative graph showing particle size and processing time
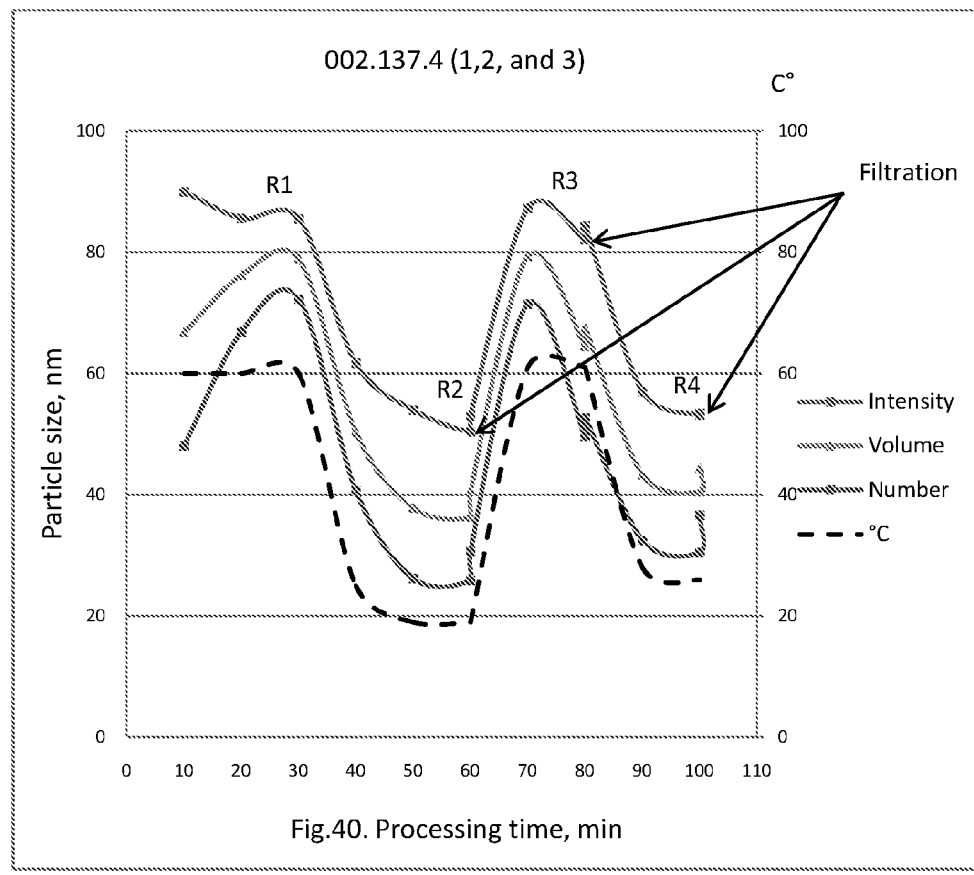

Figure 41: Representative graph showing particle size and stability of ART-207 containing formulation
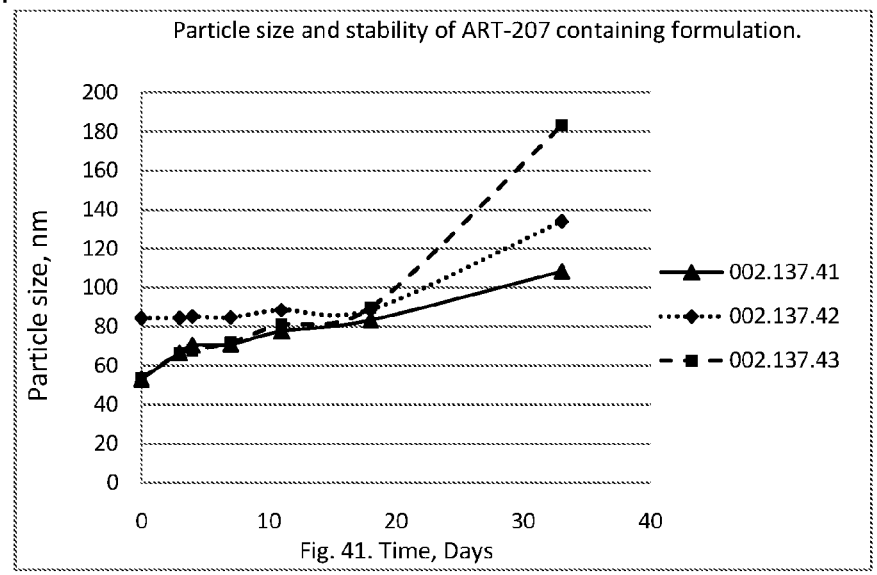
Figure 42: Representative graph showing particle size and processing time
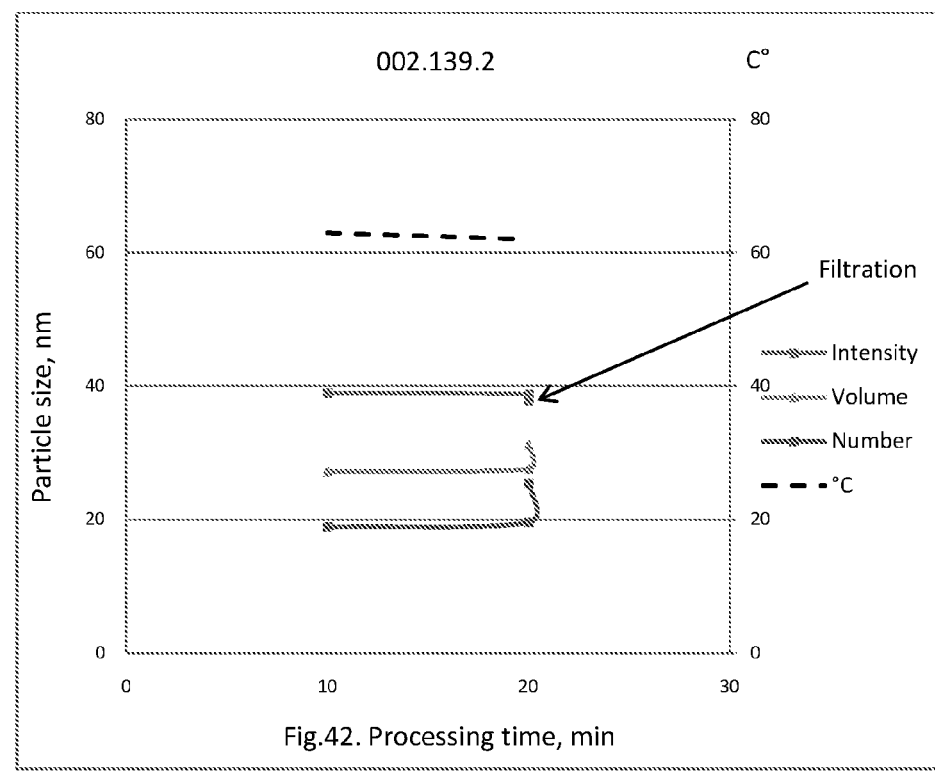

Figure 43: Representative graph showing particle size and stability of drug free formulation
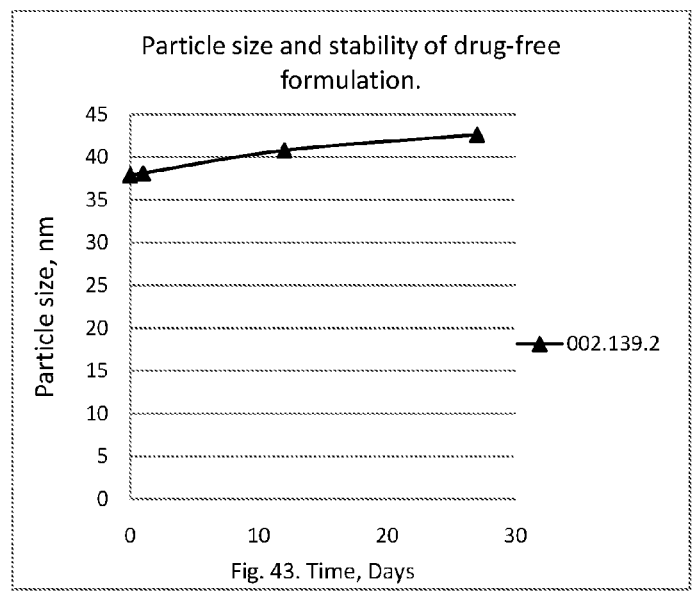
Figure 44: Representative graph showing particle size and processing time
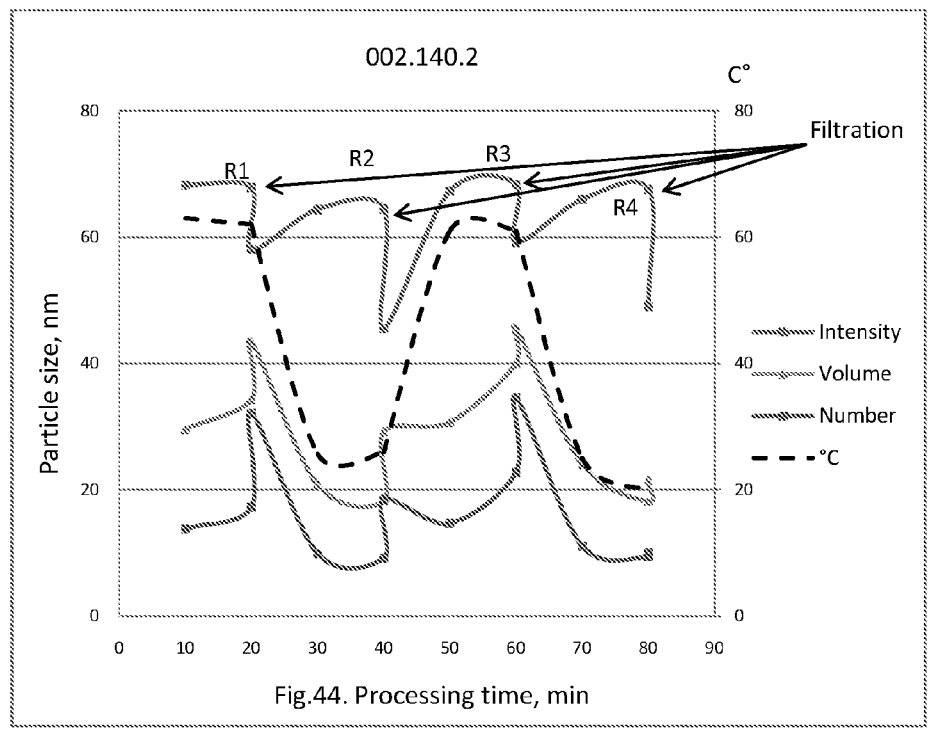

Figure 45: Representative graph showing particle size and stability of ART-207 containing formulation
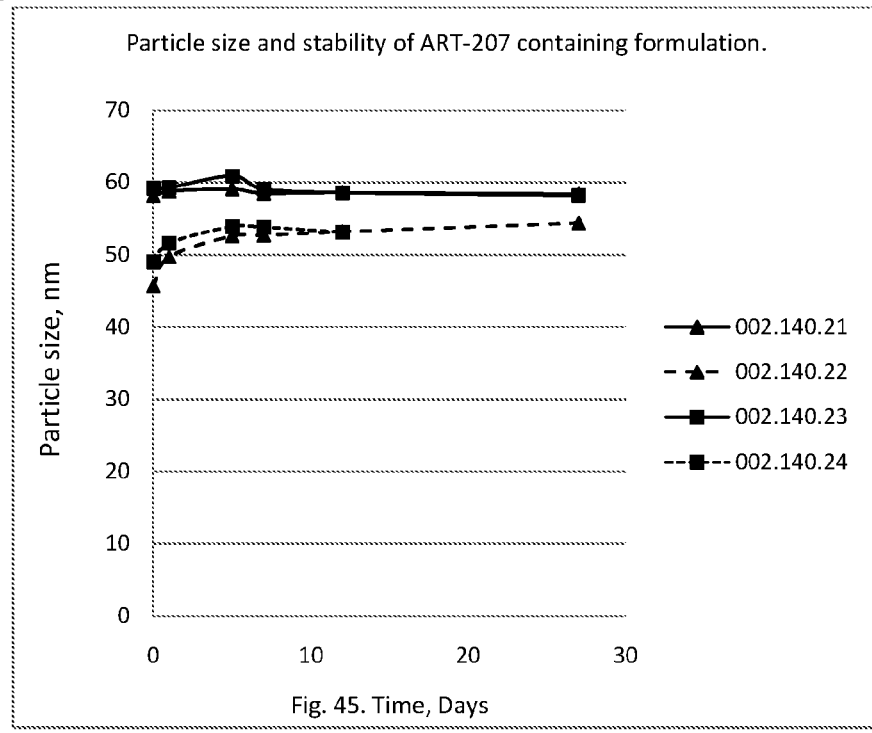
Figure 46: Representative graph showing particle size and processing time
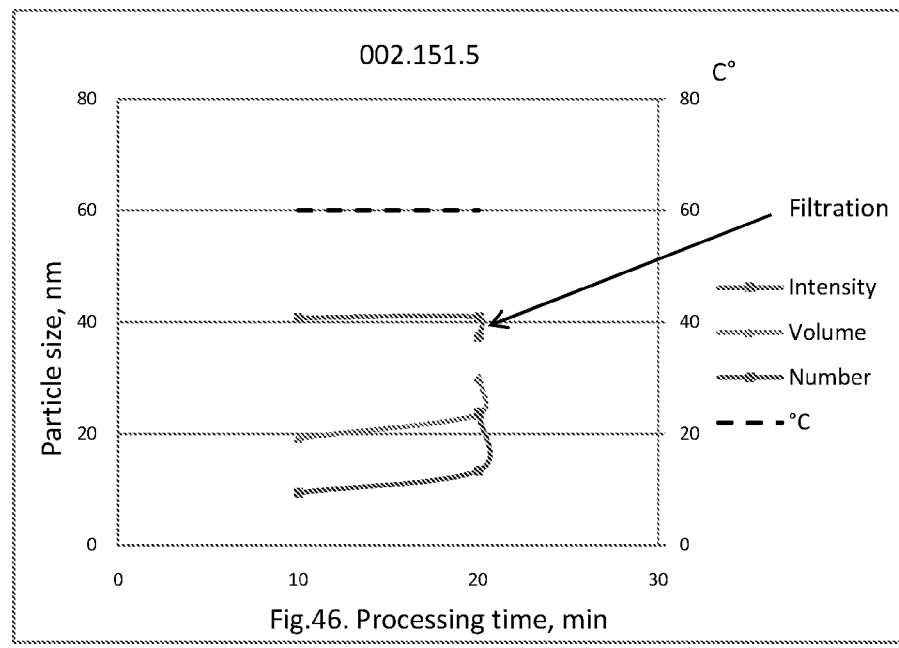

Figure 47: Representative graph showing particle size and stability of drug-free formulation
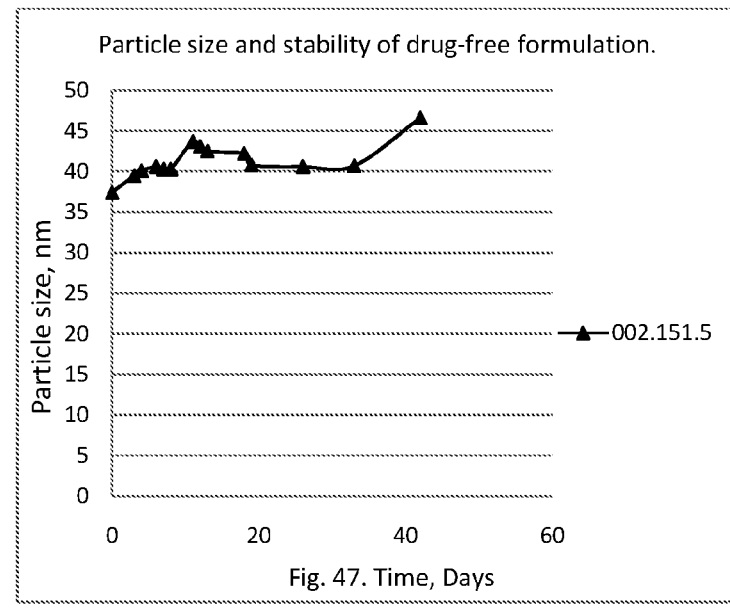
Figure 48: Representative graph showing particle size and processing time
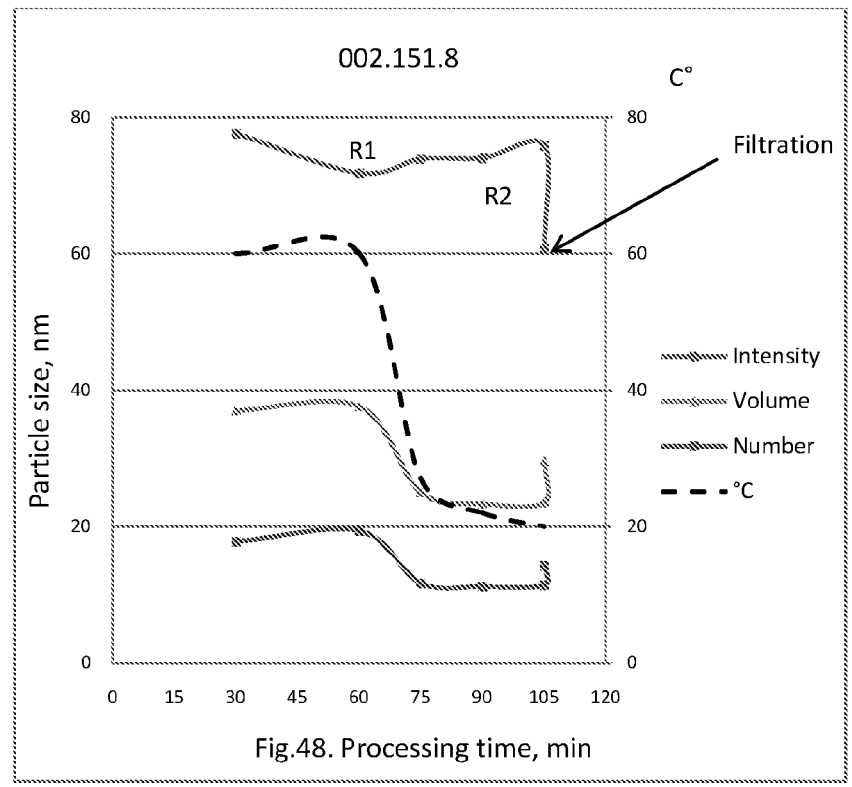

Figure 49: Representative graph showing particle size and stability of ART-207 containing formulation
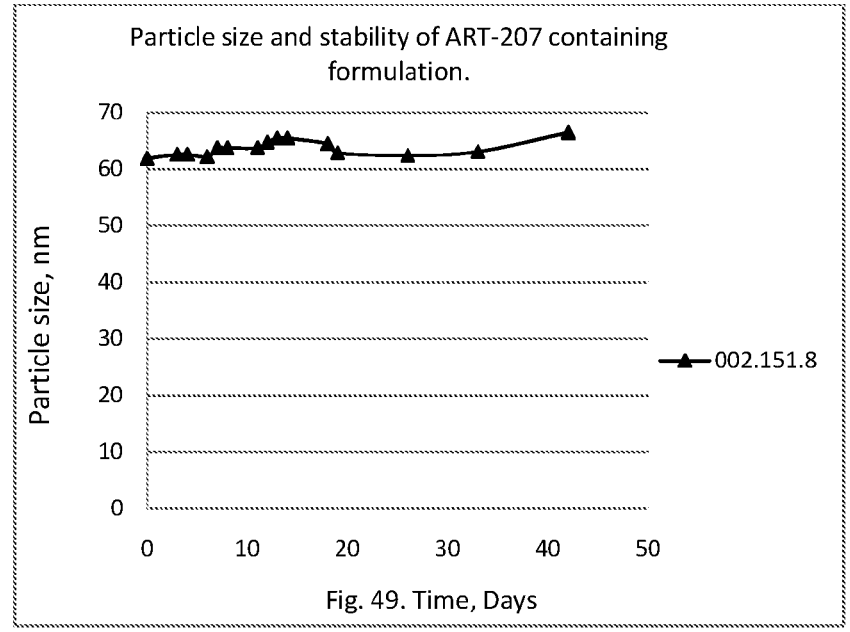
Figure 50: Representative graph showing particle size and processing time
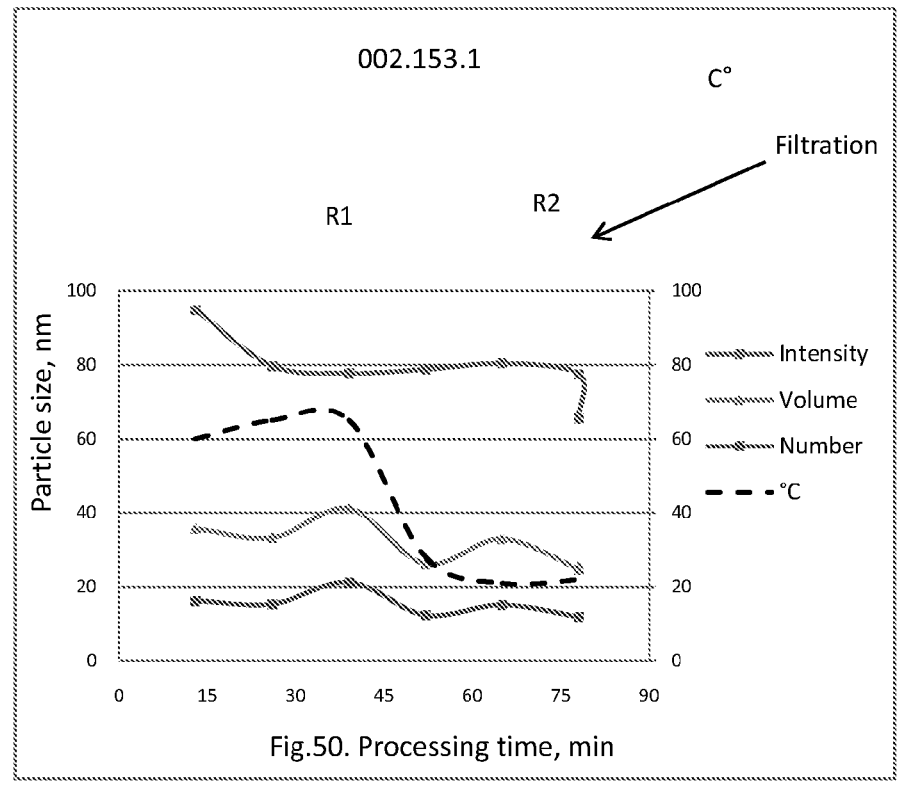

Figure 51: Representative graph showing particle size and stability of ART-207 containing formulation
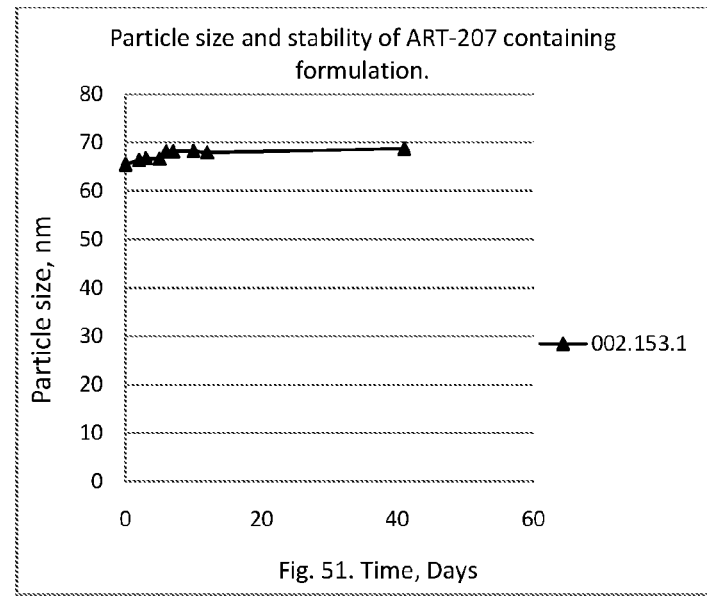
Figure 52: Representative graph of particle size and processing time
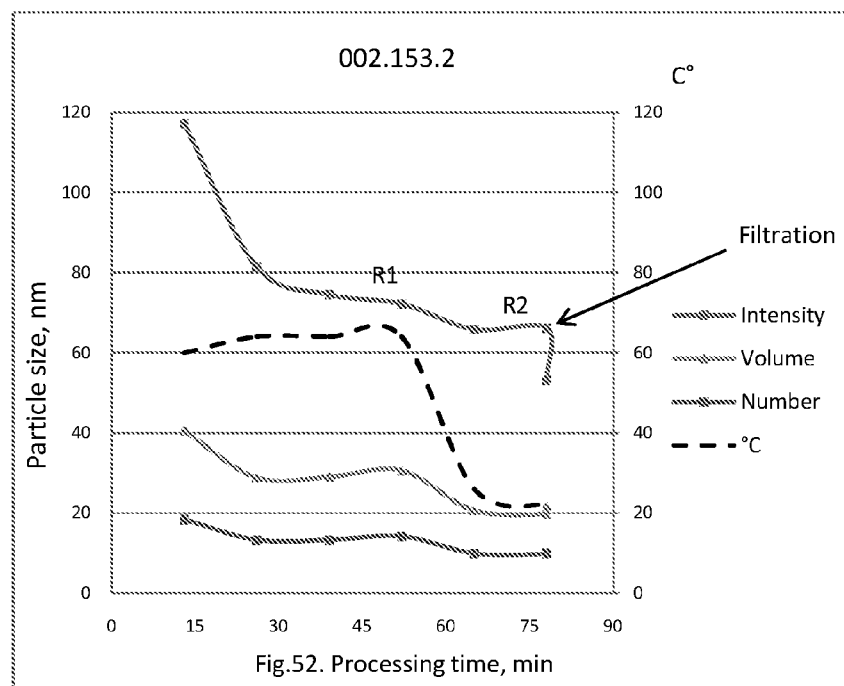

Figure 53: Representative graph showing particle size and stability of ART-207 containing formulation
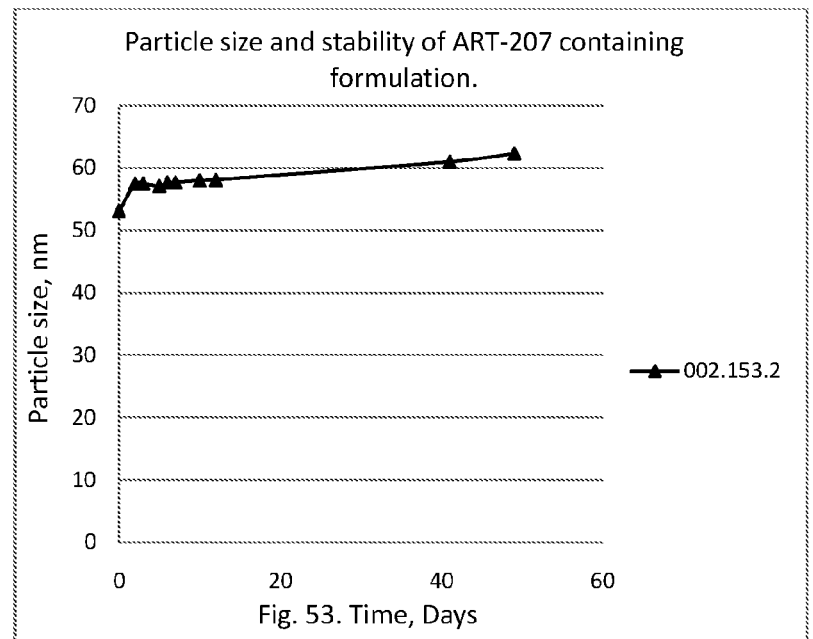
Figure 54: Representative graph showing particle size and stability of drug-free and ART-207 containing formulation
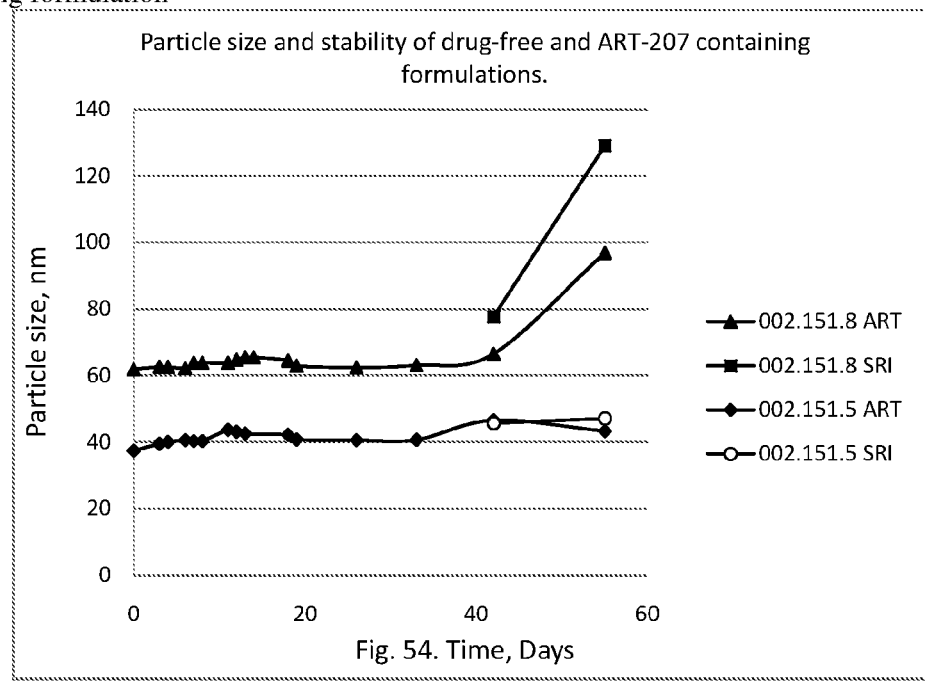

Figure 55: Representative graph showing effect of paclitaxel and formulated ART-207 on tumor growth
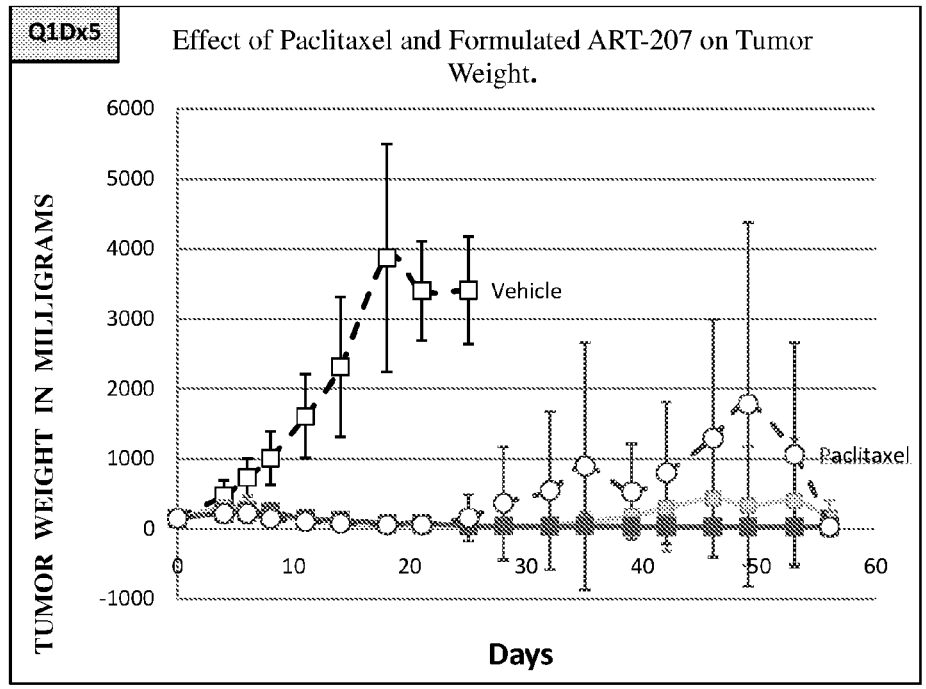
Figure 56: Representative graph showing effect of paclitaxel and formulated ART-207 on tumored mouse weight
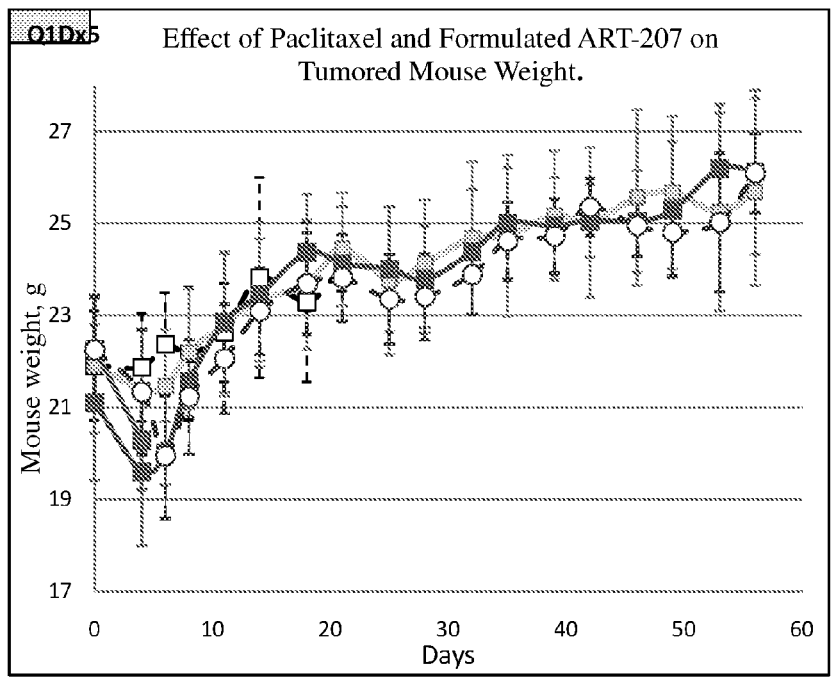

Figure 57: Representative graph of mouse death rate in control and Rx treated groups
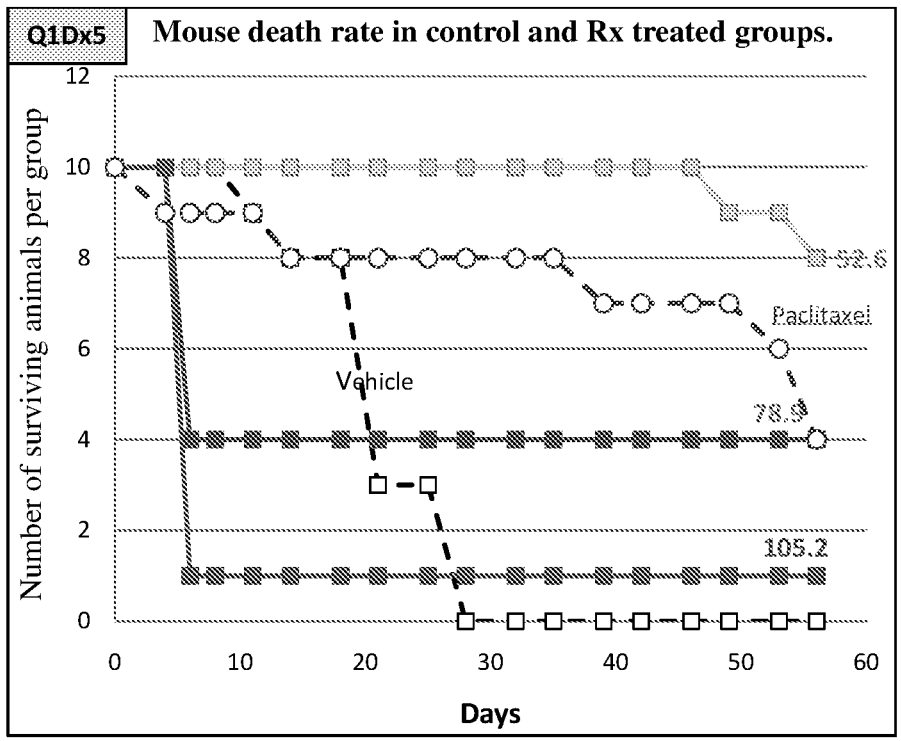
Figure 58: Effect of paclitaxel and formulated ART-207 on tumored mouse weight
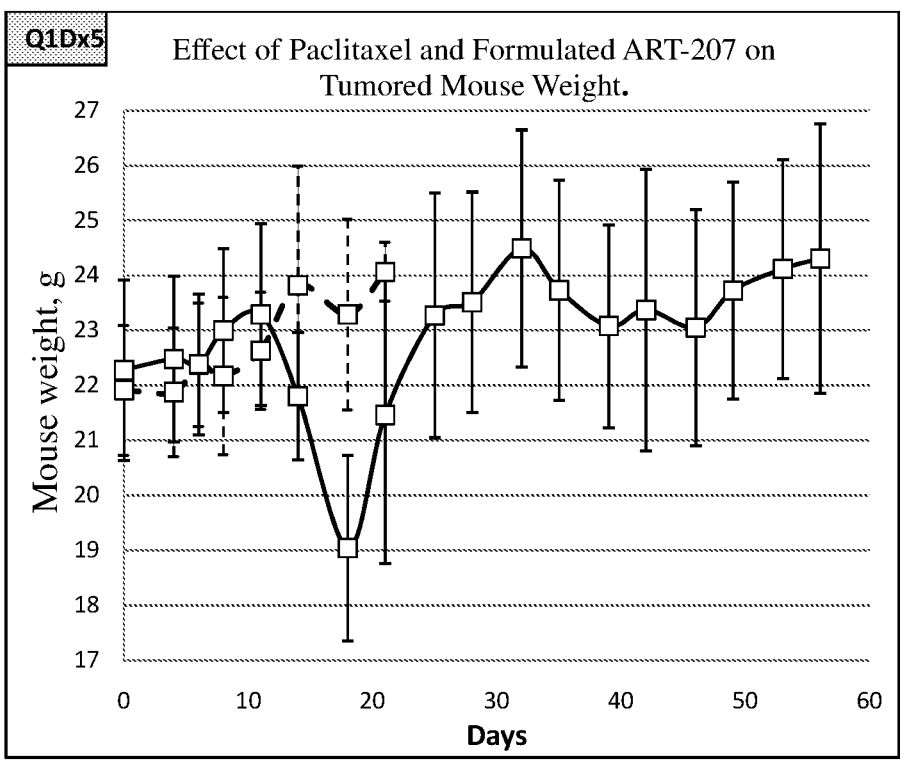

Figure 59: Effect of formulated ART-207 on tumor weight
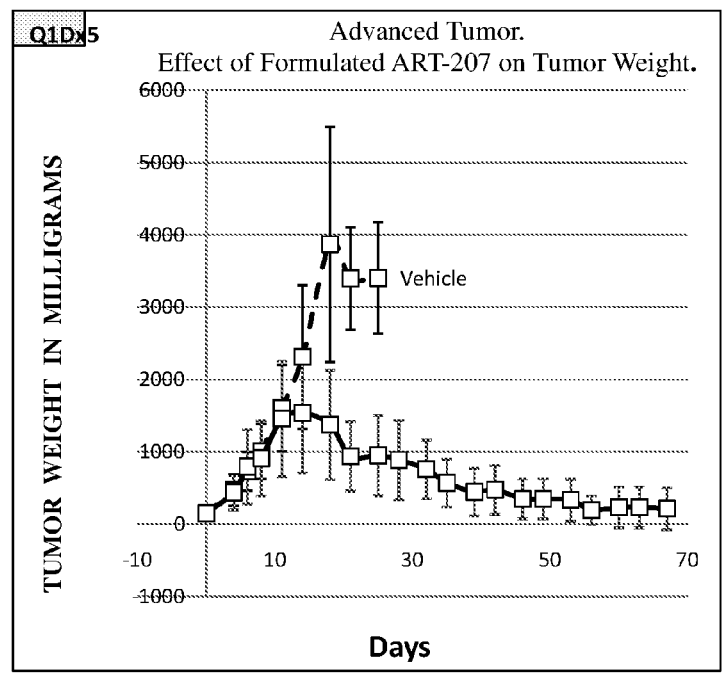
Figure 60a: Representative graph showing effect of paclitaxel and formulated ART-207 on tumor weight
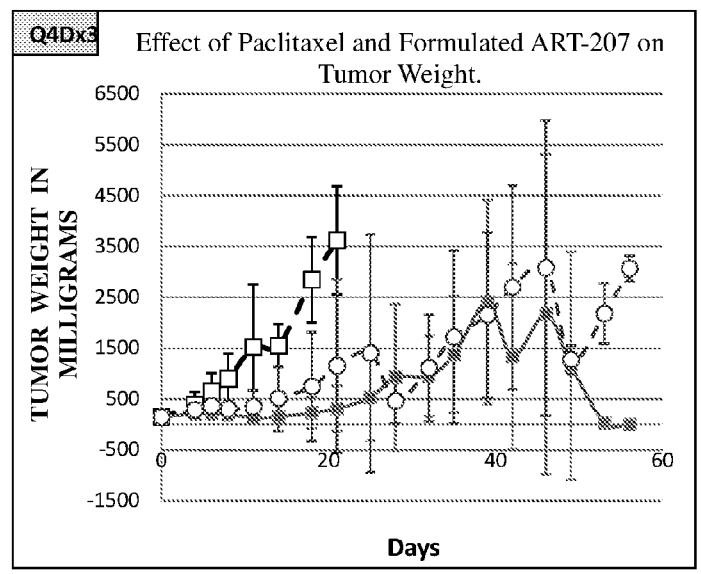

Figure 60b: Representative graphs showing effect of paclitaxel and formulated ART-207 on tumored mouse weight
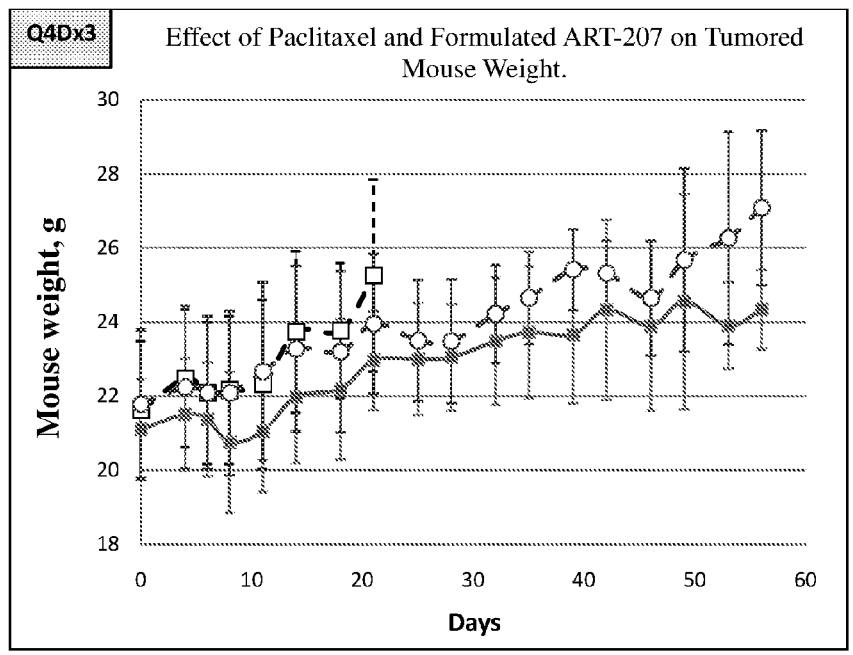
Figure 61: Representative graphs showing particle size and processing time.
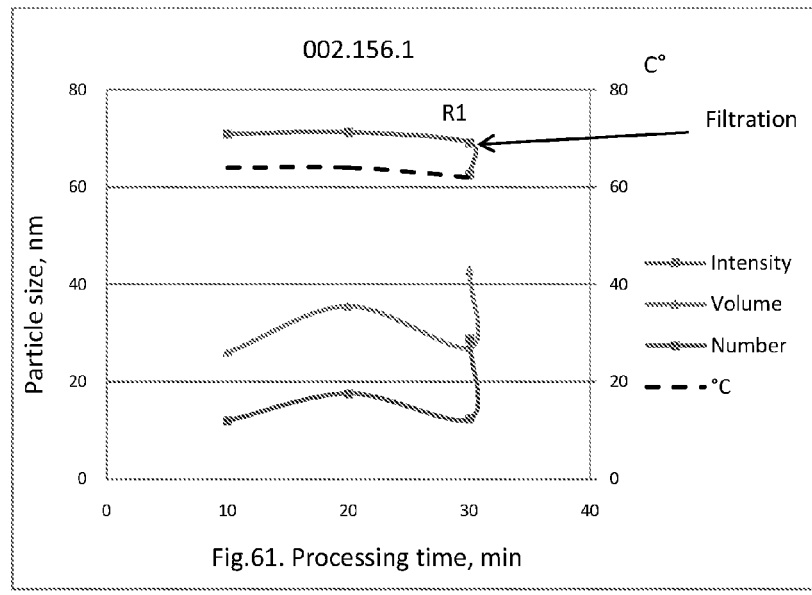

Figure 62: Representative graph showing particle size and stability of ART-207 containing formulation
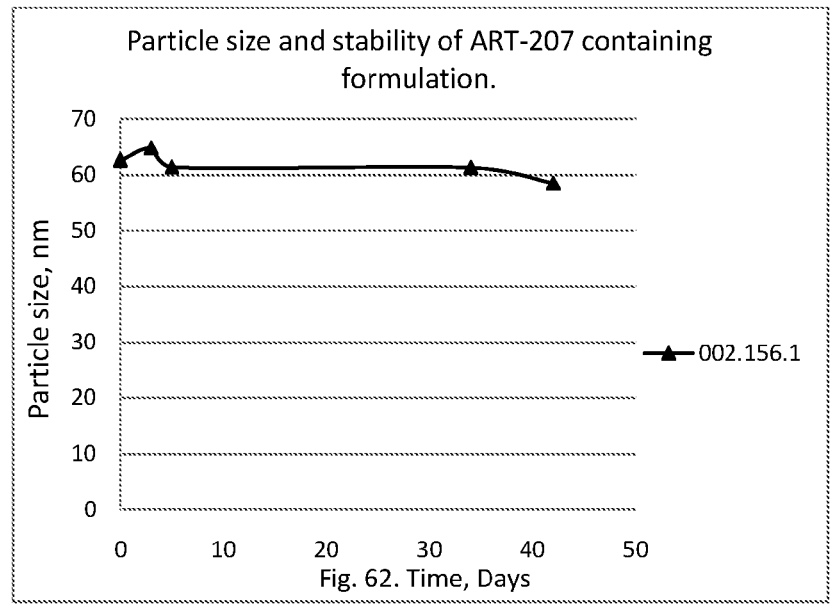
Figure 63: Representative graph showing particle size and processing time.
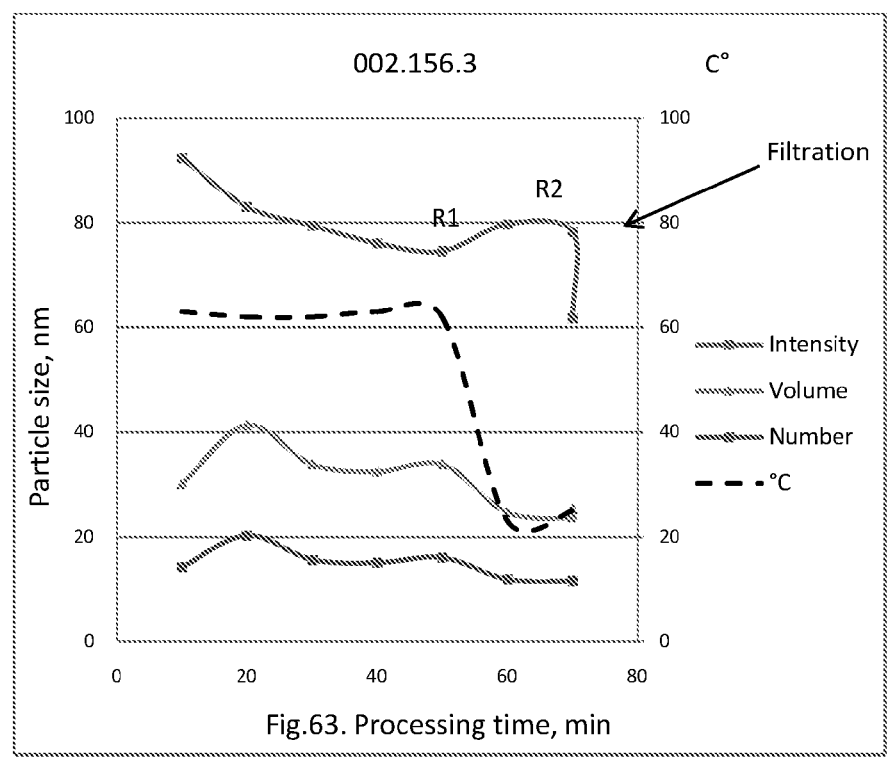

Figure 64: Representative graph showing particle size and stability of ART-207 containing formulation.
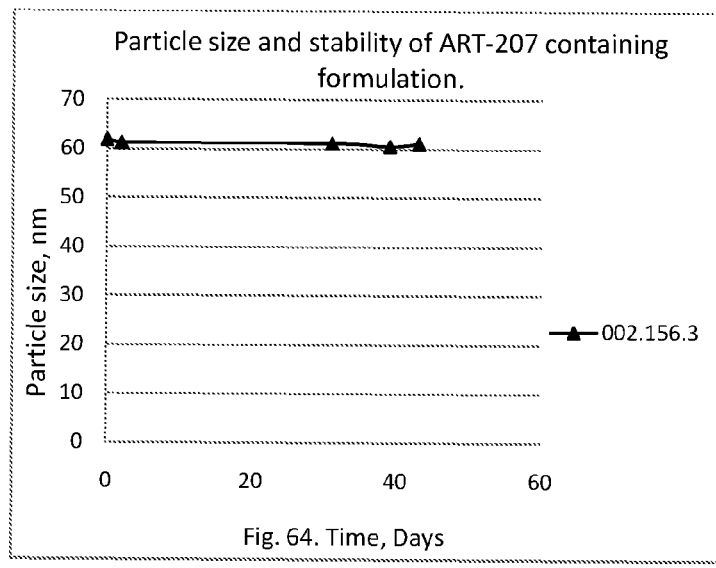
Figure 65: Representative graphs showing results of treatment of tumored and non-tumored mice
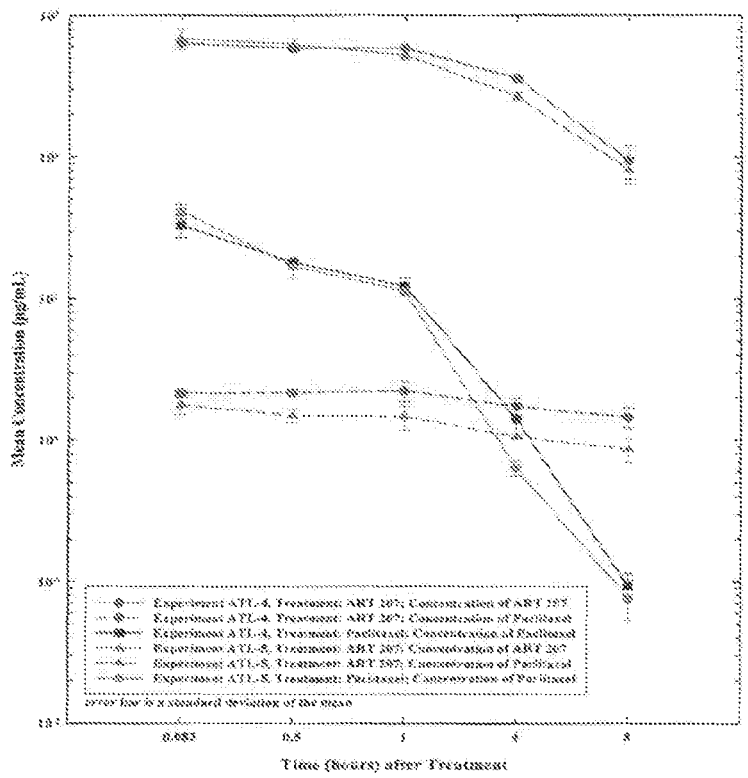

Figure 66: Representative graph of plasma levels of paclitaxel
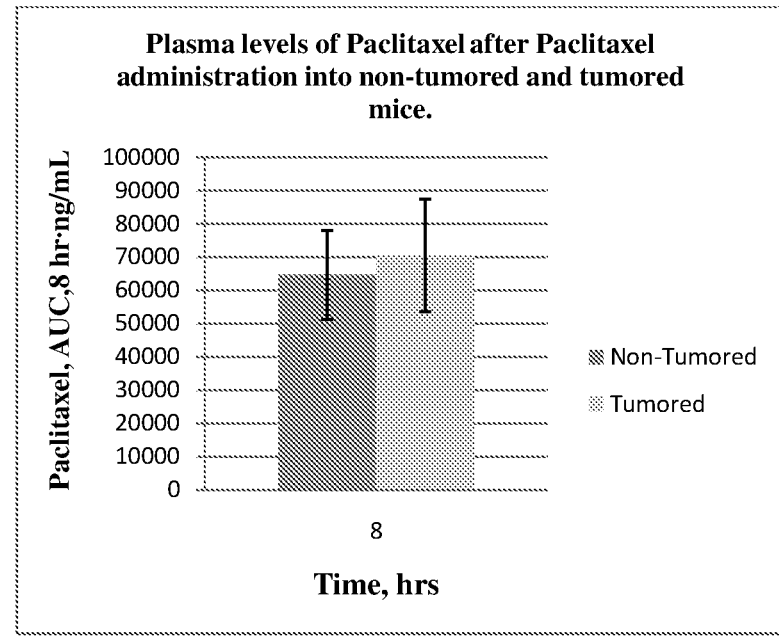
Figure 67: Plasma levels of ART-207 after administration
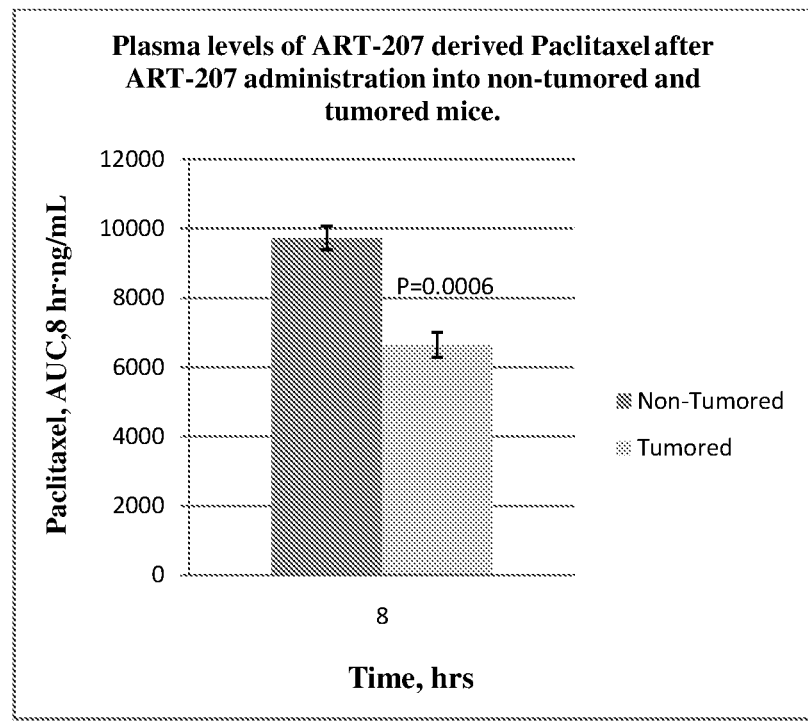

Figure 68: Concentration of paclitaxel in tissues of non-tumored mice injected with paclitaxel or formulated ART-207
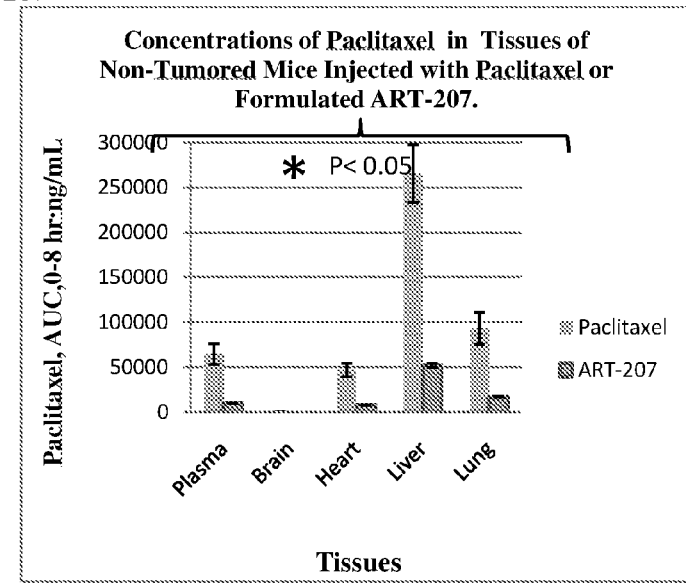
Figure 69: Representative graph showing concentration of paclitaxel in tissues in tumored mice injected with paclitaxel or formulated ART-207
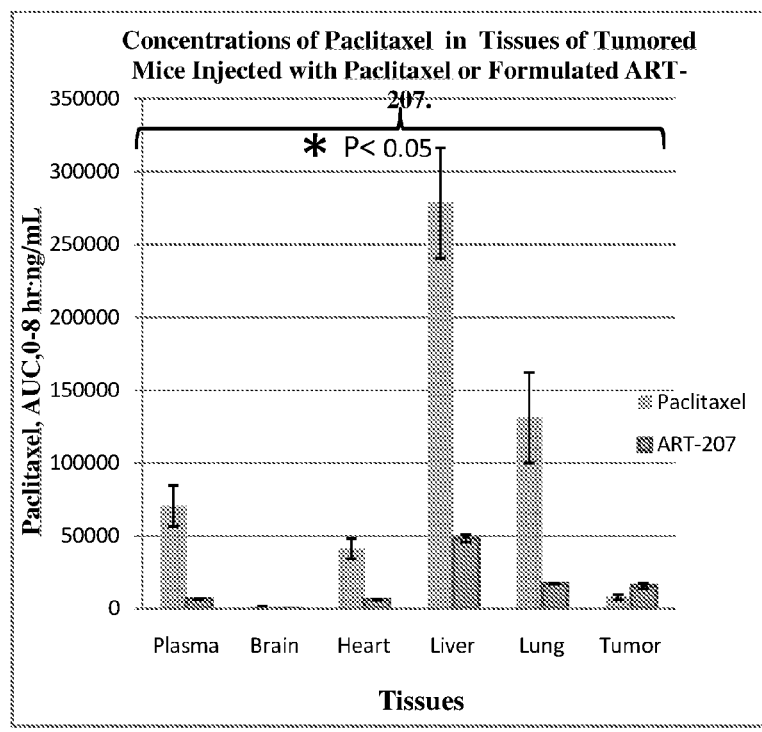

Figure 70: Representative graph showing tumor concentrations of paclitaxel in tumored mice injected with palcitaxel or formulated ART-207.
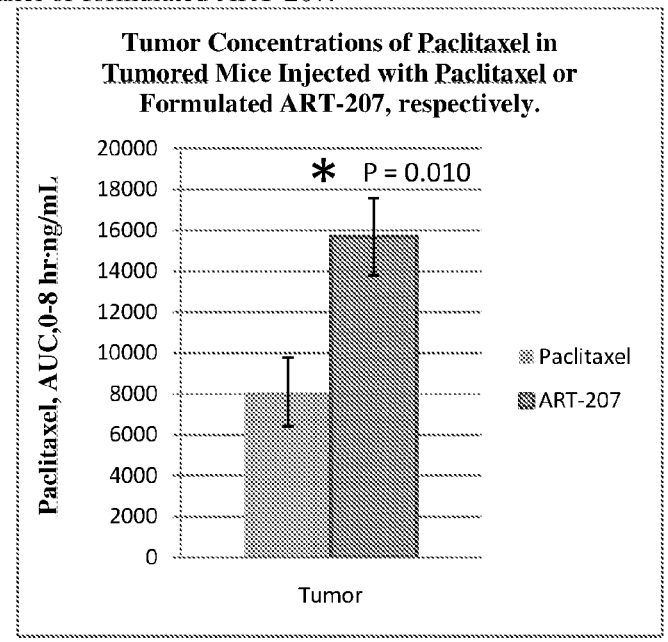
Figure 71: Representative graph showing particle size and processing time.
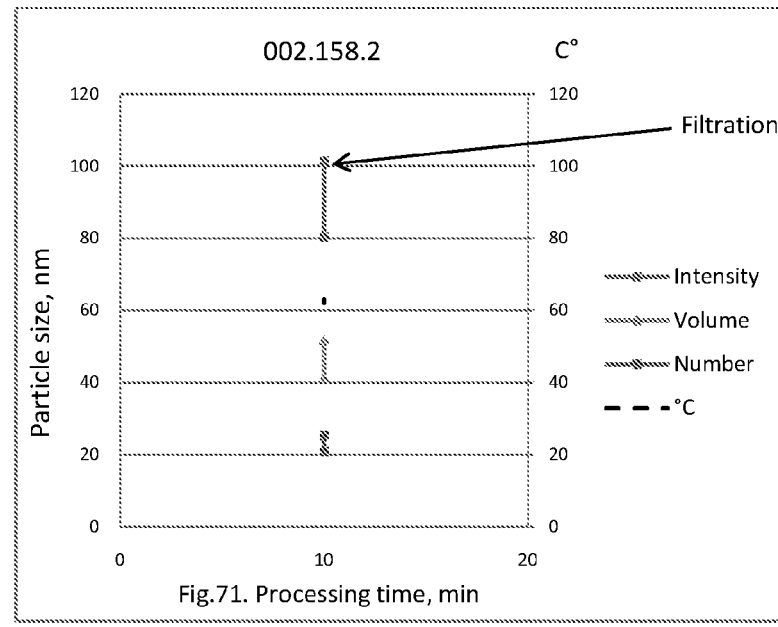

Figure 72: Representative graph showing particle size and stability of ART-207 containing formulation
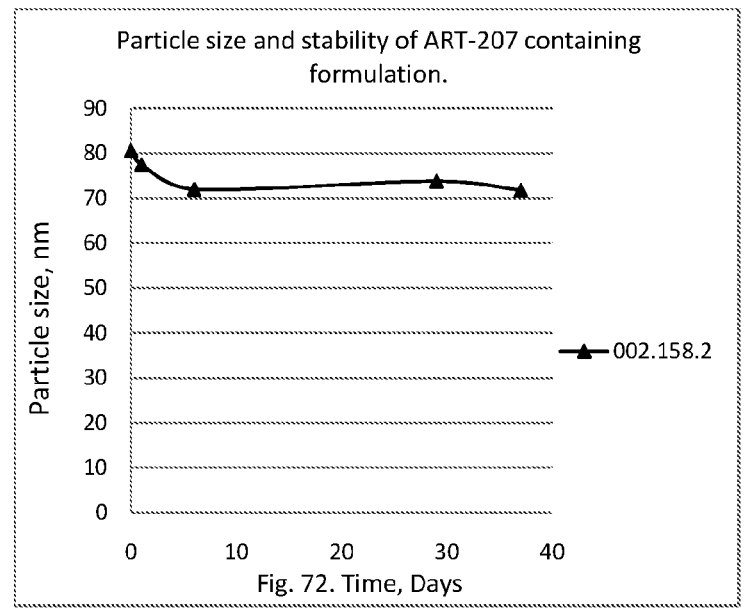
Figure 73: Representative graph showing particle size and processing time
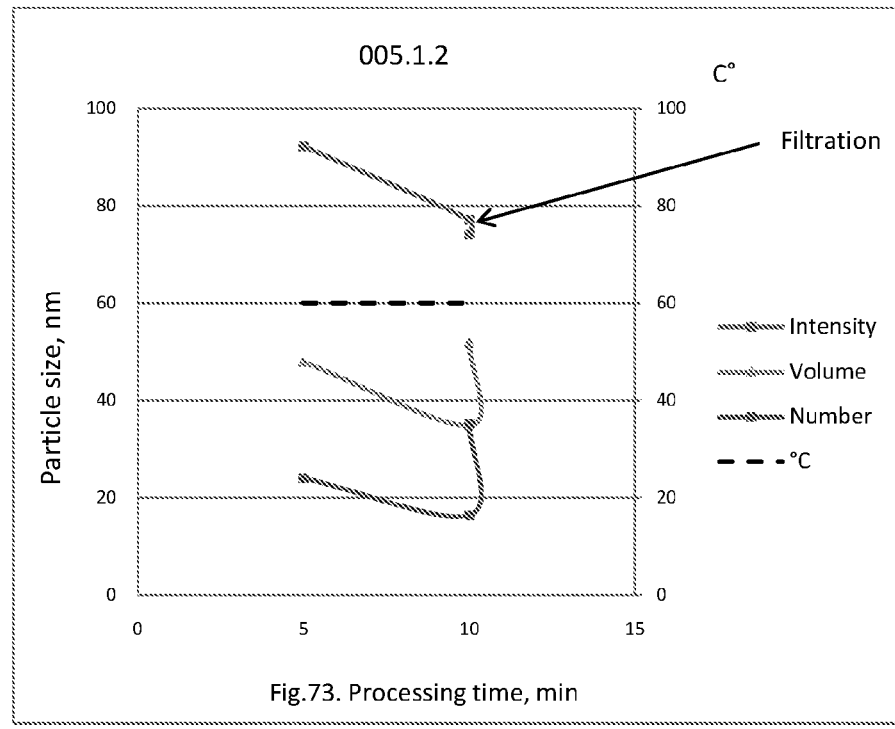

Figure 74: Representative graphs showing particle size and stability of ART-207 containing formulation
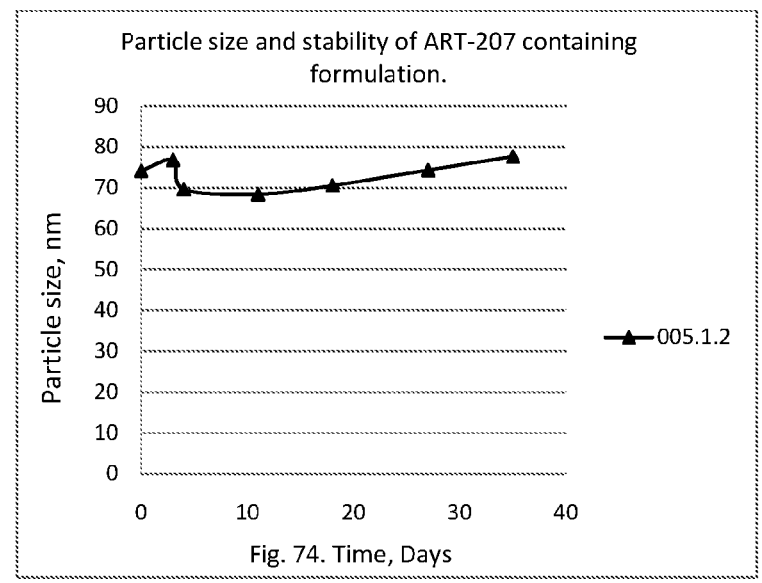
Figure 75: Representative graphs showing article size and processing time in minutes
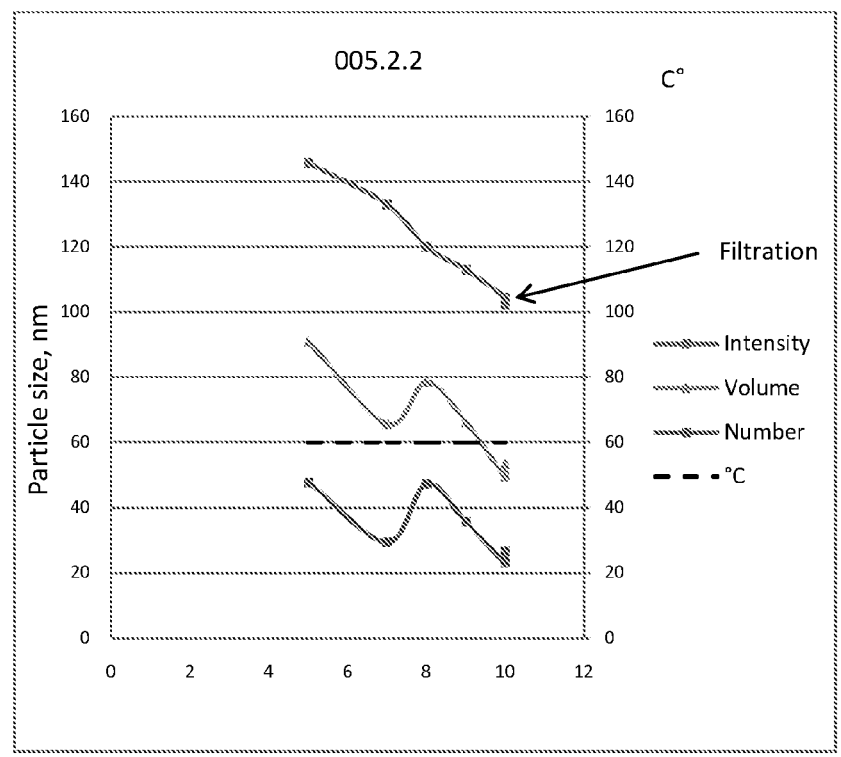

Figure 76: Representative graph showing particle size and stability with time in days
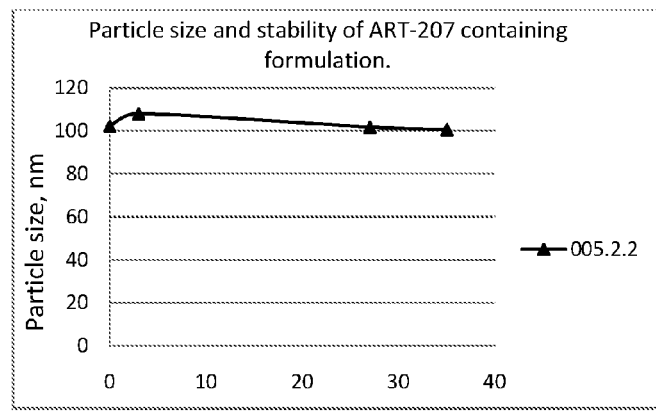
Figure 77: Representative graph showing Effect of TG/ART-207 ratio on ART-207 incorporation and particle stability
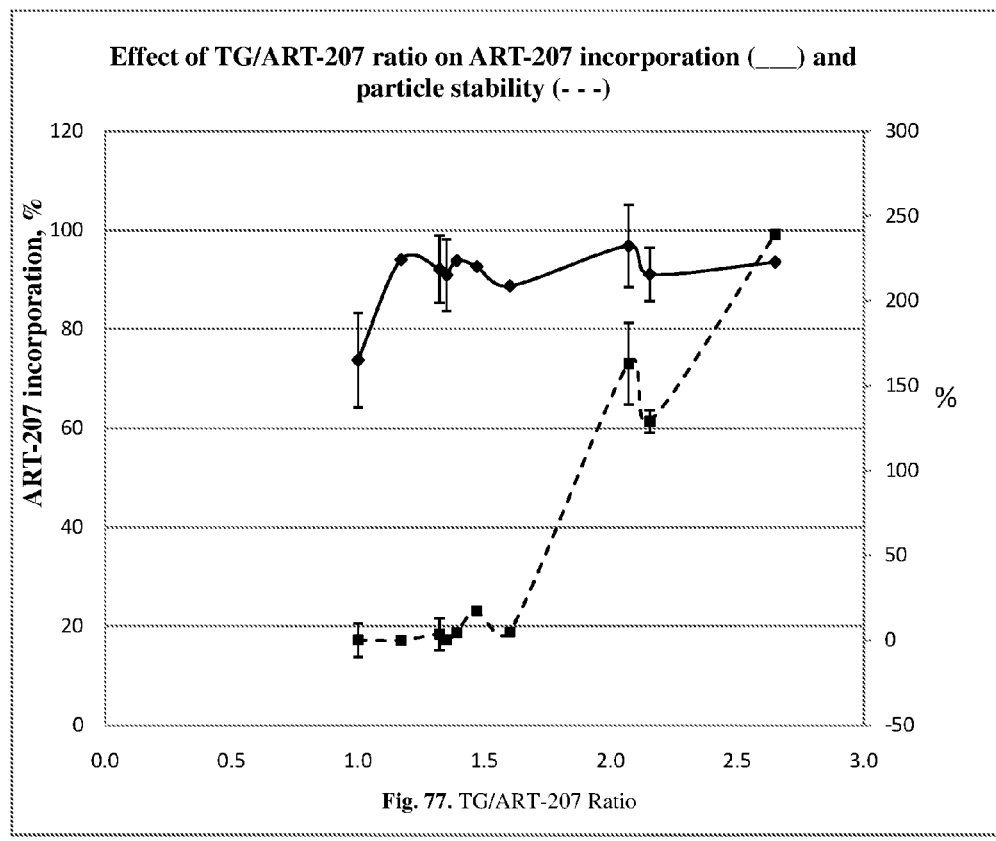

Figure 78: Dependence of particle size and stability on processing temperatures
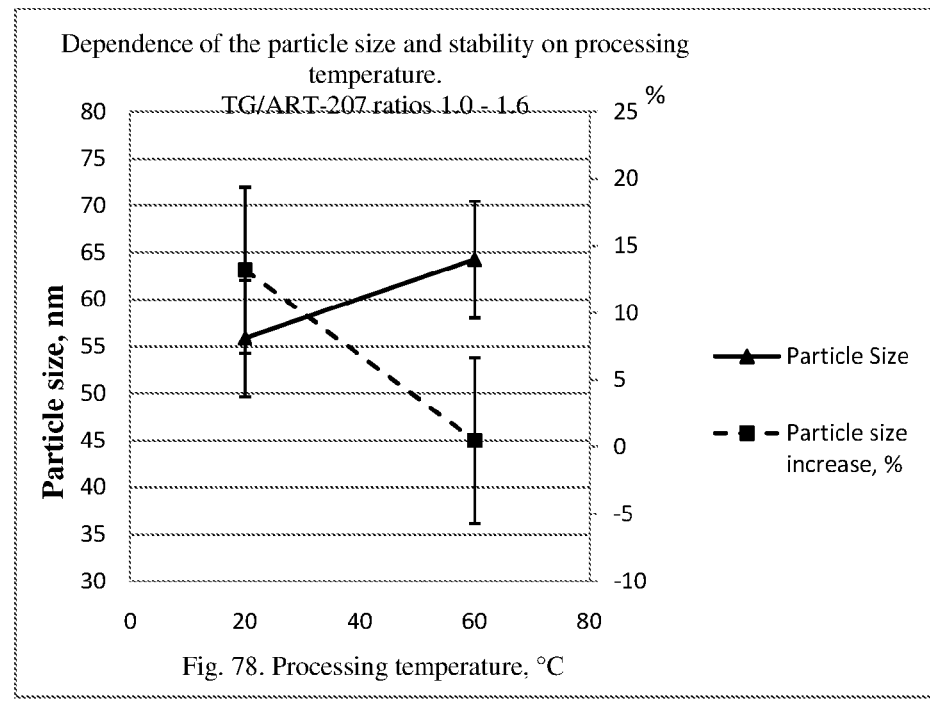
Figure 79: Representative graph showing particle size on processing time and temperature
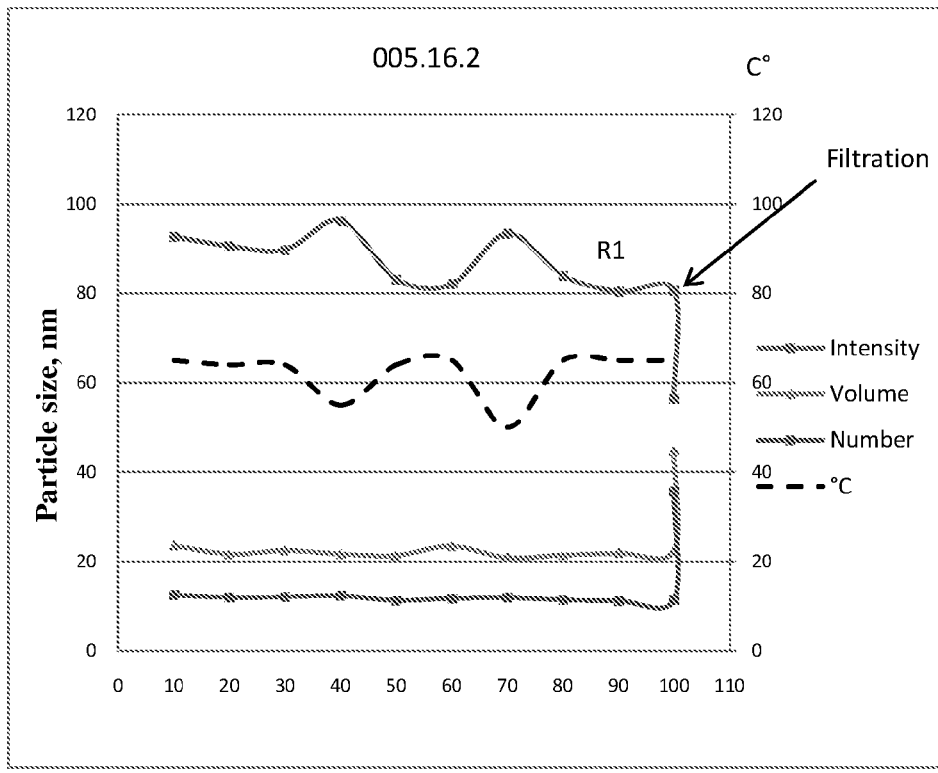

Figure 80: Representative graph showing particle size and stability of ART-287 containing formulation with time in days.
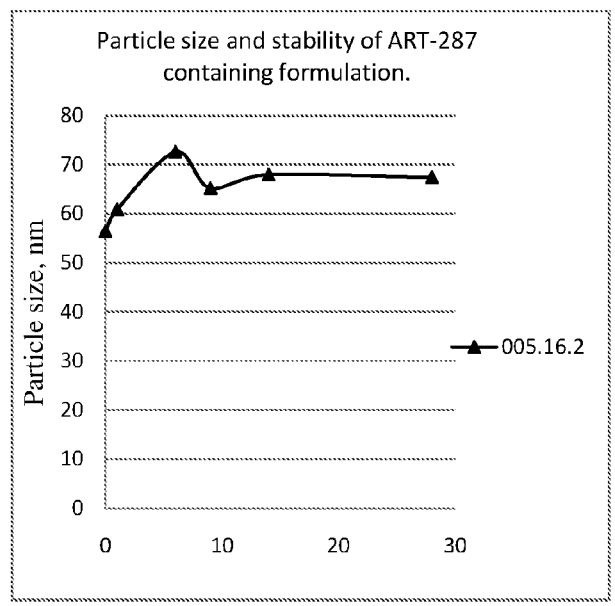
Figure 81: Representative graph showing particle size and temperature with time in minutes
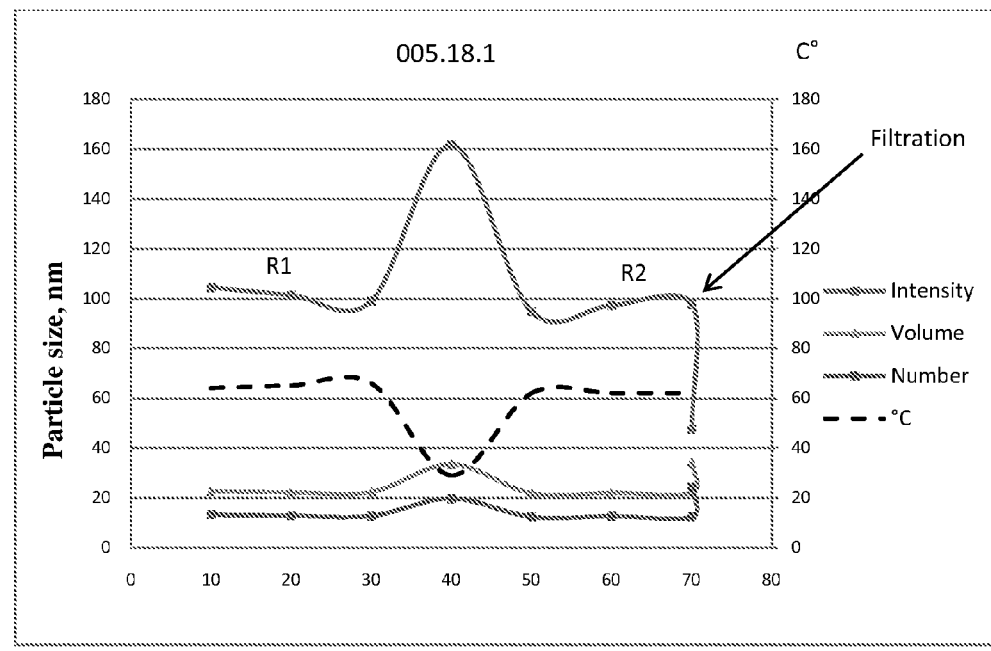

Figure 82: Representative graph showing particle size and stability of ART-287 containing formulation with time in days.
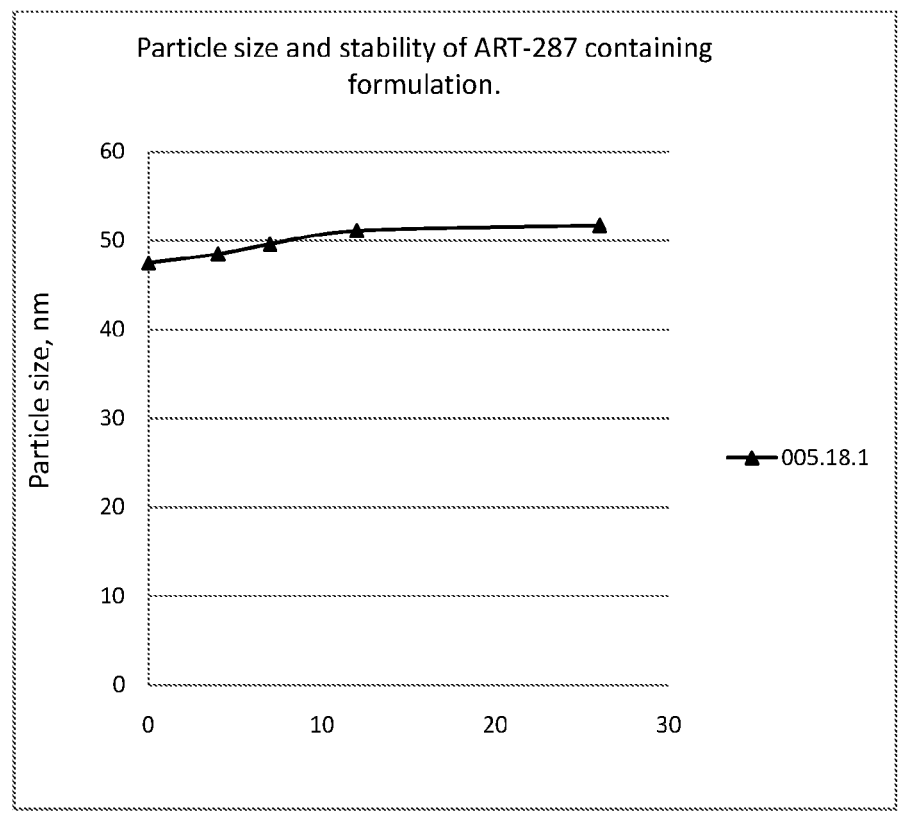

Acid Labile Lipophilic Molecular Conjugates

ART 449; ART 448; ART 473; ART 471; ART 472; ART 470; ART 489;

ART 488; ART 467; ART 332 and ART 441.

wherein -ALL$^1$, -ALL$^2$, -ALL$^3$ and -ALL$^4$ are each independently hydrogen or an acid labile lipophilic group, provided that at least one of -ALL$^1$, -ALL$^2$, -ALL$^3$ and -ALL$^4$ is an acid labile lipophilic group.

Acid Labile Lipophilic Molecular Conjugates

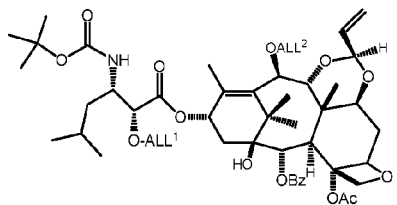

ALLMC of a 10-beta-taxane analog (19a)

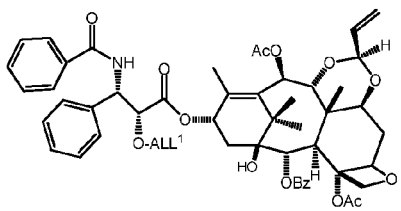

ALLMC of a 10-beta taxane analog (19b)

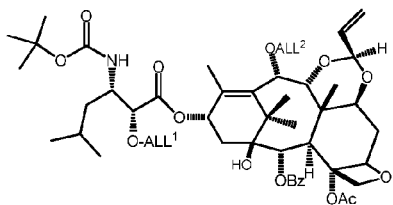

ALLMC of a 10-alpha taxane analog (19c)

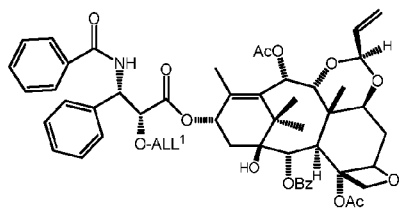

ALLMC of a 10-alpha analog (19d)

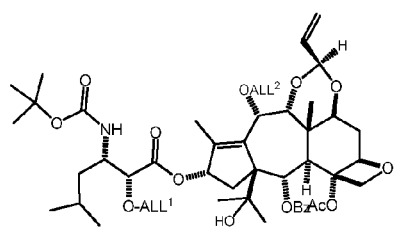

ALLMC of a 10-alpha abeo-taxane analog (19e)

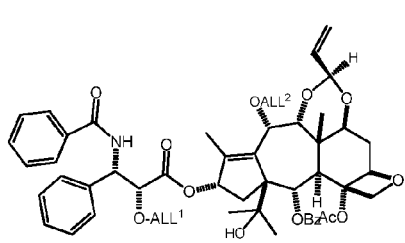

ALLMC of a 10-alpha abeo-taxane analog (19f)

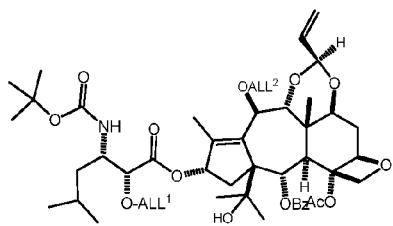

ALLMC of a 10-beta abeo-taxane analog (19g)

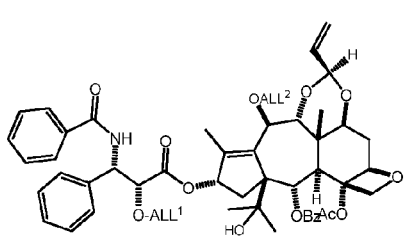

ALLMC of a 10-beta abeo-taxane analog (19h)

wherein -ALL$^1$, -ALL$^2$, -ALL$^3$ and –ALL$^4$ are each independently hydrogen or an acid labile lipophilic group, provided that at least one of -ALL$^1$, -ALL$^2$, -ALL$^3$ and –ALL$^4$ is an acid labile lipophilic group.

Figure 84

Acid Labile Lipophilic Molecular Conjugates wherein -ALL$^1$, -ALL$^2$, -ALL$^3$ and –ALL$^4$ are each independently hydrogen or an acid labile lipophilic group, provided that at least one of -ALL$^1$, -ALL$^2$, -ALL$^3$ and –ALL$^4$ is an acid labile lipophilic group.

NANOPARTICULATE COMPOSITIONS FOR TARGETED DELIVERY OF ACID LABILE, LIPOPHILIC PRODRUGS OF CANCER CHEMOTHERAPEUTICS AND THEIR PREPARATION

RELATED APPLICATION

This application is a Divisional of U.S. Non-Provisional application Ser. No. 14/485,713, filed Sep. 13, 2014, granted on Jun. 7, 2016, which claims the benefit of U.S. Provisional Application No. 61/877,521 filed Sep. 13, 2013.

SUMMARY

The present invention describes compositions and processes used to create structured submicron particles (nanoparticles) suitable for drug delivery. The structure of the particles prepared according to the methods disclosed herein results in desirable biological and physical performance. In one aspect, the structure of the particles is determined by the selection of the formulation components and of the processing steps used to create the particles. Structural elements that determine particle performance include particle size (and size distribution in the population), particle shape, particle charge and the distribution of individual components in the particle, especially those at the particle surface.

Particle Performance

Nanoparticles have particular advantages in parenteral drug delivery. Nanoparticles are smaller than blood cells and can be suspended and transported by the blood to various tissues of the body. Because they are smaller than microbes, they will pass through filters used to terminally sterilize parenteral products. Since the rapidly expanding vasculature of tumors is inherently leaky, nanoparticles leave the capillaries and are trapped in the poorly flushed extracellular space of tumors.

The nanoparticles included in the present application have unique biological performance. In one aspect, the nanoparticles of the present application are referred to as synthetic low density lipoprotein (LDL) nanoparticle, LDL-like nanoparticles or lipid emulsion (LDE), in part because the nanoparticles are prepared without any protein. Upon administration, these particles are not recognized as foreign, i.e., they are not coated with proteins which trigger clearance processes in the tissues of the reticuloendothelial system. Moreover, these particles were coated with a component that inhibits opsonization and phagocytosis. In fact, these particles are recognized as endogenous constituents and receive a coat of apo proteins that are recognized by receptors expressed on the surface of cells in need of cholesterol. After coating, these particles are preferentially taken up by lipoprotein receptor mediated endocytosis by cells with high cholesterol need. Such cells include those of rapidly dividing tissues, especially solid and liquid tumor tissue.

In one embodiment, the structured nanoparticles of the present application are designed to carry a useful drug load in a parenterally administered drug product. Drugs of particular interest with respect to this delivery system are those drugs which have low or extremely low solubility in water due to high lipophilicity. In one embodiment, drugs to be delivered which are not sufficiently lipophilic to be suitable for delivery in the nanoparticles of the present application may be made suitable by formation of highly lipophilic derivatives which can serve as pro-drugs of the drugs to be delivered. These particles are designed to be sufficiently chemically and physically stable in a manufactured drug product to allow a commercially adequate shelf life.

Requisite Particle Characteristics:

In one aspect, the advantageous disposition of these particles may be attributed to the particle's size, shape, composition and charge. In one aspect, the particles may be substantially spherical to move smoothly through the capillaries and may have a narrow size distribution with a mean of 60 nm. In one aspect, the size distribution range is about 40 to 80 nm. The composition may include cholesterol, other lipids and surface-active agents with or without the addition of polymers used to define particle structure. In one embodiment, a positive surface charge is achieved with the use of cationic surface active agents. A fundamental characteristic of small particles creates inherent instability. As particle size goes down, the interfacial area per unit mass of the dispersed system increases, and so does interfacial energy. This increased energy will tend to drive the particles to coalesce, forming larger particles with lower total energy.

Extreme particle size reduction can result in significant increases in drug solubility. Materials in a nanoparticle have a much higher tendency to leave the particle and go into the surrounding solution than those in a larger particle of the same composition. This phenomenon can increase the availability of drug for transport across a biological membrane, but it can also create physical instability of the nanoparticle itself. This instability is seen in Ostwald ripening in which small particles disappear as material is transferred to large particles. The physical stability of nanoparticles may be improved by the use of appropriate surface active agents and excipients at the right levels to reduce the interfacial energy, controlling the surface charge of the particles to maintain the dispersion, and manufacturing the particles in a narrow size distribution to reduce Ostwald ripening.

In one embodiment, the high drug load in the particles of the present application is achieved by creating a particle core of lipophilic inactive components which will dissolve the drug or its lipophilic pro-drug and reduce its tendency to leave the nanoparticle until it is released intracellularly at the target site.

Particle Production:

Very significant challenges are presented in the creation of particles with the proper size, structure, charge and stability. Homogeneous nanoparticles can be created by either precipitation of nanoparticle material from solution; or reducing the size of larger particles. Heterogeneous structured nanoparticles are not easily made by precipitation techniques because of the improbability of a single physical system precipitating all of the components into the requisite structure.

Particle size reduction requires energy; this energy is necessary to disrupt the forces holding the molecules of bulk components together and to increase the interfacial contact area between the particle and the surrounding medium. The energy must come from the process used to create the nanoparticles. To be useful, any process for the production of nanoparticles by size reduction, i.e., the system for imparting energy to the bulk formulation, must be controllable and scalable. Techniques demonstrated to be useful in nanoparticle production include ultrasonication and high-pressure homogenization. Ultrasonic energy, in the form of mechanical oscillations at greater than 20,000 Hz, has been used to reduce particle size in fluids. The high-frequency mechanical oscillations in the fluid cause the rapid formation and collapse of microscopic vacuum bubbles (cavitation). The high-velocity local mass transfer in this process imparts extremely high shear on the fluid and on suspended particles.

High shear can also be generated in flowing systems by forcing fluids at very high-pressure through an orifice or into a very narrow passage. Different processing equipment are known in the art and are available which uses either ultrasonication and or high-pressure homogenization working on a flowing stream of process fluid with sufficient control parameters to optimize the process.

Synthetic LDL Nanoparticles (sLDL):

In one embodiment, the invention provides for synthetic LDL nanoparticles comprising a lipid composition sufficiently similar to the normal human LDL particle composition to be recognized by the body as "natural". By being recognized by the body as "natural" these synthetic LDL nanoparticles become effective for selective delivery of lipophilic drugs or prodrugs to LDL receptor expressing tissues, especially tumor tissues which overexpess LDL receptors. The synthetic LDL nanoparticles are produced as described herein or may be made by methods known to those of skill in the art. As used herein, "synthetic" means made by chemical synthesis.

In one embodiment, the mean LDL nanoparticle size is 60 nm, but can be 40 nm to 100 nm. In some embodiments, the LDL nanoparticle is between 50 nm to 60 nm in size. The drugs or pro-drugs to be delivered can be complexed with microemulsions of a particular weight ratio of phospholipids (PL), triglyceride (TG) and cholesteryl ester (CE). In one embodiment the PL:TG:CE ratio is 36:5:1. In some embodiments, the phospholipid is egg yolk phosphatidylcholine (PC) or 1,2-dimyristoyl-sn-glycero-3-phosphorylcholine (DMPC). Suitable triglycerides that can be used include but are not limited to, soybean oil (SO), triolein (TO) and tripalmitate, and mixtures thereof. Suitable cholesteryl esters that can be used include but are not limited to, cholesteryl oleate (CO) or cholesteryl palmitate (CP), or mixtures thereof. In another embodiment, the composition of the core lipids, CE and TG are altered in order to alter the size of the emulsion. In another embodiment, the ratio of lipids is 30:6:1 weight ratio of PL:TG:CE. Other ratios that can be used include PL:TG:CE of 37:7:1 and PL:TG:CE of 20:3:0.5. In some embodiments, the cholesteryl ester is omitted from the microemulsion. In some embodiments the drugs or pro-drugs can be complexed with microemulsions of PL and TG in the ratio of 7:1.

The microemulsions can be made by extrusion of the lipids through a nanometer filter, such as a 30 nm filter. For example, the lipids are sonicated at 40° C. in the presence of 20 μM BHT and $N_2$ for sufficient time (e.g., about 1 hour), then extruded through a filter or a series of filters to obtain lipid particles having a suitable size. In one embodiment, the microemulsion is extruded through a 0.1 μm (100 nm) filter, then a 0.03 μm (30 nm) filter and isolated. In another embodiment, the composition can be made using a microfluidizer apparatus.

BACKGROUND

Targeted cancer therapies that can selectively kill cancer cells without harming other cells in the body would represent a major improvement in the clinical treatment of cancer. It would be highly desirable to develop a strategy to directly target cancer cells with chemotherapeutic agents in cancer treatment regimens. This could lead to reduction or elimination of toxic side effects, more efficient delivery of the drug to the targeted site, and reduction in dosage of the administered drug and a resulting decrease in toxicity to healthy cells and in the cost of the chemotherapeutic regimen. Reports of targeting chemotherapeutic drugs using antibodies have appeared in the literature since 1958. Targeting drugs by conjugation to antibodies for selective delivery to cancer cells has had limited success due to the large size of antibodies (MW=125-150 kilodaltons or KD) and thus their relative inability to penetrate solid tumors. An alternative strategy comprises the use of smaller targeting ligands and peptides, which recognize specific receptors unique to or overexpressed on tumor cells, as the targeting vector. Such constructs have molecular weights of 2-6 KD, which allow ready penetration throughout solid tumors.

Increased cell proliferation and growth is a trademark of cancer. The increase in cellular proliferation is associated with high turnover of cell cholesterol. Cells requiring cholesterol for membrane synthesis and growth may acquire cholesterol by receptor mediated endocytosis of plasma low density lipoproteins (LDL), the major transporter of cholesterol in the blood, or by de novo synthesis. LDL is taken up into cells by a receptor known as the LDL receptor (LDLR); the LDL along with the receptor is endocytosed and transported into the cells in endosomes. The endosomes become acidified and this releases the LDL receptor from the LDL; the LDL receptor recycles to the surface where it can participate in additional uptake of LDL particles. There is a body of evidence that suggests that tumors in a variety of tissues have a high requirement for LDL to the extent that plasma LDLs are depleted. The increased import of LDL into cancerous cells is thought to be due to elevated LDL receptors (LDLR) in these tumors. Some tumors known to express high numbers of LDLRs include some forms of leukemia, lung tumors, colorectal tumors and ovarian cancer. In vivo studies showed that LDLRs do appear in brain malignancies. Leppala et al used PET imaging, and demonstrated that 99mTc_LDL localizes in human brain tumors in vivo but not in normal brain.

This suggests that the LDL receptor is a potential unique molecular target in GBM and other malignancies for the delivery of anti-tumor drugs via LDL particles. A test of this possibility was undertaken by Maranhão and coworkers. A protein-free microemulsion (LDE) with a lipid composition resembling that of low-density lipoprotein (LDL) was used in metabolic studies in rats to compare LDE with the native lipoprotein. Incubation studies also showed that LDE incorporates a variety of apolipoproteins, including apo E, a ligand for recognition of lipoproteins by specific receptors.

Lipophilic Derivatives of Cancer Chemotherapeutic Agents:

Arbor Therapeutics has developed unique lipophilic derivatives of the cancer chemotherapeutic agent which have high stability in normal systemic circulation and retention in the lipid core of the LDL particles but readily release the active chemotherapeutic agent in the acidic environment of the endosome. See U.S. Pat. No. 8,440,714, the disclosure of which is incorporated herein in its entirety.

In another embodiment, there is provided a active chemotherapeutic compounds of the formula 3a or 3b:

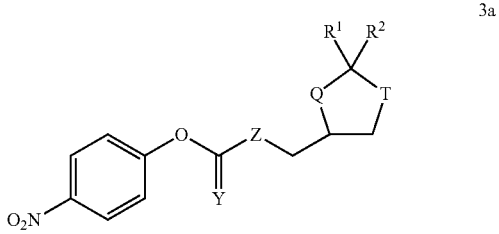

3a

-continued

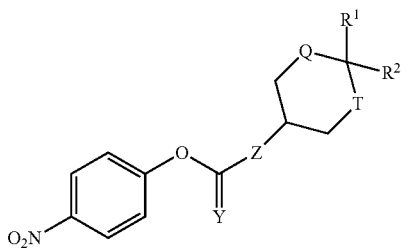

3b wherein: $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is selected from O or S; Q is O or S; and T is O or S. In one aspect of the compound, $R^1$ is hydrogen or $C_1$-$C_4$ alkyl; $R^2$ is $C_5$-$C_{22}$ alkyl; Y is O or S; Z is O; Q is O; and T is O. The activated compound of the formula 3a or 3b may be used to prepare the acid labile lipophilic conjugate when the activated compound is condensed with a hydroxyl bearing cancer chemotherapeutic agent (HBCCA). As defined herein, the HBCCA is represented generically with the residue or group "R" in the formulae 1, 1a, 1b, 1.1, 2 and 2a, for example, and where the HBCCA is not coupled to form the acid labile, lipophilic molecular conjugates, then the HBCCA may also be generically represented as having the formula "R—OH" since the HBCCA may be functionalized by one or more hydroxyl (—OH) groups.

In one embodiment, there is provided an acid labile lipophilic molecular conjugate (ALLMC) of the formula 1, 1.1 or formula 2:

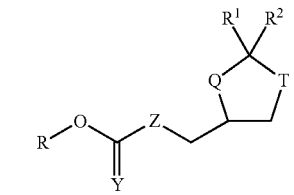

1

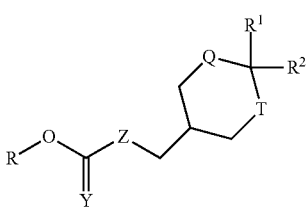

1.1

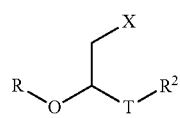

2 wherein: R is a hydroxyl bearing cancer chemotherapeutic agent; for formula 1 or 1.1 $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is O or S; Q is O or S; and T is O or S; for formula 2: $R^2$ is a $C_1$-$C_{22}$ alkyl; T is O or S; and X is hydrogen or a leaving group selected from the group consisting of mesylates, sulfonates and halogen (Cl, Br and I); and their isolated enantiomers, diastereoisomers or mixtures thereof, or a pharmaceutically acceptable salt thereof. The compound 1.1 includes the pure syn isomer, the pure anti isomer and mixtures of syn- and anti-isomers, and their diastereomers.

In another embodiment, there is provided the above acid labile lipophilic molecular conjugate of the formula 1 or 1.1 wherein: R is a hydroxyl bearing cancer chemotherapeutic agent; $R^1$ is hydrogen, $C_1$-$C_4$ alkyl or $C_5$-$C_{22}$ alkyl; $R^2$ is $C_5$-$C_{22}$ alkyl; Y is O or S; Z is O; Q is O; and T is O. In one aspect of the acid labile lipophilic molecular conjugate of the formula 2 wherein: $R^2$ is $C_5$-$C_{22}$ alkyl; T is O; and X is hydrogen or selected from the group consisting of Cl, Br and I. In another variation, $R^2$ is $C_9$-$C_{22}$. In another aspect of the above acid labile lipophilic molecular conjugate comprising the formula 1a, 1b or formula 2a:

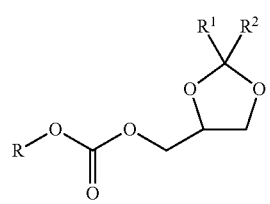

1a

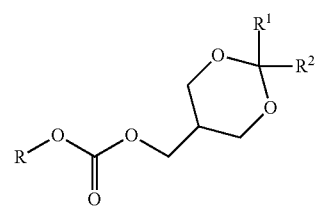

1b

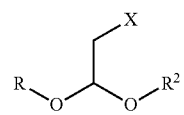

2a wherein: R is a hydroxyl bearing cancer chemotherapeutic agent (HBCCA); for formula 1a or 1b $R^1$ is hydrogen, $C_1$-$C_4$ alkyl or $C_5$-$C_{22}$ alkyl; and $R^2$ is $C_5$-$C_{22}$ alkyl; and for formula 2a: $R^2$ is $C_1$-$C_{22}$ alkyl; and X is hydrogen or is selected from the group consisting of Cl, Br and I. In one variation of the compound that is the carbonate (i.e., —OC(O)O—) of the formula 1a or 1b the compound is the corresponding sulfonate (i.e., —OS(O)O—) of the formula 1a wherein the carbonate group is replaced by a sulfonate group. The compound 1b includes the pure syn isomer, the pure anti isomer and mixtures of syn and anti isomers, and their diastereomers.

In another variation of the compound of the formula 1, 2, 1a and 2a, $R^1$ is hydrogen or $C_1$-$C_4$ alkyl or $C_5$-$C_{22}$ alkyl, and $R^2$ is the carbon residue of an unsaturated fatty acid, such as the carbon residue selected from the group consisting of the $C_{19}$ residue of eicosenoic acid (including the cis isomer, trans isomer and mixtures of isomers), $C_{17}$ residue of oleic acid and the $C_{17}$ residue of elaidic acid. As used herein, the "carbon residue" (e.g., $C_{17}$ residue, $C_{19}$ residue etc. . . . ) of the fatty acid means the carbon chain of the fatty acids excluding the carboxyl carbon.

In another aspect of the above acid labile lipophilic molecular conjugate, the hydroxyl bearing cancer chemotherapeutic agent is selected from the group consisting of taxanes, abeo-taxanes, camptothecins, epothilones, cucurbitacins, quassinoids, anthracyclines, and their analogs and derivatives. In another aspect of the above acid labile lipophilic molecular conjugate, the hydroxyl bearing cancer chemotherapeutic agent is selected from the group consisting of aclarubicin, camptothecin, masoprocol, paclitaxel, pentostatin, amrubicin, cladribine, cytarabine, docetaxel, gemcitabine, elliptinium acetate, epirubicin, etoposide, formestane, fulvestrant, idarubicin, pirarubicin, topotecan, valrubicin and vinblastine.

In one embodiment, there is provided an acid labile lipophilic molecular conjugate (ALLMC) of the formula 1, 1.1 or formula 2:

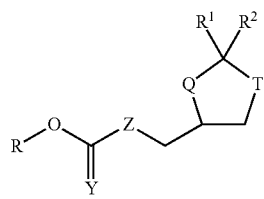

1

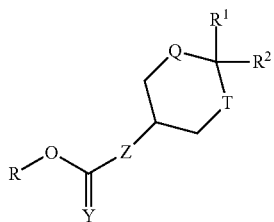

1.1

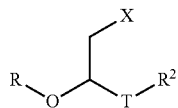

2 wherein: R is a hydroxyl bearing cancer chemotherapeutic agent; for formula 1 or 1.1 $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is O or S; Q is O or S; and T is O or S; for formula 2: $R^2$ is a $C_1$-$C_{22}$ alkyl; T is O or S; and X is hydrogen or a leaving group selected from the group consisting of mesylates, sulfonates and halogen (Cl, Br and I); and their isolated enantiomers, diastereoisomers or mixtures thereof, or a pharmaceutically acceptable salt thereof. The compound 1.1 includes the pure syn isomer, the pure anti isomer and mixtures of syn- and anti-isomers, and their diastereomers.

In another embodiment, there is provided the above acid labile lipophilic molecular conjugate of the formula 1 or 1.1 wherein: R is a hydroxyl bearing cancer chemotherapeutic agent; $R^1$ is hydrogen, $C_1$-$C_4$ alkyl or $C_5$-$C_{22}$ alkyl; $R^2$ is $C_5$-$C_{22}$ alkyl; Y is O or S; Z is O; Q is O; and T is O. In one aspect of the acid labile lipophilic molecular conjugate of the formula 2 wherein: $R^2$ is $C_5$-$C_{22}$ alkyl; T is O; and X is hydrogen or selected from the group consisting of Cl, Br and I. In another variation, $R^2$ is $C_9$-$C_{22}$. In another aspect of the above acid labile lipophilic molecular conjugate comprising the formula 1a, 1b or formula 2a:

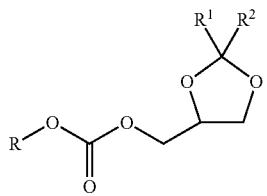

1a

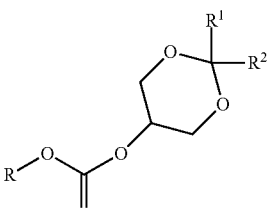

1b

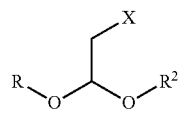

2a wherein: R is a hydroxyl bearing cancer chemotherapeutic agent (HBCCA);
for formula 1a or 1b $R^1$ is hydrogen, $C_1$-$C_4$ alkyl or $C_5$-$C_{22}$ alkyl; and $R^2$ is $C_5$-$C_{22}$ alkyl; and for formula 2a: $R^2$ is $C_1$-$C_{22}$ alkyl; and X is hydrogen or is selected from the group consisting of Cl, Br and I. In one variation of the compound that is the carbonate (i.e., —OC(O)O—) of the formula 1a or 1b the compound is the corresponding sulfonate (i.e., —OS(O)O—) of the formula 1a wherein the carbonate group is replaced by a sulfonate group. The compound 1b includes the pure syn isomer, the pure anti isomer and mixtures of syn and anti isomers, and their diastereomers.

In another variation of the compound of the formula 1, 2, 1a and 2a, $R^1$ is hydrogen or $C_1$-$C_4$ alkyl or $C_5$-$C_{22}$ alkyl, and $R^2$ is the carbon residue of an unsaturated fatty acid, such as the carbon residue selected from the group consisting of the $C_{19}$ residue of eicosenoic acid (including the cis isomer, trans isomer and mixtures of isomers), $C_{17}$ residue of oleic acid and the $C_{17}$ residue of elaidic acid. As used herein, the "carbon residue" (e.g., $C_{17}$ residue, $C_{19}$ residue etc. . . . ) of the fatty acid means the carbon chain of the fatty acids excluding the carboxyl carbon. In another aspect of the above acid labile lipophilic molecular conjugate, the hydroxyl bearing cancer chemotherapeutic agent is selected from the group consisting of taxanes, abeo-taxanes, camptothecins, epothilones, cucurbitacins, quassinoids, anthracyclines, and their analogs and derivatives. In another aspect of the above acid labile lipophilic molecular conjugate, the hydroxyl bearing cancer chemotherapeutic agent is selected from the group consisting of aclarubicin, camptothecin, masoprocol, paclitaxel, pentostatin, amrubicin, cladribine, cytarabine, docetaxel, gemcitabine, elliptinium acetate, epirubicin, etoposide, formestane, fulvestrant, idarubicin, pirarubicin, topotecan, valrubicin and vinblastine. In another aspect of the above acid labile lipophilic molecular conjugate, the conjugate is selected from the compounds in FIGS. 18, 19 and 20. In one variation, only one of the groups -ALL$^1$, -ALL$^2$, -ALL$^3$ . . . to -ALL$^n$ is an -ALL group and the others are hydrogens. In another variation, two of the groups -ALL$^1$, -ALL$^2$, -ALL$^3$ . . . to -ALL$^n$ are -ALL groups.

In another embodiment, there is provided a pharmaceutical composition comprising: a) a therapeutically effective amount of a compound of the above, in the form of a single diastereoisomer; and b) a pharmaceutically acceptable excipient. In another aspect, the pharmaceutical composition is adapted for oral administration; or as a liquid formulation adapted for parenteral administration. In another aspect, the composition is adapted for administration by a route selected from the group consisting of orally, parenterally, intraperitoneally, intravenously, intraarteriall, transdermally, intramuscularly, rectally, intranasally, liposomally, subcutaneously and intrathecally. In another embodiment, there is provided a method for the treatment of cancer in a patient comprising administering to the patient a therapeutically effective amount of a compound or composition of any of the above compound or composition, to a patient in need of such treatment. In one aspect of the method, the cancer is selected from the group consisting of leukemia, neuroblastoma, glioblastoma, cervical, colorectal, pancreatic, renal and melanoma. In another aspect of the method, the cancer is selected from the group consisting of lung, breast, prostate, ovarian and head and neck. In another aspect of the method, the method provides at least a 10%, 20%, 30%, 40%, or at least a 50% diminished degree of resistance expressed by the cancer cells when compared with the non-conjugated hydroxyl bearing cancer chemotherapeutic agent.

In another embodiment, there is provided a method for reducing or substantially eliminating the side effects of chemotherapy associated with the administration of a cancer chemotherapeutic agent to a patient, the method comprising administering to the patient a therapeutically effective amount of an acid labile lipophilic molecular conjugate of the formula 1, 1.1 or formula 2:

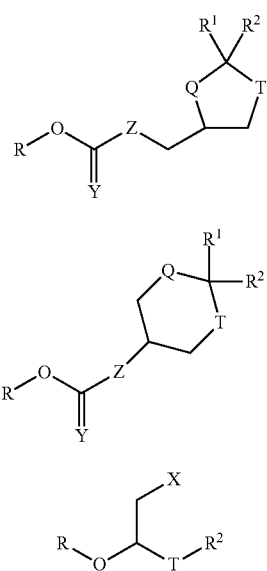

wherein: R is a hydroxyl bearing cancer chemotherapeutic agent; for formula 1 or 1.1: $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is O or S; Q is O or S; and T is O or S; for formula 2: $R^2$ is $C_1$-$C_{22}$ alkyl; T is O or S; and X is hydrogen or a leaving group selected from the group consisting of mesylates, sulfonates and halogen (Cl, Br and I); and their isolated enantiomers, diastereoisomers or mixtures thereof. The compound 1.1 includes the pure syn isomer, the pure anti isomer and mixtures of syn and anti isomers, and their diastereomers. In one variation of the above, $R^2$ is $C_9$-$C_{22}$ alkyl. In one aspect, the method provides a higher concentration of the cancer chemotherapeutic agent in a cancer cell of the patient. In another aspect, the method delivers a higher concentration of the cancer chemotherapeutic agent in the cancer cell, when compared to the administration of a non-conjugated cancer chemotherapeutic agent to the patient, by at least 5%, 10%, 20%, 30%, 40% or at least 50%.

In another embodiment, there is provided a compound of the formula 3a or 3b:

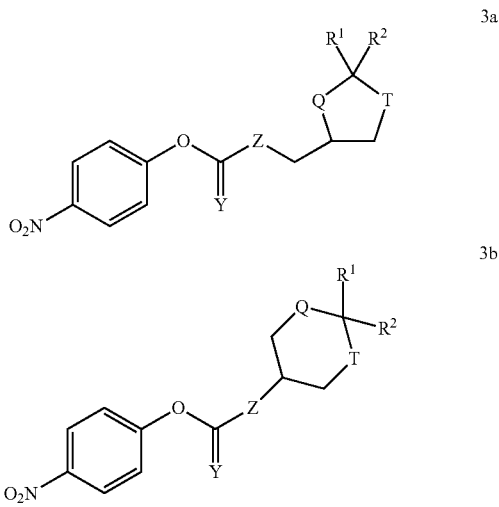

wherein: $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is selected from O or S; Q is O or S; and T is O or S. In one aspect of the compound, $R^1$ is hydrogen or $C_1$-$C_4$ alkyl; $R^2$ is $C_5$-$C_{22}$ alkyl; Y is O or S; Z is O; Q is O; and T is O. The activated compound of the formula 3a or 3b may be used to prepare the acid labile lipophilic conjugate when the activated compound is condensed with a hydroxyl bearing cancer chemotherapeutic agent (HBCCA). As defined herein, the HBCCA is represented generically with the residue or group "R" in the formulae 1, 1a, 1b, 1.1, 2 and 2a, for example, and where the HBCCA is not coupled to form the acid labile, lipophilic molecular conjugates, then the HBCCA may also be represented as having the formula "R—OH" since the HBCCA may be functionalized by one or more hydroxyl (—OH) groups.

Similarly, the acid labile lipophilic group (i.e., the "-ALL" group of the activated compound) that may be condensed with a HBCCA to form the acid labile, lipophilic molecular conjugate generically represented as "R-O-ALL." Accordingly, where more than one -ALL group is condensed or conjugated with a HBCCA group, then each -ALL group may be independently designated as -ALL$^1$, -ALL$^2$, -ALL$^3$ ... to -ALL$^n$ where n is the number of available hydroxyl groups on the cancer chemotherapeutic agent that may be conjugated or couple with an -ALL group. As exemplified for the compound of formulae 1 and 2, for example, the HBCCA and the -ALL groups as designated, are shown below.

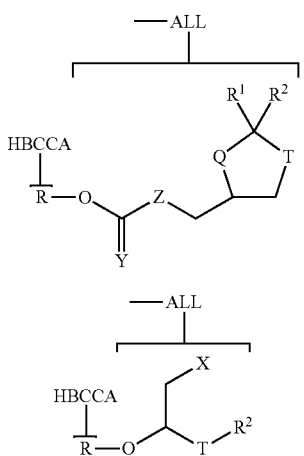

An example of an acid labile, lipophilic molecular conjugate (ALLMC), where the HBCCA group is paclitaxel having two -ALL groups, is depicted below:

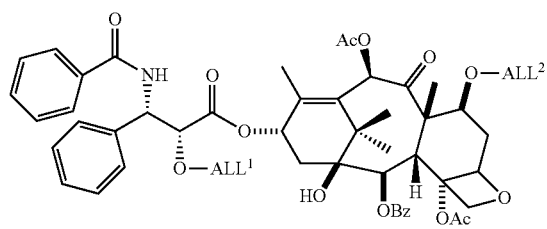

Acid Labile Lipophilic Molecular Conjugate of Paclitaxel

In the above representative example of the acid labile molecular conjugate of paclitaxel, each of the $-ALL^1$ and $-ALL^2$ is independently hydrogen or an -ALL group as defined herein. For HBCCA groups having more than one hydroxyl groups, the inaccessible hydroxyl group or groups where the acid labile lipophilic group cannot be formed, then the group that is designated as an -ALL group(s) is hydrogen.

In another aspect of the above acid labile lipophilic molecular conjugate, the hydroxyl bearing cancer chemotherapeutic agent is selected from the group consisting of taxanes, abeo-taxanes, camptothecins, epothilones, cucurbitacins, quassinoids, anthracyclines, and their analogs and derivatives. In another aspect of the above acid labile lipophilic molecular conjugate, the hydroxyl bearing cancer chemotherapeutic agent is selected from the group consisting of aclarubicin, camptothecin, masoprocol, paclitaxel, pentostatin, amrubicin, cladribine, cytarabine, docetaxel, gemcitabine, elliptinium acetate, epirubicin, etoposide, formestane, fulvestrant, idarubicin, pirarubicin, topotecan, valrubicin and vinblastine.

Representative chemotherapeutic agents that may be employed in the present composition or formulations are disclosed in Figures A, B and C. In one aspect of the above, the chemotherapeutic agent is ART-207.

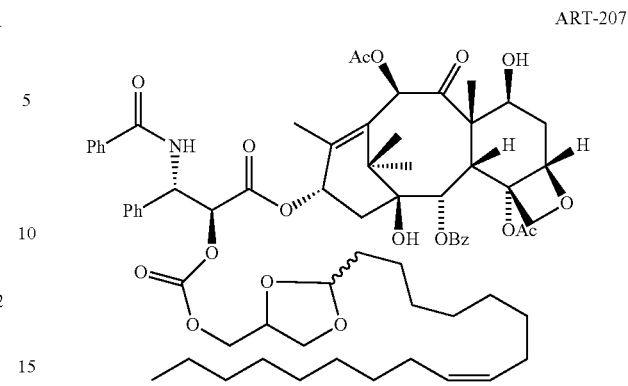

ART-207

Capturing the great potential of selective and specific delivery of chemotherapeutic compounds to cancer tissues via their over expression of LDL receptors and consequent high uptake of LDL particles from the systemic circulation, requires that the cancer chemotherapeutic agent have high lipophilicity so as to remain entrapped in the lipid core of the LDL particle and not diffuse into the plasma to lead to toxic side effects from exposure of normal tissues to the agent. Further, once the LDL particle with its chemotherapeutic payload has entered the cancer cell via LDL receptor mediated uptake into the acidic environment of the endosome, the LDL receptor is disassociated from the LDL particle and is recycled to the cell surface and the LDL particle releases its lipid contents and its lipophilic chemotherapeutic agent to the enzymes and acidic environment of the endosome.

Further validity of this expectation was shown by Maranhão and coworkers who demonstrated that a cholesterol-rich microemulsion or nanoparticle preparation (LDE) concentrates in cancer tissues after injection into the bloodstream. The cytotoxicity, pharmacokinetics, toxicity to animals and therapeutic action of a paclitaxel lipophilic derivative associated to LDE were compared with those of commercial paclitaxel. Results showed that LDE-paclitaxel oleate was stable. The cytostatic activity of the drug in the complex was diminished compared with the commercial paclitaxel due to the cytotoxicity of the vehicle Cremophor EL used in the commercial formulation. Competition experiments in neoplastic cultured cells showed that paclitaxel oleate and LDE are internalized together by the LDL receptor pathway. Tolerability to mice was remarkable, such that the lethal dose ($LD_{50}$) was nine fold greater than that of the commercial formulation (LD50=326 µM and 37 µM, respectively). LDE concentrates paclitaxel oleate in the tumor roughly fourfold relative to the normal adjacent tissues. At equimolar doses, the association of paclitaxel oleate with LDE resulted in remarkable changes in the drug pharmacokinetic parameters when compared to commercial paclitaxel ($t_{1/2}$=218 mm and 184 mM, AUC=1,334 µg-h/mL and 707 µg-h/mL and CL=0.125 mL/min and 0.236 mL/min, respectively). The therapeutic efficacy of the complex was pronouncedly greater than that of the commercial paclitaxel, as indicated by the reduction in tumor growth, increase in survival rates and % cure of treated mice. Maranhão et al showed LDE-paclitaxel oleate is a stable complex and compared with paclitaxel, toxicity is considerably reduced and activity is enhanced which may lead to improved therapeutic index in clinical use. Maranhão and coworkers followed up their preliminary animal studies with a pilot clinical study in breast cancer patients. The clinical study was performed in breast cancer patients to evaluate the tumoral uptake, pharmacokinetics and toxicity of paclitaxel associated to LDE nanoemulsions. Twenty-four hours before mastectomy $^3$H-paclitaxel oleate associated with $^{14}$C-cholesteryl oleate-nanoemulsion or $^3$H-paclitaxel in Cremophor EL were injected into five patients for collection of blood samples and fragments of tumor and normal breast tissue. A pilot clinical study of paclitaxel-nanoemulsion administered at 3-week intervals was performed in four breast cancer patients with refractory advanced disease at 175 and 220 mg/m$^2$ dose levels. The half-life ($t_{1/2}$) of paclitaxel oleate associated to the nanoemulsion was longer than that of paclitaxel ($t_{1/2}$=15.4±4.7 and 3.5±0.80 h, respectively). Uptake of the $^{14}$C-cholesteryl ester nanoemulsion and $^3$H-paclitaxel oleate by breast malignant tissue was threefold greater than the normal breast tissue and toxicity was minimal at the two dose levels. Their results suggest that the paclitaxel-nanoemulsion preparation can be advantageous for use in the treatment of breast cancer because the pharmacokinetic parameters are improved, the drug is concentrated in the neoplastic tissue and the toxicity of paclitaxel is reduced. Additional reports from the Maranhão laboratory of small human trials with the LDL-like lipid emulsion show that lipophilic drugs incorporated into the core of the emulsion are targeted to tumor tissue and side effects are significantly reduced. The difficulty of preparation of the emulsion, manufacture by long term sonication and extended centrifugation for particle size selection precluded them from further clinical exploration and development.

We have discovered how to prepare a nanoparticulate "pseudo LDL" lipid microemulsion as a delivery formulation for sufficiently lipophilic chemotherapeutics, including our unique acid labile, lipophilic prodrug derivative of the cancer chemotherapeutic agent. In one embodiment, the lipophilic chemotherapeutic agents have a measured or calculated LogP of greater than 4. We further demonstrate in animal tumor models that the acid labile, lipophilic molecular conjugates of cancer chemotherapeutic agent when dosed in a nanoparticulate, LDL-like lipid emulsion, is more useful for tumor reduction due to reduced toxicity and greater efficacy due to selective delivery to neoplastic/tumor tissue.

In one embodiment, the application discloses a stable, synthetic low density lipoprotein (LDL) nanoparticle comprising: a) a lipophilic anti-cancer agent; b) phospholipids (PL); and c) triglycerides (TG); wherein the LDL nanoparticle has a particle size less than 100 nm, less than 90 nm or less than 80 nm. As referred to herein, a stable synthetic low density lipoprotein (LDL) nanoparticle is a nanoparticle as defined herein that has a shelf life at about 25° C. of greater than 90 days, greater than 120 days, greater than 180 days, or greater than 1 year when stored in a sealed container and away from exposure to light. In another aspect, the nanoparticle has a shelf life at about 25° C. that is more than 1 year, or about 2 years or more when stored in a sealed container and away from exposure to light. In one aspect if the LDL nanoparticle, the particle size distribution is between 40 to 80 nm. In another aspect, the particle size distribution is between 50 and 60 nm. In one aspect of the above, the LDL nanoparticle has a mean size distribution of 60 nm. In another aspect, the LDL nanoparticle has a mean size distribution of about 50 nm. In another aspect, the phospholipids is selected from the group consisting of phosphotidylcholine, phosphotidylethanolamine, symmetric or asymmetric 1,2-diacyl-sn-glycero-3-phosphorylcholines, 1,2-dimyristoyl-sn-glycero-3-phosphorylcholine,1,2-dimyristoyl-sn-glycero-3-phosphorylethanolamine, egg phospholipids, egg phosphatidyl glycerol, dipalmitoylphosphatidylglycerol, egg lecithin, soy lecithin, lecithin (NOS) and mixtures thereof.

In another aspect, the LDL nanoparticle further comprises cholesterol ester (CE) or cholesterol (C), or mixtures of cholesterol ester and cholesterol. In another aspect, the cholesterol ester is selected from the group consisting of $C_{16-22}$ esters of cholesterol, cholesterol and mixtures thereof; and the triglycerides is selected from the group consisting of soybean oil, triolein, glyceryl tripalmitate and mixtures thereof. In one aspect of the above, the esters of cholesterol is selected from the group consisting of cholesteryl oleate, cholesteryl palmatate, cholesteryl stearate and cholesteryl lenolenate. In another aspect, the LDL nanoparticle further comprises an agent selected from the group consisting of triolein, natural antioxidants, BHT, ubiquinol, ubiquinol 10, vitamin E, alpha-tocopherol, gamma-tocopherol, lycopene, retinyl derivative and betacarotene, or mixtures thereof. In another aspect, the lipophilic anti-cancer agent is an anti-cancer agent or a prodrug of the anti-cancer agent. In one aspect of the above, the ratio of PL:TG may range from 8:1 to 3:1. In another aspect, the ratio of PL:TG:CE may range from 8:1:0.5 to 3:1:0.1. In another aspect, the ratio of the lipophilic anti-cancer agent: PL:TG may range from 1:10:3 to 1:3:0.5. In another aspect, the ratio of the lipophilic anti-cancer agent: PL:TG:CE may range from 1:10:3:1 to 1:3:0.5:0.1.

In another aspect, the anti-cancer agent is selected from the group consisting of a taxane, abeo-taxane, camptothecin, epothilone, cucurbitacin, quassinoid and an anthracycline. In another aspect, the anticancer agent is selected from the group consisting of aclarubicin, camptothecin, masoprocol, paclitaxel, pentostatin, amrubicin, cladribine, cytarabine, docetaxel, gemcitabine, elliptinium acetate, epirubicin, etoposide, formestane, fulvestrant, idarubicin, pirarubicin, topotecan, valrubicin and vinblastine. In yet another aspect, the pro-drug of the anti-cancer agent is an acid labile lipophilic molecular conjugates is as disclosed herein, and in Figures A, B and C. In one particular aspect, the acid labile lipophilic molecular conjugates is ART-207.

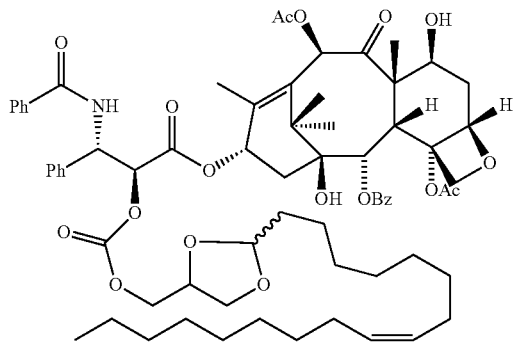

ART-207

In another aspect of the above, the lipophilic anti-cancer agent has a logP greater than 4.0, 6.0 or 8.0. In one aspect, the weight ratio of PL:TG:CE:C ranges from 73:12:2:1 to 78:12:2:1; optionally further comprising an additive selected from the group consisting of triolein, natural antioxidants, BHT, ubiquinol, ubiquinol 10, vitamin E, alpha-tocopherol, gamma-tocopherol, lycopene, retinyl derivative and betacarotene, or mixtures thereof. In one variation, the weight ratio of PL:TG:CE:C is 77:10:2:1. In one aspect, the natural antioxidant is selected from Coenzyme Q10, resveratrol, pterostilbene and mixtures thereof. In another aspect, the ratio of the lipophilic anti-cancer agent to the triglyceride is from 1:1 to 0.6:1. In another aspect, the LDL nanoparticle contains a total solids content of 6.0 to 8% wt/wt. In another aspect, the LDL nanoparticle contains a total lipid content of 5.0 to 7.0% wt/wt. In one variation, the LDL nanoparticle further comprises a poloxamer selected from the group consisting of P188, P237, P338, P407, SYNPERONICS, PLURONICS and KOLLIPHOR, or mixtures thereof.

In another embodiment, there is provided a process for preparing a stable, synthetic low density lipoprotein (LDL) nanoparticle comprising: a) a lipophilic anti-cancer agent; b) phospholipids (PL); and c) triglycerides (TG); the process comprising: 1) combining the lipophilic anti-cancer agent, phospholipids and triglycerides to form a mixture; 2) homogenizing the mixture by dissolution in a volatile solvent; 3) removing the solvent; 4) forming a coarse emulsion by blending of the mixture in a buffer to form an emulsion mixture; 5) microfluidizing the emulsion mixture in a microfluidizer apparatus for a sufficient amount of time to produce a particle preparation of 100 nm or less; and 6) sterilizing the nanoparticle preparation through a 0.22 micron filter to obtain the synthetic LDL nanoparticles with a range of 40 nm to 80 nm. In one variation, the synthetic low density lipoprotein (LDL) nanoparticle mixture wherein the phospholipids is selected from the group consisting of phosphotidylcholine, phosphotidylethanolamine, symmetric or asymmetric 1,2-diacyl-sn-glycero-3-phosphorylcholines, 1,2-dimyristoyl-sn-glycero-3-phosphorylcholine,1,2-dimyristoyl-sn-glycero-3-phosphorylethanolamine, egg phospholipids, egg phosphatidyl glycerol, dipalmitoylphosphatidylglycerol, egg lecithin, soy lecithin, lecithin (NOS) and mixtures thereof. In another aspect, the LDL nanoparticle further comprises cholesterol (C) or cholesterol ester (CE) selected from the group consisting of $C_{16-22}$ esters of cholesterol, cholesterol and mixtures thereof; and the triglycerides is selected from the group consisting of soybean oil, triolein, glyceryl tripalmitate and mixtures thereof; or mixtures of cholesterol and cholesterol esters. In one aspect of the above, the slow speed blending is performed at a speed of between 200 and 800 rpm, about 200 rpm, 400 rpm, 600 rpm or 800 rpm. In another aspect, the microfluidizing of the warm coarse emulsion mixture is performed at a processing temperature of about 45 to 65° C. In another aspect of the above process, the solvent is removed in vacuum. In another embodiment, there is provided a stable, synthetic low density lipoprotein (LDL) nanoparticle comprising: a) a lipophilic anti-cancer agent; b) phospholipids (PL); and c) triglycerides (TG) prepared by the process as disclosed herein. In one embodiment of the above, the synthetic LDL nanoparticle is prepared by any of the disclosed process, wherein the LDL nanoparticle becomes coated with apolipoprotein upon intra venous injection and are recognized and internalized by cellular LDL receptors.

In another embodiment, there is provided a method for the treatment of cancer in a patient comprising administering to the patient a therapeutically effective amount of the stable, synthetic low density lipoprotein (LDL) nanoparticle of any one of the above embodiments, aspects and variations, to a patient in need of such treatment. In another aspect of the method, the cancer is selected from the group consisting of leukemia, neuroblastoma, glioblastoma, cervical, colorectal, pancreatic, renal melanoma, lung, breast, prostate, ovarian and head and neck.

DETAILED DESCRIPTION OF THE INVENTION

Brief Description of the Figures

FIG. 1 is a representative plot showing that particle size reaches the 55-60 nm plateau after 40 discrete passes that is equal to 20 mm of processing.

FIG. 2 is a representative plot showing particle size increased from 63 to 79 nm over 36 days.

FIG. 3 is a representative graph showing cooling conditions to allow further decreasing of the particle size to 43 nm.

FIG. 4 is a representative graph showing a particle size analysis of drug-free formulation where the resultant particle size was significantly smaller after processing at <30° C. temperatures compare to processing at 60° C.

FIG. 5 is a representative graph showing particle size reaches the plateau or resistance (Resistance 1-R1) at ~130 nm after 30 min of processing at 10-20° C.

FIG. 6 is a representative graph showing different particle size and stability over time.

FIG. 7 is a representative graph showing particle size at different temperatures.

FIG. 8 is a representative graph showing particle size increase over time.

FIG. 9 is a representative graph showing change in particle size over time and temperature.

FIG. 10: Representative graph showing stability of ART-207 formulation over time.

FIG. 11 is a representative graph showing relative particle size over processing time and temperatures.

FIG. 12 is a representative graph showing particle size and stability over time.

FIG. 13 is a representative graph showing particle size over time and temperature.

FIG. 14 is a representative graph showing particle size and stability of ART-207 over time.

FIG. 15 is a representative graph showing particle size over time and temperature.

FIG. 16 is a representative graph showing particle size and stability of ART-207 formulation.

FIG. 17 is a representative graph showing particle size and processing times.

FIG. 18 is a representative graph showing particle size and stability of drug-free formulations.

FIG. 19 is a representative graph showing particle size over processing times and temperatures.

FIG. 20 is a representative graph showing particle size and stability over time.

FIG. 21 is a representative graph showing stability of drug-free and ART-207 containing formulations.

FIG. 22 is a representative graph of effect of paclitaxel and formulated ART-207 on non-tumored mouse weight.

FIG. 23 is a representative graph of effect of paclitaxel and formulated ART-207 on tumored mouse weight.

FIG. 24 is a representative graph of paclitaxel and formulated ART-207 on tumor weight.

FIG. 25 is a representative graph of mouse death rate in control and Rx treated groups.

FIG. 26 is a representative graph showing MF processing time.

FIG. 27 is a representative graph showing particle size and stability of ART-207 with formulation FIG. 28 is a representative graph showing particle size and processing times.

FIG. 29 is a representative graph showing particle size and stability of ART-207 containing formulation.

FIG. 30 is a representative graph showing particle size and processing time.

FIG. 31 is a representative graph showing particle size and stability of ART-207 containing formulation.

FIG. 32 is a representative graph showing particle size over processing time.

FIG. 33 is a representative graph showing particle size and stability of drug free formulation.

FIG. 34 is a representative graph showing particle size and processing times.

FIG. 35 is a representative graph showing particle size and stability of ART-207 containing formulation.

FIG. 36 is a representative graph showing particle size and processing time.

FIG. 37 is a representative graph showing particle size and stability of ART-207 containing formulation.

FIG. 38 is a representative graph showing particle size and processing time.

FIG. 39 is a representative graph showing particle size and stability of ART-207 containing formulation.

FIG. 40 is a representative graph showing particle size and processing time.

FIG. 41: Representative graph showing particle size and stability of ART-207 containing formulation.

FIG. 42 is a representative graph showing particle size and processing time.

FIG. 43 is a representative graph showing particle size and stability of drug free formulation.

FIG. 44 is a representative graph showing particle size and processing time.

FIG. 45 is a representative graph showing particle size and stability of ART-207 containing formulation.

FIG. 46 is a representative graph showing particle size and processing time.

FIG. 47 is a representative graph showing particle size and stability of drug-free formulation.

FIG. 48 is a representative graph showing particle size and processing time.

FIG. 49 is a representative graph showing particle size and stability of ART-207 containing formulation.

FIG. 50 is a representative graph showing particle size and processing time.

FIG. 51 is a representative graph showing particle size and stability of ART-207 containing formulation.

FIG. 52 is a representative graph of particle size and processing time.

FIG. 53 is a representative graph showing particle size and stability of ART-207 containing formulation.

FIG. 54 is a representative graph showing particle size and stability of drug-free and ART-207 containing formulation.

FIG. 55 is a representative graph showing effect of paclitaxel and formulated ART-207 on tumor growth.

FIG. 56 is a representative graph showing effect of paclitaxel and formulated ART-207 on tumored mouse weight.

FIG. 57 is a representative graph of mouse death rate in control and Rx treated groups.

FIG. 58 is a representative graph showing effect of paclitaxel and formulated ART-207 on tumored mouse weight.

FIG. 59 is a representative graph showing the effect of formulated ART-207 on tumor weight.

FIG. 60a is a representative graph showing effect of paclitaxel and formulated ART-207 on tumor weight.

FIG. 60b is a representative graphs showing effect of paclitaxel and formulated ART-207 on tumored mouse weight.

FIG. 61 is a representative graphs showing particle size and processing time.

FIG. 62 is a representative graph showing particle size and stability of ART-207 containing formulation.

FIG. 63 is a representative graph showing particle size and processing time.

FIG. 64 is a representative graph showing particle size and stability of ART-207 containing formulation.

FIG. 65 is a representative graphs showing results of treatment of tumored and non-tumored mice FIG. 66 is a representative graph of plasma levels of paclitaxel.

FIG. 67 is a representative graph showing plasma levels of ART-207 after administration.

FIG. 68 is a representative graph showing concentration of paclitaxel in tissues of non-tumored mice injected with paclitaxel or formulated ART-207.

FIG. 69 is a representative graph showing concentration of paclitaxel in tissues in tumored mice injected with paclitaxel or formulated ART-207.

FIG. 70 is a representative graph showing tumor concentrations of paclitaxel in tumored mice injected with palcitaxel or formulated ART-207.

FIG. 71 is a representative graph showing particle size and processing time.

FIG. 72 is a representative graph showing particle size and stability of ART-207 containing formulation.

FIG. 73 is a representative graph showing particle size and processing time.

FIG. 74 is a representative graphs showing particle size and stability of ART-207 containing formulation.

FIG. 75 is a representative graphs showing article size and processing time in minutes.

FIG. 76 is a representative graph showing particle size and stability with time in days.

FIG. 77 is a representative graph showing Effect of TG/ART-207 ratio on ART-207 incorporation and particle stability.

FIG. 78 is a representative graph showing dependence of particle size and stability on processing temperatures.

FIG. 79 is a representative graph showing particle size on processing time and temperature.

FIG. 80 is a representative graph showing particle size and stability of ART-287 containing formulation with time in days.

FIG. 81 is a representative graph showing particle size and temperature with time in minutes.

FIG. 82 is a representative graph showing particle size and stability of ART-287 containing formulation with time in days.

FIG. 84 describes some embodiments of the Acid Labile Lipophilic Molecular Conjugates.

Figure 83:
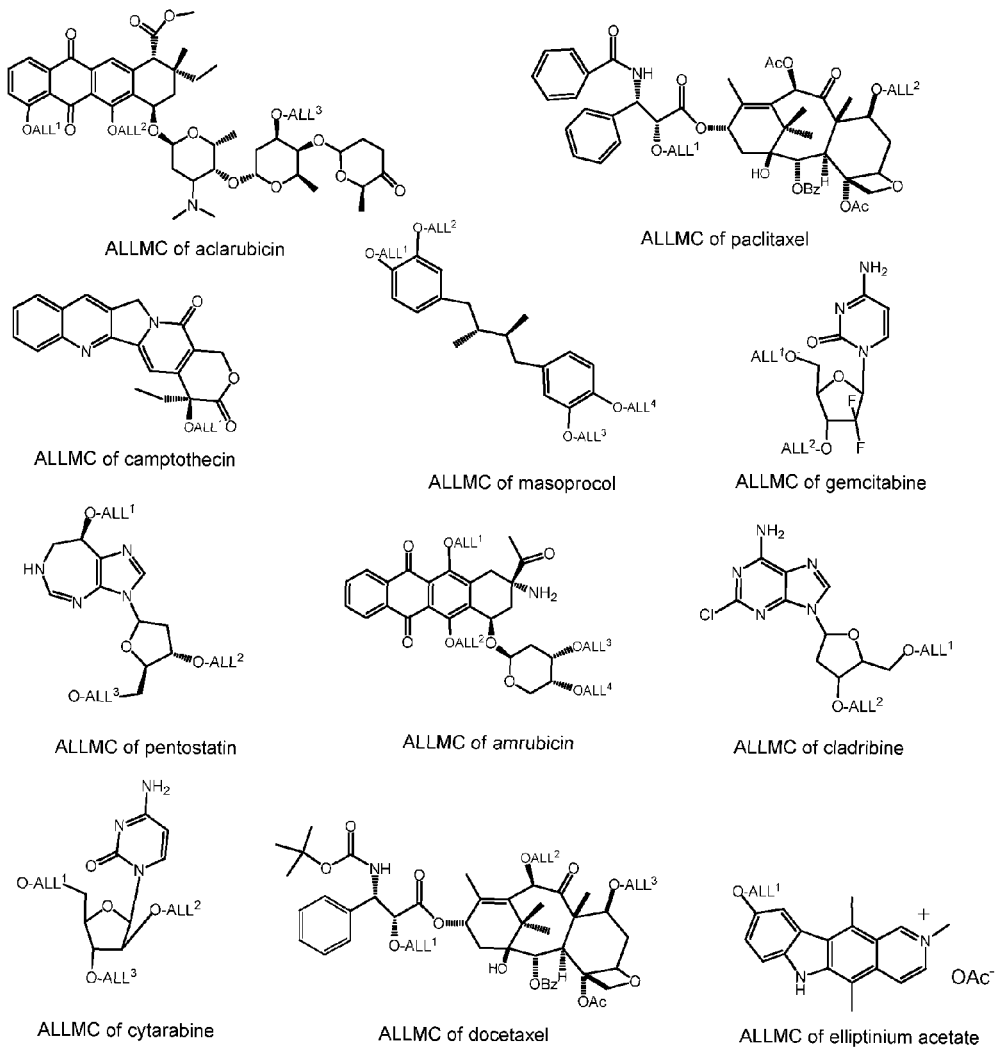
FIG. 83 describes some embodiments of the Acid Labile Lipophilic Molecular Conjugates.

Development of lipid-based Drug and Pro-Drug formulations:

Optimization of Drug/ProDrug incorporation capacity, particle size and stability. General procedures for preparation of nanoparticulate lipid based "pseudo LDL" formulations are found in Arbor Therapeutics, LLC Standard Operating Procedures; ART 001 Coarse Emulsion Preparation Rev. 1, ART 002 Microfluidics Model 110P Gen II (MF) Rev 1, and ART 003 Nicomp 380 ZLS Particle Size Analyses Rev. 1. Exceptions to these SOPs are noted.

Abbreviations: PC—phosphatidylcholine, TG—triglycerides, TC—total cholesterol, FC—free cholesterol, CE—esterified cholesterol, U—Ubiquinol, VitE—Vitamin E (mixed tocopherols), P188—Poloxamer 188, DMPC—1,2-Dimyristoyl-sn-glycero-3-phosphorylcholine, PS—Phosphotidyl serine; MFP—microfluidizer processing, IC—interaction chamber, ICJ—interaction chamber jacket; TSPM—total solids premix; REM—resultant emulsion; %—percent of total solids, TL, %—percent of total lipids, W/V—weight to volume; Recovery, %—percent of ART-207 recovered in formulation after microfluidizer processing and sterile 0.22 um filtration; mfg—manufacturing; Premix—pre-mixture; ND—not determined; BDL—below detection limit. R—Resistance.

All of the logP calculations for the anti-cancer agents noted in the table below were done online at www.chemicalize.org which uses the logP predictor from ChemAxon. The ChemAxon algorithm is based on: Vellarkad N. Viswanadhan et al., *Journal of Chemical Information and Computer Sciences* 1989 29 (3), 163-172.

| Anti-Cancer Agents | logP | Approved | Anti-Cancer Agents | LogP | Approved |
|---|---|---|---|---|---|
| ART-153 | 24.61 | n/a | ART-137 | 6.22 | |
| ART-164 | 12.91 | n/a | Mitotane | 6.11 | Adrenal |
| ART-152 | 12.86 | n/a | Epothilone D | 5.10 | |
| ART-209 | 12.56 | n/a | Epothilone C | 4.85 | |
| ART-163 | 12.19 | n/a | Masoprocol | 4.76 | |
| ART-151 | 12.04 | n/a | Cabozantinib | 4.66 | Thyroid |
| ART-207 | 11.68 | n/a | Lapatinib | 4.64 | Breast |
| ART-156 | 11.42 | n/a | ART-448 | 4.53 | |
| ART-185 | 11.40 | n/a | Valrubicin | 4.49 | Bladder |
| ART-161 | 11.31 | n/a | ART-287 | 4.41 | |
| ART-467 | 11.15 | n/a | Imatinib | 4.38 | Leukemias |
| ART-208 | 11.05 | n/a | Sorafenib | 4.34 | Liver, Kidney, Thyroid |
| ART-162 | 10.69 | n/a | Epothilone | 4.21 | |
| ART-449 | 9.77 | n/a | Cabazitaxel | 4.20 | Prostate |
| ART-441 | 9.32 | n/a | Carfilzomib | 4.20 | Multiple myeloma |
| Gossypol | 8.02 | | Vinblastine | 4.18 | Breast, myeloma, testicular |
| Fulvestrant | 7.57 | Breast | Axitinib | 4.15 | Kidney |
| Everolimus | 7.40 | Kidney | Epothilone B | 4.12 | |
| ART-332 | 7.19 | | Bosutinib | 4.09 | CML |
| Temsirolimus | 7.13 | Kidney | | | |

Materials used:

| Reagent | Vendor | Part Number | Lot Number |
|---|---|---|---|
| Phosphatidylcholine | Lipoid, GMBH | Lipoid E 80 | 1032718-121052 Mfg Date July 2010 Retest Date July 2013 |
| DMPS (1,2-Dimyristoyl-sn-Glycero-3-[Phospho-L-Serine] (Sodium Salt) | Avanti Polar Lipids, Inc. | 840033P | 140PS-83 |
| Soybean Oil (triglycerides) | Crisco | Pure Vegetable Oil Soybean oil | 1095420 Best Before 5 APR. 2013 |
| Cholesterol, 95% | Alfa Aesar | A11470 | L23W024 |
| Cholesterol Oleate (cholesterol ester) | Alfa Aesar | A-11378 | G03Y033 |
| Vitamin E, mixed tocopherols | Swanson (AMD) | SW152 | Illegible Lot #, Mfg Date July 2012 |
| Ubiquinol, co-enzyme Q | Kaneka Corporation | Kaneka QH ™ | FB02-0104 |
| Polaxamer P-188 (Pluronic F68; Polyethylene-Polypropylene Glycol) N.F. | Spectrum Chemicals | P 1169 CAS 90003-11-6 | 2AK0895 |
| DMPC (1,2-dimyristoyl-sn-glycero-3-phosphorylcholine) | Avanti Polar Lipids, Inc. | 850345P | 140PC-261 |
| ART-207 | Arbor Therapeutics, LLC | ART-207 | AW001- 243 AW004-13 AW004-24 |
| ART 287 | Arbor Therapeutics, LLC | ART 287 | |
| Sodium Chloride, ACS | Alfa Aesar | 12314 | L12X071 |
| Distilled Water | Kroger Grocery | Distilled Water | NA |
| Methylene Chloride, ACS Stabilized | Fisher Scientific | L-14119 | 125544 |
| Nitrogen | NexAir | HP NI-3 | 3904713-10-4 |
| Glacial Acetic Acid, ACS | Reagents, Inc. | 5-10060-3 | 1004NE |
| Sterile Filters, 0.22 μm, PES | Fisher Scientific | 50 mL 09-741-88 150 mL 09-741-01 500 mL 09-761-107 | NA NA NA |
| Cuvettes, polystyrene 4.5 mL | Fisher Scientific | 14 955 125 | NA |

Equipment used:

| Description | Manufacturer | Model Number |
|---|---|---|
| 400 gram balance | Denver Instrument | SI-403 |
| 100 gram balance | Denver Instrument | APX-100 |
| Emersion Hand Blender | Oster ® | 2605 |
| Variable Voltage Control | Glas-Col ® | 104A PL1202 |
| MicroFludizer ® | MicroFluidics, Inc. | M110P GEN II |
| Particle Sizer | Particle Sizing Systems | Nicomp ™ 380 ZLS |
| HPLC | Agilent | HP 1100 Series |

Analytical Quantitation of ART-207:

The Analytical Method Development for Quantitation of ART-207 concentration in LDL like lipid emulsion nanoparticles was an evolutionary process over approximately 18 months.

Summary of Methods Used and Method Changes:

Taxane_Prodrug.M—Variable sized neat emulsion injections:

| 13 AUG. 2012 | Calibration Curve/Response Linearity |
| 17 JAN. 2013 | Dilution of emulsion samples 1:10 with IPA |

Taxane_Test.M—Dilution of emulsion samples 1:10 with IPA, 1 μL injections:

| Rev. 0 | 20 JAN. 2013 | Higher column temperature 55° C. vs 40° C. |
| Rev. 1 | 9 FEB. 2013 | External Standard Preparation change to 100 mg/100 mL |
| Rev. 2 | 11 MAR. 2013 | Injection Volume increase from 1 μL to 3 μL |
| Rev. 3 | 10 MAY 2013 | Use of bracketing external standards and duplicate sample analyses defined in draft Standard Operating Procedure - |
| ART | | 005, HPLC Analysis of Formulated ART-207 |

Methods used to Quantitate ART-207 in emulsions prepared for the following studies:

| Taxane_Prodrug.M | 9 OCT. 2012 | In-Vitro Study |
| Taxane Test.M, Rev. 0 | 20 & 21 JAN. 2013 | MTD Study |
| Taxane Test.M, Rev. 1 | 6 MAR. 2013 | MTD Study |
| Taxane Test.M, Rev. 2 | 13 MAR. 2013 | Efficacy Study |
| Taxane Test.M, Rev. 3 | 13 MAY 2013 | PK/PD and Particle Size Comparison Toxicity/Efficacy Study |

The three HPLC Methods used were similar. Emulsion samples were injected neat during this time. All methods used a Phenomenex 4.6×50 mm Luna 5μ C18(2) 100A, part number 00B-4252-E0 column, flow rate: 1.5 mL/minute, detection: 230 nm, column temperature: 40° C., and injection volume: variable.

The gradient tables and injection volumes for each of these three methods are as follows:

| A = Acetonitrile Taxane_Prodrug.M Injection Volume 2 μL | | | B = % 0.01 M H$_3$PO$_4$ Water Taxane_Prodrug_Short.M Injection Volume 1 μL | | | Taxane_Prodrug_7 min.M Injection Volume 20 μL | | |
|---|---|---|---|---|---|---|---|---|
| Min. | % A | % B | Min. | % A | % B | Min. | % A | % B |
| 0 | 50 | 50 | 0 | 50 | 50 | 0 | 50 | 50 |
| 1 | 50 | 50 | 1 | 50 | 50 | 1 | 50 | 50 |
| 3 | 100 | 0 | 3 | 100 | 0 | 3 | 100 | 0 |
| 10 | 100 | 0 | 6 | 100 | 0 | 7 | 100 | 0 |
| 11 | 50 | 50 | 7 | 50 | 50 | 8 | 50 | 50 |
| 13 | 50 | 50 | 9 | 50 | 50 | 10 | 50 | 50 |

Taxane_Prodrug.M was used to determine linearity of response which was shown to be $R^2$=0.9997 for ART-207 from 0.6 to 5.2 mg/mL.

Taxane_Prodrug.M was also used to quantitate the emulsion prepared for the In-Vitro Cytotoxicity Study.

All Taxane_Prodrug.M methods showed carryover of emulsion components from a previous injection to the subsequent injections. Part of this carryover co-eluted with the ART-207 peak. Buffer blanks between samples helped a little. A 3 minute column wash method using 100 μL injections of 50/50 chloroform/methanol reduced the carryover considerably. Analyses of drug free formulations for the MTD Study showed no drug presence in the analyzed samples that was not possible to demonstrate with previous analytical procedures. Blank subtractions were not appropriate since emulsions had a peak eluting as the same time as ART-207.

A new method was developed which solved the emulsion component carryover problem. The higher column temperature 55° C. vs 40° C. may assist in liquefying and dissolving the emulsion particles better, allowing them to be washed off the column in the column wash. The gradient starts at higher acetonitrile concentration and the gradient is shallower to provide for resolution of any impurities. Analyses of drug free emulsions may be performed with confidence in a "Below Detection Limit" statement of result.

The HPLC analytical method used to quantitate ART-207 in lipid emulsions is TAXANE TEST.M, Rev. 0, performed on an Agilent 1100 quaternary pump and single wavelength system. The column is a Phenomenex 4.6×50 mm Luna 5μ C18(2) 100A, part number 00B-4252-E0. The method conditions are: flow rate: 1.5 mL/minute, detection: 230 nm, column temperature: 55° C., and injection volume: 1 μL. The gradient table is as follows:

| Time, minutes | % Acetonitrile | % 0.01M H$_3$PO$_4$ Water |
|---|---|---|
| 0 | 75 | 25 |
| 7 | 100 | 0 |
| 9 | 100 | 0 |
| 10 | 75 | 25 |
| 11 | 75 | 25 |

The typical retention time of ART-207 is ±5.8 minutes in this method. Lipid emulsion sample preparation is 1 part emulsion into 9 parts isopropanol (1:10). Linearity of response was shown to be $R^2$=0.9997 for ART-207 from 0.6 to 5.2 mg/mL in a similar acetonitrile/water C18 method. Quantitation is accomplished by using a response factor calculated from an external standard. The data are shown in the table. During the preparations of the lipid emulsions for this MTD study, unexplained fluctuations in the concentration of ART-207 were observed and investigated. The external standards were prepared using approximately 1 mg of ART-207 dissolved in 1 mL of solvent. Accuracy and consistency were improved when the external standard preparation was changed to 100 mg of ART-207 dissolved in 100 mL of solvent (Taxane Test.M, Rev. 1). Taxane Test.M, Rev. 1 method was used to re-determine and revise concentrations of ART-207 in emulsions prepared for the MTD study. The values reported initially (Taxane Test.M, Rev. 0) and the more accurate re-determined values (Taxane Test.M, Rev. 1) are shown in the table below.

| Lot Number | Taxane Test.M, Rev. 0 Original Concentration Reported, mg/mL | Taxane Test.M, Rev. 1 Recalculated Concentration, mg/mL |
|---|---|---|
| 002-119-1 | 2.01 | 2.26 |
| 002-119-2 | 3.02 | 3.40 |
| 002-119-3 | 3.98 | 4.49 |
| 002-119-4 | 6.13 | 6.91 |

On 11 Mar. 2013 the injection volume was increased from 1 μL to 3 μL to reduce the impact of injection to injection variability on the standard area counts used to determine response factor as well as sample area counts, Taxane Test.M, Rev. 2.

Bracketing external standards and duplicate analyses of samples were used in analytical quantitation of ART-207 and are defined in Standard Operating Procedure—ART 005, HPLC Analysis of Formulated ART-207, Taxane Test.M, Rev. 3.

Analytical Quantitation of 287 (Lot# ISI-30052013-1).

Taxane Test.M, Rev 3" Analytical Method was used for Quantitation of ART 287 concentration in LDL like lipid emulsion nanoparticles. Sterile 0.22 um filtration of resultant emulsions did not significantly affect the ART-207 content in experiments described below. The particle size for all prepared coarse suspensions was always in the range 400-800 nm and did not affect the rate of particle size decrease during MF processing. MF processing volume was 100 ml unless specified. For all examples described below, see also Master Tables 1, 2 and 3.

Experiment 1. Preparation of Drug-Free Lipid Emulsion Using Original Formulation To investigate effect of discrete passes vs recycling mode (return of the material into the feed reservoir) and controlled (≤60° C.) ICJ temperature on particle size.

TABLE 1a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 17 Dec. 2012 | 002.102.1 | TSPM | 2330 | 1239 | 206 | 153 | 10 | 10 | 0 | 0 | 0 | 0 |

TABLE 1b

Ratios of major formulation components.

| TG/ART-207 | PC/ART-207 | PC/TG | FC/CE |
|---|---|---|---|
| N/A | N/A | 1.88 | 1.35 |

Coarse suspension was prepared and MF processed (lot#002.103.1).

TABLE 1c

Particle size, ART-207 content, and particle stability of resultant emulsion.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 18 Dec. 2012 | 002.103.1 | 63 | N/A | N/A | 36 | 79 |

MFP. FIG. 1 shows that particle size reaches the 55-60 nm plateau after 40 discrete passes that is equal to 20 min of processing (one discrete pass is ~30 sec). MFP was stopped after 80 passes and material filtered. Particle size slightly increased after 0.22 μm filtration from 55 to 63 nm Processing via discrete passes at ~60-65° C. (temperature of IC jacket) did not result in improvement of particle size relative to lipid formulations generated in prior studies. Particle size analysis and stability. The resultant emulsion was unstable. In FIG. 2 and Table 1c, particle size increased from 63 to 79 nm over 36 days.

Experiment 2. Preparation of drug-free lipid emulsion using original formulation.

Investigate the effect of lower (<30° C.) ICJ temperature (i.e. effect of "local" cooling of IC jacket) on resultant particle size.

TABLE 2a

Formulation composition.

| Date | Lot# | Material | Components Weighed, mg (per 100 ml) | | | | | | | | | |
|---|---|---|---|---|---|---|---|---|---|---|---|---|
| | | | PC | TG | FC | CE | U | Vit E | ART | P188 | DMPC | PS |
| 17 Dec. 2012 | 002.102.2 | TSPM | 2338 | 1247 | 203 | 152 | 10 | 10 | 0 | 0 | 0 | 0 |

TABLE 2b

Ratios for major formulation components.

| TG/ART-207 | PC/ART-207 | PC/TG | FC/CE |
|---|---|---|---|
| N/A | N/A | 1.87 | 1.34 |

Coarse emulsion was prepared and MF processed (lot#002.104.1). MF processing was performed in recycling mode.

TABLE 2c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 19 Dec. 2012 | 002.104.1 | 45 | N/A | N/A | 35 | 82 |

2a. Ice cubes were placed around IC jacket. After 10 min of MF processing the particle size dropped from 439 nm (coarse emulsion) to 66 nm, and in 20 min it reached a plateau at ~58 nm. Further processing to 30 mm did not decrease the particle size (FIG. 3).

2b. To achieve better contact of cooling agent with IC and to further lower its temperature, ice was removed from lower tray and glycol bath set to 10° C. was used to submerge interaction chamber (with surrounding pipelines and back pressure chamber) in 10° C. glycol. These cooling conditions allowed further decreasing of the particle size to 43 nm (FIG. 3).

Particle size analysis of drug-free formulation. In FIG. 4, Table 1c, and 2c, the resultant particle size was significantly smaller after processing at <30° C. temperatures compare to processing at 60° C. Both processing conditions resulted in unstable particles. 63 to 79 and 45 to 82 nm particle size increase was observed in lot#002.103.1 and 002.104.1, respectively.

Experiment 3. Preparation of ART-207 containing lipid emulsion using original formulation. Investigating ART-207 (Lot# AW-001-243) incorporation capacity of original formulation and effect of ART-207 on particle size and stability.

TABLE 3a

Formulation composition.

| Date | Lot# | Material | Components Weighed, mg (per 100 ml) | | | | | | | | | |
|---|---|---|---|---|---|---|---|---|---|---|---|---|
| | | | PC | TG | FC | CE | U | VitE | ART | P188 | DMPC | PS |
| 18 Dec. 2012 | 002.103.2 | TSPM | 2176 | 1145 | 184 | 141 | 10 | 10 | 320 | 0 | 0 | 0 |

TABLE 3b

Ratio for major formulation components.

| TG/ART-207 | PC/ART-207 | PC/TG | FC/CE |
|---|---|---|---|
| 3.58 | 6.80 | 1.90 | 1.30 |

Coarse suspension was prepared and MF processed (lot#002.105.1).

TABLE 3c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 19 Dec. 2012 | 002.105.1 | 82 | 3.14 | 98.1 | 35 | 196 |

MFP. In FIG. 5, particle size reaches the plateau or resistance (Resistance 1-R1) at ~130 nm after 30 mm of processing at 10-20° C. Raising the temperature to 50-60° C. resulted in lowering particle size to 100 nm and reaching R2. Lowering the temperature back to 10-20° C. resulted in further particle size decrease to 77 nm. MFP was stopped and material was filtered. Slight increase of particle size from 77 to 82 nm was observed after filtration.

HPLC Analysis. ART-207 content in resultant emulsion determined by HPLC (Taxane_Prodrug.M) was 3.14 mg/ml. Data indicate that 98% of the drug used for preparation of this formulation was incorporated into lipid particles (Table 3c).

Particle size analysis of ART-207 containing formulation. The resultant ART-207 containing emulsion was unstable. FIG. 6 and Table 3c show that particle size increased from 82 to 196 nm over 35 days.

Addition of ART-207 to formulation notably decreases stability of resultant emulsion.

Experiment 4. Preparation of ART-207 (Lot# AW-001-243) containing lipid emulsion. Investigating the effect of increased phospholipid content and decreased FC/CE ratio while keeping the amount of TC the same (table 4b and 4a) on drug incorporation capacity and stability of resultant nanoparticles.

TABLE 4a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| Jan. 9, 2013 | 002.107.2 | TSPM | 4157 | 1397 | 70 | 347 | 10 | 10 | 648 | 0 | 0 | 0 |

TABLE 4b

Ratios for major formulation components.

| TG/ART-207 | PC/ART-207 | PC/TG | FC/CE |
|---|---|---|---|
| 2.16 | 6.42 | 2.98 | 0.20 |

Coarse suspension was prepared and MF processed (lot#002.108.1).

TABLE 4c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 9 Jan. 2013 | 002.108.1 | 129 | 4.81 | 74.2 | 14 | 184 |

MFP. In FIG. 7, particle size reaches R1 at ~125 nm after 40 mm of processing at ~60° C. Lowering the temperature to ~20° C. resulted in lowering particle size to 80 nm and reaching R2. Raising the temperature to 50° C. resulted in particle size increase to ~108 nm. MFP was stopped and filtered. Increase of particle size from 108 to 129 nm was observed after filtration.

HPLC Analysis. ART-207 content in resultant emulsion determined by HPLC (Taxane_Prodrug.M) was 4.81 mg/ml. Data indicate that 74% of the drug used for preparation of this formulation was incorporated into lipid particles (Table 4c). Particle size analysis of ART-207 containing formula tion. The resultant ART-207 containing emulsion was unstable. In FIG. 8 and Table 4c, particle size increased from 129 to 184 nm over 14 days.

Increased phospholipid content and decreased FC/CE ratio resulted in higher ART-207 particle content but did not improve stability of resultant emulsion.

Experiment 5. Preparation of ART-207 (Lot# AW-001-243) containing lipid emulsion.

Investigate effect of further increase of phospholipid concentration and decrease of CE on drug incorporation capacity and stability of resultant nanoparticles; and B. To optimize the temperature control strategy: raising the temperature from 20° C. to 60° C. in experiment #4 resulted in undesirable increase of the particle size.

Data indicate that 85% of the drug used for preparation of this formulation was incorporated into lipid particles (Table 5c). The resultant drug content of the particles was higher than in previous experiment indicating that increase of coating material (phospholipid) facilitates drug incorporation (see Tables 3a, 3c, 4a, and 4c).

Particle size analysis of ART-207 containing formulation. Although the resultant particle size was significantly smaller (Table 5c) compared to previous experiment (Table 4c), the emulsion was extremely unstable. In FIG. 10 and Table 5c, particle size increased from 74 to 149 nm over 14 days and from 74 to 169 nm over 33 days.

TABLE 5a

Formulation composition.

| Date | Lot# | Material | PC | TG | FC | CE | U | Vit E | ART | P188 | DMPC | PS |
|---|---|---|---|---|---|---|---|---|---|---|---|---|
| 9 Jan. 2013 | 002.108.2 | TSPM | 5025 | 1397 | 71 | 216 | 10 | 10 | 648 | 0 | 0 | 0 |

Components Weighed, mg (per 100 ml)

TABLE 5b

Ratios for major formulation components.

| TG/ART-207 | PC/ART-207 | PC/TG | FC/CE |
|---|---|---|---|
| 2.16 | 7.75 | 3.60 | 0.33 |

Coarse suspension was prepared and MF processed (lot#002.109.1).

TABLE 5c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 9 Jan. 2013 | 002.109.1 | 74 | 5.50 | 84.9 | 33 | 169 |

MFP. In FIG. 9, particle size reaches R1 at ~105 nm after 30 min of processing at ~60° C. Lowering the temperature to ~20° C. resulted in lowering particle size to 73 nm and reaching R2. MFP was stopped and filtered. No increase of particle size was observed after filtration.

HPLC Analysis. ART-207 content in resultant emulsion determined by HPLC (Taxane_Prodrug.M) was 5.5 mg/ml.

Further increase of phospholipid and decrease of CE and subsequently TC content resulted in smaller particles and higher (relative to previous experiment #4) capacity of the formulation to incorporate ART-207 but did not improve stability of resultant emulsion. A repeat of this experiment gave similar results which indicate the processing parameters are reproducible and give reproducible outcomes.

Experiment 6. Preparation of ART-207 (Lot# AW-001-243) containing lipid emulsion. Increased ART-207 content results in decreased stability of the resultant particles, experiment #6 was performed to determine the effect of lowering ART-207 concentration on particle size and stability.

TABLE 6a

Formulation composition.

| Date | Lot# | Material | PC | TG | FC | CE | U | Vit E | ART | P188 | DMPC | PS |
|---|---|---|---|---|---|---|---|---|---|---|---|---|
| 10 Jan. 2013 | 002.109.3 | TSPM | 5170 | 1392 | 70 | 213 | 10 | 10 | 213 | 0 | 0 | 0 |

Components Weighed, mg (per 100 ml)

TABLE 6b

| Ratio for major formulation components. | | | |
|---|---|---|---|
| TG/ART-207 | PC/ART-207 | PC/TG | FC/CE |
| 6.54 | 24.27 | 3.71 | 0.33 |

Coarse suspension was prepared and MF processed (lot#002.111.1).

TABLE 6c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size, nm |
|---|---|---|---|---|---|---|
| 11 Jan. 2013 | 002.111.1 | 47 | 1.86 | 87.3 | 24 | 66 |

MFP. In FIG. 11, particle size reaches R1 at ~66 nm after 20 mm of processing at ~60° C. Lowering the temperature to ~20° C. resulted in lowering particle size to 42 nm MFP was stopped and was filtered. Increase of particle size from 42 to 47 nm was observed after filtration.

HPLC Analysis. ART-207 content in resultant emulsion determined by HPLC (Taxane_Prodrug.M) was 1.86 mg/ml. Data indicate that 87% of the drug used for preparation of this formulation was incorporated into lipid particles (Table 6c). Particle size analysis of ART-207 containing formulation. The resultant ART-207 containing emulsion was more stable relative to previous formulations. In FIG. 12 and Table 6c, particle size increased from 47 to 66 nm over 24 days.

Lowering ART-207 and maintaining high phospholipid content (Table 6a and b) resulted in: a) significantly smaller particle size compared to the size previously attained in experiment #5 (see also tables 5a,b,c and 6a,b,c), and b) more stable particles (relative to emulsions obtained in previous experiments).

Experiment 7. Preparation of ART-207 (Lot# AW-001-243) containing lipid emulsion.

Effect of lowering triglycerides content on ART-207 incorporation, particle size and stability.

TABLE 7a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 11 Jan. 2013 | 002.110.4 | TSPM | 5900 | 652 | 69 | 150 | 10 | 10 | 648 | 0 | 0 | 0 |

TABLE 7b

| Ratios for major formulation components. | | | |
|---|---|---|---|
| TG/ART-207 | PC/ART-207 | PC/TG | FC/CE |
| 1.01 | 9.10 | 9.05 | 0.46 |

Coarse suspension was prepared and MF processed (lot#002.111.2).

TABLE 7c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size, nm |
|---|---|---|---|---|---|---|
| 11 Jan. 2013 | 002.111.2 | 66 | 3.88 | 59.9 | 38 | 75 |

MFP. In FIG. 13, particle size reached R1 at ~105 nm after 20 mm of processing at ~60° C. Lowering the temperature to ~20° C. and further to 10° C. resulted in further increase of the particle size from 105 to 118 nm and reaching R2. Increasing temperature back to 50-60° C. resulted in particle size decrease to 90 nm and reaching next resistance point at 94 nm. Additional 30 mm processing at ~~25° C. decreased particle size from 94 to 84 nm MFP was stopped and filtered. Decrease of particle size from 84 to 66 nm was observed after filtration.

HPLC Analysis. ART-207 content in resultant emulsion determined by HPLC (Taxane_Prodrug.M) was 3.88 mg/ml. Data indicate that 60% of the drug used for preparation of this formulation was incorporated into lipid particles (7c). ART-207 incorporation capacity of the particles with low triglycerides content was decreased. Particle size analysis of ART-207 containing formulation. The ART-207 containing emulsion was more stable compared to formulations higher in triglycerides processed in experiments #3-6. In FIG. 14 and Table 7c, particle size did not increase from 66 to 75 nm over 38 days. For the next 30 days (68 days total) particle size increased to 92 nm.

Thus, lowering triglyceride content and maintaining high phospholipid content resulted in reasonably small and fairly stable particles. ART-207 incorporating capacity of low triglycerides emulsion was significantly decreased. Increase of phoshpolipid results in smaller particles with increased ART-207 content; Increase of phospholipid does not improve the particle stability; Decrease of ART-207 content results in decrease of particle size and improved stability; Decrease of TG content and therefore, TG/ART-207 ratio from ~2 to 1 results in decreased particle size, improved stability, but lower ART-207 incorporating capacity of formulation.

TG/ART-207 ratio appears to be an important pre-requisite in determining ART-207 incorporation capacity of the formulation; Higher TG/ART-207 ratio results in increased ART-207 incorporation capacity of the formulation but compromised particle stability, and lower ratio results in improved formulation stability but lower ART-207 incorporation capacity. There are at least two possible routes to optimizing ART-207 incorporation, particle size, and stability of emulsion preparations: Optimizing ratios for major formulation components.

Experiment 8. Preparation of ART-207 (Lot# AW-001-243) containing emulsion.

Investigating the effect of Poloxamer P188 (1% V/W) addition on ART-207 incorporation, particle size and stability. Poloxamers are non-ionic poly (ethylene oxide) (PEO)-poly (propylene oxide) (PPO) copolymers. Poloxamers are broadly used in clinical applications (1). Ability of P188 to intercalate in lipid monolayers and to seal the membranes (2) suggests their usefulness in improving stability of the lipid particles by possibly relieving the surface tension. P188 coating of nanoparticles reduces their opsonization by serum proteins and macrophage uptake (3) that is particularly relevant for in vivo applications. One of the most relevant features of P188 to this application is that P188 coating of the lipid nanoparticles does not prevent binding of Apolipoprotein E (4).

REFERENCES

1. Hitesh R. Patel et al. "Poloxamers: A pharmaceutical excipient with therapeutic behaviors". 2009. International Journal of PharmTech Research, Vol. 1, No. 2, pp 299-303. 2. Guohui Wu et al. "Interaction between Lipid Monolayers and Poloxamer 188: An X-Ray Reflectivity and Diffraction Study". 2005. Biophysical Journal Volume 89 November 2005 3159-3173. 3. Zhang, Wen-li et al. "Stealth tanshinone IIA-loaded solid lipid nanoparticles: effects of poloxamer 188 coating on in vitro phagocytosis and in vivo pharmacokinetics in rats". 2009. Acta Pharm Sin, 44: 1421-1428. 4. Parag Aggarwal et al. "Nanoparticle interaction with plasma proteins as it relates to particle biodistribution, biocompatibility and therapeutic efficacy". 2009. Advanced Drug Delivery Reviews 61, 428-437.

TABLE 8a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 15 Jan. 2013 | 002.115.4 | TSPM | 5123 | 1390 | 70 | 212 | 10 | 10 | 648 | 1000 | 0 | 0 |

TABLE 8b

Ratios for major formulation components.

| TG/ART-207 | PC/ART-207 | PC/TG | FC/CE |
|---|---|---|---|
| 2.15 | 7.91 | 3.69 | 0.33 |

Coarse suspension was prepared and MF processed (lot#002.116.1).

TABLE 8c

Particle size, ART-207 content, and particle stability of resultant emulsion.

| | | Particle size | ART-207 | | Formulation Stability | |
|---|---|---|---|---|---|---|
| Manufacturing Date | Lot# | by intensity, nm | Content, mg/ml | Recovery, % | Days past, mfg | Particle size nm |
| 16 Jan. 2013 | 002.116.1 | 62 | 6.07 | 93.7 | 4 | 146 |

MFP. In FIG. 15, particle size reached 60 nm after 30 mm of processing at ~60° C. At this point temperature was lowered to ~20° C. to determine if the decrease in particle size can be further facilitated at lower temperatures. Additional 20 min of processing resulted in significant particle size increase from 60 to 73 nm. Increasing temperature back to ~60° C. resulted in particle size decrease to 56 nm and reaching resistance point (R2). MFP was stopped and filtered. Increase of particle size from 56 to 62 nm was observed after filtration.

HPLC Analysis. ART-207 content in resultant emulsion determined by HPLC (Taxane_Prodrug.M) was 6.07 mg/ml.

Data indicate that 93.7% of the drug used for preparation of this formulation was incorporated into lipid particles (8c). Particle size analysis of ART-207 containing formulation. The resultant ART-207 containing emulsion was unstable. In FIG. 16 and Table 8c, particle size increased from 62 to 146 nm just after four days.

Addition of 1% (V/W) of P188 had destabilizing effect on the resultant emulsion. Preparation of lipid-based drug-free and ART-207 containing formulations for maximum tolerated dose (MTD) studies.

Experiment 9. Preparation of drug-free lipid emulsion.

TABLE 9a

Formulation composition.

| Date | Lot# | Material | PC | TG | FC | CE | U | Vit E | ART | P188 | DMPC | PS |
|---|---|---|---|---|---|---|---|---|---|---|---|---|
| 15 Jan. 2013 | 002.118.1 | TSPM | 5209 | 1387 | 69 | 213 | 10 | 10 | 0 | 0 | 0 | 0 |

TABLE 9b

Ratios for major formulation components.

| TG/ART-207 | PC/ART-207 | PC/TG | FC/CE |
|---|---|---|---|
| N/A | N/A | 3.75 | 0.33 |

Coarse suspension was prepared and MF processed (lot#002.118.0).

TABLE 9c

Particle size, ART-207 content and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 19 Jan. 2013 | 002.118.00 | 47 | N/A | N/A | 60 | 79 |

MFP. In FIG. 17, particle size reached 45 nm after 35 min of processing at ~60° C. MFP was stopped and material was filtered. Increase of particle size from 45 to 47 nm was observed after filtration.

HPLC Analysis. ART-207 content in resultant emulsion determined by HPLC (Taxane_Prodrug.M) was below detection limit.

Particle size analysis of drug-free formulation. The resultant emulsion was stable for at least 13 days. In FIG. 18 and Table 9c, particle size did not increase for 13 days. For the next 47 days (60 days total) particle size increased to 79 nm (FIG. 18 and Table 9 c).

Data shows that processing of drug-free high PC and TG containing formulation results in small and relatively stable particles.

Experiment 10. Preparation of ART-207 (Lot# AW-001-243) containing lipid emulsion. Manufacture of ART-207 containing emulsion for Maximum Tolerated Dose study.

TABLE 10a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 15 Jan. 2013 | 002.115.2 | TSPM | 5200 | 1389 | 70 | 213 | 10 | 10 | 673 | 0 | 0 | 0 |

TABLE 10b

Ratio for major formulation components.

| TG/ART-207 | PC/ART-207 | PC/TG | FC/CE |
|---|---|---|---|
| 2.07 | 7.73 | 3.74 | 0.33 |

150 ml of coarse suspension was prepared and MF processed (lot#002.119.4).

TABLE 10c

Particle size, ART-207 content, and particle stability of resultant emulsion.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 20 Jan. 2013 | 002.119.4 | 78 | 6.13 | 91.8 | 22 | 218 |

MFP. In FIG. 19, particle size reaches R1 at ~106 nm after 45 min of processing at ~60° C. Lowering the temperature to ~20° C. resulted in lowering particle size to 72 nm MFP was stopped and filtered. Increase of particle size from 72 to 78 nm was observed after filtration.

HPLC Analysis. ART-207 content in resultant emulsion determined by HPLC (Taxane_Test.M, Rev 0) was 6.13 mg/ml. Data indicate that 91% of the drug used for preparation of this formulation was incorporated into lipid particles (Table 10c). Particle size analysis of ART-207 containing formulation. The resultant ART-207 containing emulsion was unstable. In FIG. 20 and Table 10c, particle size increased from 78 to 218 nm over 22 days.

The outcome of this experiment was similar to results of experiment #5 which indicate: a) consistency in coarse emulsions preparation and processing, and b) yet unresolved stability issue for ART-207 containing formulations. Targeted doses of ART-207. The projected doses of formulated ART-207 for MTD study were the following: 64.4, 46, 34 and 22 mg per kg (mpk). All test articles were administered to mice via intravenous (iv) injections. The injection volumes to achieve projected doses noted in Table 11a.

TABLE 11a

ART-207 content, projected doses, and injection volumes.

| Lot# | Material | ART-207 required mg/ml | Dose, mpk | Injection Volume, ml (per 20 g of mouse weight) |
|---|---|---|---|---|
| 002.118.00 | Vehicle Control | N/A | N/A | 0.21 |
| 002.119.4 | Formulated ART-207 | 6.13 | 64.4 | 0.21 |
| 002.119.3 | Formulated ART-207 | 4.38 | 46 | 0.21 |
| 002.119.2 | Formulated ART-207 | 3.22 | 34 | 0.21 |
| 002.119.1 | Formulated ART-207 | 2.11 | 22 | 0.21 |

Preparation of dilutions of emulsion to achieve targeted concentrations of ART-207. The calculated targeted concentrations of formulated ART-207 for MTD study were the following: 6.13, 4.38, 3.22, and 2.11 mg/ml. To achieve 4.38, 3.22, and 2.11 mg/ml targeted concentrations of ART-207, emulsion lot#002-119-4 (6.13 mg/ml of ART-207) determined by HPLC (Taxane_Test.M, Rev 0) was diluted 1.4, 1.9 and 2.9 fold with acetic acid buffered saline (pH 5.5) to calculated concentrations: 4.38 mg/ml (lot#002-119-3), 3.22 mg/ml (lot#002-119-2), and 2.11 mg/ml (lot#002-119-1), respectively. All preparations were filtered and ART-207 content of undiluted lot and its diluted derivatives analyzed by HPLC (Table 11b).

TABLE 11b

|  |  |  |  | ART | | |
| --- | --- | --- | --- | --- | --- | --- |
| Date | Lot# | Material | Comments | Calculated mg/ml | HPLC mg/ml | Recovery % |
| 15 Jan. 2013 | 002.115.2 | TSPM** |  | 6.73 | N/A | N/A |
| 20 Jan. 2013 | 002.119.4 | Emulsion | DF* = 0.0 | 6.13 | 6.13 | 100.0 |
| 20 Jan. 2013 | 002.119.3 | Emulsion | DF* = 1.4 | 4.38 | 3.98 | 90.8 |
| 20 Jan. 2013 | 002.119.2 | Emulsion | DF* = 1.9 | 3.22 | 3.02 | 93.8 |
| 20 Jan. 2013 | 002.119.1 | Emulsion | DF* = 2.9 | 2.11 | 2.01 | 95.3 |

DF*—Dilution Factor,
TSPM**—total solids pre-mix.

Dilutions of starting lot #002-119-4 (6.13 mg/ml of ART-207) down to targeted concentrations of ART-207 will result in subsequent lowering of lipid content in resultant lots 002-119-3, 002-119-2 and 002-119-1. "Dilution vs independent formulation" was based on the following rationale: a) Independent formulation of different concentrations of ART-207 using identical lipid formula yields emulsions with significantly different particle size, whereas dilution does not affect particle size (Table 11d); this approach provides targeted concentrations of ART-207 that are incorporated in similar size particles, and b) should toxic effect of lipid occur it will be well represented by vehicle control that has highest lipid content in the series and is identical to lot#002-119-4 (6.13 mg/ml of ART-207) in lipid content (Table 11c).

TABLE 11c

|  |  |  |  | Components Weighed, mg (per 100 ml) | | | | | | | | | | | |
| --- | --- | --- | --- | --- | --- | --- | --- | --- | --- | --- | --- | --- | --- | --- | --- |
| Date | Lot# | Material | DF* | PC | TG | FC | CE | U | Vit E | ART | P188 | DMPC | PS | TS % | TL % |
| 15 Jan. 2013 | 002.118.1 | TSPM** | N/A | 5209 | 1387 | 69 | 213 | 10 | 10 | 0 | 0 | 0 | 0 | 6.9 | 6.9 |
| 19 Jan. 2013 | 002.118.00 | REM*** | N/A | 5209 | 1387 | 69 | 213 | 10 | 10 | 0 | 0 | 0 | 0 | 6.9 | 6.9 |
| 15 Jan. 2013 | 002.115.2 | TSPM | N/A | 5200 | 1389 | 70 | 213 | 10 | 10 | 673 | 0 | 0 | 0 | 7.6 | 6.9 |
| 20 Jan. 2013 | 002.119.4 | REM | 0.0 | 5200 | 1389 | 70 | 213 | 10 | 10 | 673 | 0 | 0 | 0 | 7.6 | 6.9 |
| 20 Jan. 2013 | 002.119.3 | REM | 1.4 | N/A | N/A | N/A | N/A | N/A | N/A | N/A | 0 | 0 | 0 | 5.4 | 4.9 |
| 20 Jan. 2013 | 002.119.2 | REM | 1.9 | N/A | N/A | N/A | N/A | N/A | N/A | N/A | 0 | 0 | 0 | 4.0 | 3.6 |
| 20 Jan. 2013 | 002.119.1 | REM | 2.9 | N/A | N/A | N/A | N/A | N/A | N/A | N/A | 0 | 0 | 0 | 2.6 | 2.4 |

DF*—Dilution Factor;
TSPM**—total solids pre-mix;
REM***—resultant emulsion

TABLE 11d

Particle size of resultant emulsion preparations.

| Date | Lot# | Material | DF* | Particle size, nm | TS % | TL % |
| --- | --- | --- | --- | --- | --- | --- |
| 15 Jan. 2013 | 002.118.1 | TSPM** | N/A | N/A | 6.9 | 6.9 |
| 19 Jan. 2013 | 002.118.00 | REM*** | N/A | 49.0 | 6.9 | 6.9 |
| 15 Jan. 2013 | 002.115.2 | TSPM | N/A | N/A | 7.6 | 6.9 |
| 20 Jan. 2013 | 002.119.4 | REM | 0.0 | 86.7 | 7.6 | 6.9 |
| 20 Jan. 2013 | 002.119.3 | REM | 1.4 | 86.4 | 5.4 | 4.9 |
| 20 Jan. 2013 | 002.119.2 | REM | 1.9 | 83.6 | 4.0 | 3.6 |
| 20 Jan. 2013 | 002.119.1 | REM | 2.9 | 81.7 | 2.6 | 2.4 |

DF*—Dilution Factor;
TSPM**—total solids pre-mix;
REM***—resultant emulsion

Approximately 20 ml of the following lots were shipped to the study site; Lot#002-118-00, Drug-free formulation (vehicle control); Lot#002-119-4, Formulated ART-207 (6.13 mg/ml); Lot#002-119-3, Formulated ART-207 (3.98 mg/ml); Lot#002-119-2, Formulated ART-207 (3.02 mg/ml); Lot#002-119-1, Formulated ART-207 (2.01 mg/ml). 10 ml samples of each lot were retained. ART-207 quantification in emulsion preparation resulted in improved "Taxane_Test.M, Rev 1" method (see above "Analytical Development" section). The revised ART-207 concentrations in shipped samples in the Table 11 f. Table 1 if shows that concentrations of ART-207 determined by Taxane_Test.M, Rev 1 method were significantly higher in all tested lots.

TABLE 11f

| | HPLC Analyses of ART-207 Content, mg/mL | |
| --- | --- | --- |
| Material | Taxane_Test.M, Rev 0 On the day of mfg | Taxane_Test.M, Rev. 1 9 Feb. 2013 |
| 002-118-00 | BDL | BDL |
| 002-119-1 | 2.01 | 2.26 |
| 002-119-2 | 3.02 | 3.40 |
| 002-119-3 | 3.98 | 4.49 |
| 002-119-4 | 6.13 | 6.91 |

The treatment of animals was carried out from 22 Jan. 2013 to 26 Jan. 2013. The revised on 9 Feb. 2013 doses used in animal studies are presented in the Table 11g.

TABLE 11g

Revised ART-207 doses.

| Lot# | Material | ART-207 mg/ml, revised | Dose, mpk | Injection Volume, ml (per 20 g of mouse weight) |
| --- | --- | --- | --- | --- |
| 002.151.5 | Vehicle Control | N/A | N/A | 0.21 |
| 002.119.4 | Formulated ART-207 | 6.91 | 72.6 | 0.21 |
| 002.119.3 | Formulated ART-207 | 4.49 | 47.1 | 0.21 |

TABLE 11g-continued

Revised ART-207 doses.

| Lot# | Material | ART-207 mg/ml, revised | Dose, mpk | Injection Volume, ml (per 20 g of mouse weight) |
|---|---|---|---|---|
| 002.119.2 | Formulated ART-207 | 3.40 | 35.7 | 0.21 |
| 002.119.1 | Formulated ART-207 | 2.26 | 23.7 | 0.21 |

MTD study consisted of two major phases:

Treatment for five consecutive days (Q1D×5): Administration of Paclitaxel, formulated ART-207, and vehicle control (drug-free formulation) via intravenous injections; Assessment of tumor size and mouse weight; Assessment of vital signs; Monitoring the animals after end of treatment for two weeks; Assessment of tumor size and mouse weight; and assessment of vital signs. Material remaining from the dosing emulsion solutions was shipped back to Arbor Therapeutics after the end of the treatment phase. ART-207 content was assessed for all formulations used in MTD studies. The assessment of returned material was carried out side by side with material retained.

Table 11h shows material evaluated by Taxane_Test.M Rev. 1 method, returned from MTD study site, and materials retained have similar drug content in all tested lots. The data indicate good stability of formulated ART-207 and proper material handling at the research sites.

TABLE 11h

HPLC Analyses of ART-207 Content, mg/mL

| Material | Taxane_Test.M Rev 0 On the day of mfg | Taxane_Test.M Rev 1 9 Feb. 2013 | Taxane_Test.M Rev 1 Returned Material | Taxane_Test.M Rev 1 Retained Material |
|---|---|---|---|---|
| 002-118-00 | BDL | BDL | BDL | BDL |
| 002-119-1 | 2.01 | 2.26 | 2.37 | 2.32 |
| 002-119-2 | 3.02 | 3.40 | 3.49 | 3.50 |
| 002-119-3 | 3.98 | 4.49 | 4.74 | 4.71 |
| 002-119-4 | 6.13 | 6.91 | 6.75 | 6.58 |

Particle size of the material remaining from the MTD Study and returned to Arbor was assessed on the day of its delivery. The assessment of returned material was carried out side by side with material retained. Stability data are presented in Table 13k and reflect monitoring of particle size from day 0 to the end of MTD treatment phase. The particle size of emulsions returned from the study site was slightly higher relative to that of retained material. Since day 0 (manufacturing date) particle size of the vehicle control did not change. A significant size increase was observed for ART-207 containing particles (Table 11i).

TABLE 11i

Particle size, nm

| Material | Day of Shipment to MTD study site, (Jan. 19, 2013) | Returned from MTD study site, (Jan. 29, 2013) | Retained at Arbor Therapeutics, (Jan. 29, 2013) |
|---|---|---|---|
| 002-118-00 | 49.0 | 47.1 | 47.1 |
| 002-119-1 | 81.7 | 106.3 | 97.4 |
| 002-119-2 | 83.6 | 113.0 | 106.9 |
| 002-119-3 | 86.4 | 121.7 | 115.7 |
| 002-119-4 | 86.7 | 149.0 | 136.2 |

We extended monitoring of particle size for the emulsions used in the MTD Study, both that shipped from the MTD study site and material retained for 23 days beginning on the day of manufacture. FIG. 21 shows that particle size of the vehicle control did not change over the period of monitoring, whereas a substantial size increase was observed for ART-207 containing particles.

Although, the current lipid formulation and processing technology allow incorporation of the targeted amount of drug and reduction to an acceptable particle size, the stability of the particles obtained remains an issue. Substantial size increase over time was observed for all drug containing lipid formulations. The formulated ART-207 demonstrated efficacy, selectivity and absence of apparent toxic side effect in the MTD (ATL-1 and 2) Studies (Formal report "EVALUATION OF THE TOLERABILITY OF FORMULATED ART-207 WHEN ADMINISTERED INTRAVENOUSLY TO NONTUMORED AND TUMORED ATHYMIC NUDE MICE. Southern Research Institute, Birmingham, Ala. 35255-5305).

Evaluate the efficacy and tolerability of formulated ART-207 when administered intravenously to nontumored female athymic NCr-nu/nu mice and to female athymic NCr-nu/nu mice implanted subcutaneously with human MDA-MB-231 mammary tumor xenografts (experiment ATL-2). Paclitaxel was included as a reference compound.

Tumor Model:

Forty-six mice were implanted with fragments of the human MDA-MB-231 mammary tumor from an in vivo passage. Individual tumors of 30 animals grew to 108-600 mg in weight (108-600 mm$^3$ in size) on Day 13 after tumor fragments implantation on day of treatment initiation. Selected 30 animals with tumors were assigned to six treatment groups so that the mean tumor weights in all groups on Day 13 were as close to each other as possible (mean tumor weights ranged from 305 to 313 mg, median tumor weights ranged from 245 to 294 mg). The studies ATL-1 and ATL-2 consisted each of six groups of five nontumored mice per group for a total of 30 mice on Day 1, the first day of treatment. All treatments were administered intravenously (IV) once a day for five consecutive days (Q1D×5) beginning on Day 1. The formulated ART-207 doses of 72.6, 47.1, 35.7, and 23.7 mg/kg were 3.4x, 2.2x, 1.7x, and 1.1× molar equivalent of a paclitaxel dose of 15 mg/kg, respectively, based on the molecular weight of formulated ART-207 of 1219.6 and molecular weight of paclitaxel of 853.9.

Experiment ATL-1

Animals in Groups 1-4 were treated with formulated ART-207 at doses of 72.6, 47.1, 35.7, and 23.7 mg/kg/injection, respectively, administered to the mice by exact individual animal's body weight on each day of treatment with the injection volume being 0.21 mL/20 g of body weight. Animals in Group 5 (Emulsion control) were treated with a drug free formulation (injection volume of 0.21 mL/20 g of body weight). Animals in Group 6 were treated with paclitaxel at a dose of 15 mg/kg/injection (injection volume of 0.1 mL/10 g of body weight).

Experiment ATL-2

Animals in Groups 1-4 were treated with formulated ART-207 at doses of 72.6, 47.1, 35.7, and 23.7 mg/kg/injection, respectively, administered to the mice by exact individual animal's body weight with the injection volume being 0.21 mL/20 g of body weight. Animals in Group 5 (Emulsion control) were treated with a drug free formulation (injection volume of 0.21 mL/20 g of body weight). Animals in Group 6 were treated with paclitaxel at a dose of 15 mg/kg/injection (injection volume of 0.1 mL/10 g of body weight).

Experiment ATL-1

The IV treatment with formulated ART-207 was tolerated without deaths. The treatment resulted in maximum mean body weight losses of 1% (0.3 g), 5% (1.1 g), 1% (0.3 g), and 3% (0.6 g), when formulated ART-207 was administered at doses of 72.6, 47.1, 35.7, and 23.7 mg/kg/injection, respectively. The maximum tolerated dose for formulated ART-207 (MTD, defined as the dose that does not produce death or more than 20% body weight loss during and within 14 days of the end of the treatment) was above 72.6 mg/kg/injection in this experiment (an equivalent of 3.4x of the paclitaxel dose tested).

The IV treatment with Emulsion control on a Q1D×5 schedule (Group 5) was tolerated without deaths or body weight loss. The IV treatment with paclitaxel at a dose of 15 mg/kg/injection on a Q1D×5 schedule (Group 6) was tolerated without deaths and resulted in a maximum mean body weight loss of 6% (1.3-1.5 g). The MTD for paclitaxel was above 15 mg/kg/injection in this experiment. Change in mean body weights over the course of the experiment in all groups shown in FIG. 22.

FIG. 22. Mice were divided into 6 groups (5 mice in each group). All test articles were administered to mice for five consecutive days via intravenous (iv) injections. Group #5 received drug-free lipid formulation (black dotted line, open squares) and groups 1-4 received 23.7, 35.7, 47.1 and 72.6 mg/kg of formulated ART-207 (filled squares). Group #6 received 15 mg/kg of Paclitaxel (blue dotted line, open circles). Each point on the curves represents mean mouse weight of each Rx and vehicle treated group at the day of assessment. The mean group cutoff is two animals per group. In the graph Day 13 is defined as Day 0 or the day of the first treatment.

Experiment ATL-2

The human MDA-MB-231 mammary tumor xenografts in the Emulsion control group (Group 5) grew progressively in all five mice. The animals had an increase in weight. However, the mouse weight corrected for the weight of tumor did not significantly change over the course of study (FIG. 23). One animal (animal 1) was euthanized on Day 26 due to tumor ulceration.

The IV treatment with formulated ART-207 at doses of 72.6, 47.1, 35.7 and 23.7 mg/kg/injection on a Q1D×5 schedule (Groups 1-4, respectively) was tolerated without deaths. Administration of formulated ART-207 at a dose of 72.6 mg/kg/injection resulted in a maximum mean body weight loss of 4% (0.9 g), observed on Days 26 and 28. Animals in the groups treated with formulated ART-207 at three lower doses gained weight over the experiment. It is worth mentioning that mean mouse weight corrected for the weight of tumor did not significantly change over the course of study (FIG. 23). The MTD for formulated ART-207 was above 72.6 mg/kg/injection in this experiment (an equivalent of 3.4x of the paclitaxel dose tested).

The treatment with formulated ART-207 was very effective in the suppression of the tumor growth. Administration of formulated ART-207 at all four doses tested resulted in a dose-dependent, statistically significant inhibition of the growth of the human MDA-MB-231 mammary tumor xenografts. The treatment with a dose of 72.6 mg/kg/injection produced two complete tumor regressions, with one animal remaining tumor-free on Day 47, the day of study termination. Growth of the tumors was statistically different from the growth of the tumors in the Emulsion control group when individual animals' times to reach two tumor mass doublings were compared (see also formal SRI report). Tumor growth continued to be inhibited after the end of the treatment. Three out of five tumors in the group treated with a dose of 72.6 mg/kg/injection continued to regress until the study was terminated, while tumors in the rest of the groups started to grow back at different times post treatment in a dose response manner, higher doses delayed regrowth longer.

The IV treatment with paclitaxel at a dose of 15 mg/kg/injection on a Q1D×5 schedule (Group 6) was toxic, resulting in death of two out of five animals (with both deaths occurring on Day 19) and two more animals being euthanized (on Days 20 and 21) due to being moribund. The treatment resulted in a mean body weight loss of 1% (0.3 g) on the day of the last treatment, Day 17 but individual animals lost more weight prior to death. The MTD of paclitaxel was below 15 mg/kg/injection in this experiment. Tumor of the surviving animal responded to the treatment and regressed in weight from 180 mg on Day 13 to 32 mg on Day 47. Change in mean body weights over the course of the experiment in all groups is presented graphically in FIG. 23.

FIG. 23. Mice were divided into 6 groups (5 mice in each group). All test articles were administered to mice for five consecutive days via intravenous (iv) injections. Group #5 received drug-free lipid formulation (black dotted line, open squares) and groups 1-4 received 23.7, 35.7, 47.1 and 72.6 mg/kg of formulated ART-207 (filled squares). Group #6 received 15 mg/kg of Paclitaxel (blue dotted line, open circles). Each point on the curves represents mean mouse weight of each Rx and vehicle treated group at the day of assessment. Tumored mouse weight was corrected for the weight of tumor. The mean group cutoff is two animals per group. In the graph Day 13 is defined as Day 0 or the day of the first treatment.

Response of the SC implanted human MDA-MB-231 mammary tumor xenografts to the treatment with formulated ART-207, Emulsion control, and paclitaxel is presented graphically in FIG. 24 as a mean tumor weight change.

FIG. 24. Mice were divided into 6 groups (5 mice in each group). All test articles were administered to mice for five consecutive days via intravenous (iv) injections. Group #5 received drug-free lipid formulation (black dotted line, open squares) and groups 1-4 received 23.7, 35.7, 47.1, and 72.6 mg/kg of formulated ART-207 (filled squares). Group #6 received 15 mg/kg of Paclitaxel (blue dotted line, open circles). "Day 0" (dotted line) represents the average tumor weight for all groups assessed at the first day of treatment. Each point on the curves represents mean tumor weight of each Rx and vehicle treated group at the corresponding day of assessment. The mean group cutoff is two animals per group. In the graph Day 13 is defined as Day 0 or the day of the first treatment.

Animal Survival (FIG. 25). In the group treated with Paclitaxel 4 of 5 animals died before day 11 due to apparent toxicity of the drug. In the vehicle treated group 4 of the animals had to be euthanized on day 18 due to extremely large tumor size. In the group treated with the lowest (23.7 mpk) dose of formulated ART-207, 4 animals were euthanized due to large tumors but on day 30. The animals treated with 35.7, 47.1 and 72.6 mpk of ART-207 were alive and active and no weight loss was observed during the entire course of the study in contrast to the animals dosed with Paclitaxel. Some mice in the 72.6 mpk of ART-207 group became tumor free at day 11 post dosing and stayed tumor free until the end of the study (FIG. 25).

FIG. 25. Mice were divided into 6 groups (5 mice in each group). All test articles were administered to mice for five consecutive days via intravenous (iv) injections starting from day 0. Group #5 received drug-free lipid formulation (black dotted line, open squares) and groups 1-4 received 23.7, 35.7, 47.1 and 72.6 mg/kg of formulated ART-207 (filled squares). Group #6 received 15 mg/kg of Paclitaxel (blue dotted line, open circles). The outcome of this proof-of-principle in vivo study is indicative of targeted delivery and efficacy of our compound with no apparent toxic side effects. This was the major cause for not reaching maximum tolerated dose in this study.

Experiment 12. Preparation of ART-207 (Lot# AW-001-243) containing emulsion.

Testing the effect of the added P188 (0.25%, V/W) on particle size and stability. P188 was added to previously processed emulsion lot #002.121.4 (see master Table 3) to final concentration 0.25% (V/W) while stirring on magnetic stirring plate. The mixture was further processed in microfluidizer.

TABLE 12a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 15 Jan. 2013 | 002.115.3 | TSPM | 5185 | 1393 | 70 | 213 | 10 | 10 | 671 | 0 | 0 | 0 |

TABLE 12b

| Ratios for major formulation components. | | | |
|---|---|---|---|
| TG/ART-207 | PC/ART-207 | PC/TG | FC/CE |
| 2.07 | 7.72 | 3.72 | 0.33 |

Coarse suspension was prepared and MF processed (lot#002.122.0).

TABLE 12c

Resultant particle size, ART-207 content, and particle stability.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 22 Jan. 2013 | 002.122.0 | 80 | 5.63 | 83.9 | 57 | 197 |

MFP. In FIG. 26, particle size reaches R1 at ~71 nm after 30 min of processing at ~60° C. MFP was stopped and material was sterile filtered. Increase of particle size from 71 to 80 nm was observed after filtration.

HPLC Analysis. ART-207 content in resultant emulsion determined by HPLC (Taxane_Test.M, Rev 0) was 5.63 mg/ml. These data indicate that 83.9% of the drug used for preparation of this formulation was incorporated into lipid particles (Table 12c). The lower ART-207 concentration in resultant emulsion could be explained by additional MF processing and possible dilution with buffer used to equilibrate the MF prior to processing. Particle size analysis of ART-207 containing formulation. The resultant ART-207 containing emulsion was unstable. FIG. 27 and Table 12c show that particle size increased from 80 to 197 nm over 57 days.

Result suggests that addition of 0.25% of P188 at post-coarse emulsion step does not improve the stability of the resultant formulation.

Experiment 13. Preparation of ART-207 (Lot# AW-001-243) containing emulsion. Testing the effect of P188 (0.25%, V/W), decreased TG/ART-207 ratios, and further decrease of CE and subsequently TC on resultant particle size and stability. P188 was added to the TSPM.

TABLE 13a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 22 Jan. 2013 | 002.122.1 | TSPM | 5085 | 501 | 70 | 148 | 10 | 10 | 500 | 256 | 0 | 0 |

TABLE 13b

Ratios for major formulation components.

| TG/ART-207 | PC/ART-207 | PC/TG | FC/CE |
|---|---|---|---|
| 1.00 | 10.17 | 10.15 | 0.47 |

Coarse suspension was prepared and MF processed (lot#002.123.11).

TABLE 13c

Resultant particle size, ART-207 content, and particle stability.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 23 Jan. 2013 | 002.123.11 | 68 | 3.71 | 74.2 | 56 | 73 |
| 23 Jan. 2013 | 002.123.12 | 57 | 3.71 | 74.2 | 30 | 67 |
| 23 Jan. 2013 | 002.123.13 | 69 | 3.71 | 74.2 | 56 | 70 |

MFP. In FIG. 28, particle size reaches R1 at ~68 nm after 20 mm of processing at ~60° C. MFP was stopped, sample was collected and filtered (Table 13c). Filtration did not affect the particle size. The rest of material was processed further at ~20° C. for 10 min (FIG. 28). This resulted in a decrease of the particle size to 64 nm and was considered as R2. MFP was stopped, sample was collected and filtered (Table 13c). Filtration resulted in significant decrease of the particle size to 57 nm. The temperature was raised to 60° C. and remainder of material was processed for 20 min. Further processing resulted in particle size increase to 66 nm and reached the R3. MFP was stopped and remainder of material collected and filtered (Table 13c). No significant size increase was observed after filtration.

HPLC Analysis. ART-207 content was determined only in emulsion lot#002.123.13 (Taxane_Test.M, Rev 0) and was equal to 3.71 mg/ml. Data shows that 74.2% of the drug used for preparation of this formulation was incorporated into lipid particles (Table 13c). Particle size analysis of ART-207 containing formulation. FIG. 29 and Table 13c shows that over 56 days, particle size of lot#002.123.11 increased from 68 to 73 nm, and lot#002.123.13 increased from 69 to 70 nm over 56 days. Particle size of the emulsion lot#002.123.12 increased from 57 to 67 nm over 30 days. a) Decreasing TG/ART-207 ratio by lowering TG content and subsequently raising PC/TG ratio; b) lowering CE and subsequently total cholesterol content; and c) addition of P188 (0.25%, V/W) at the TSPM step resulted in fairly stable emulsions. Without P188, similar manipulation of TG/ART-207 and PC/TG ratios (experiment #7) resulted in an unstable emulsion. Addition of P188 to TSPM with higher TG/ART-207 and lower PC/TG ratios (experiment #8 and 12) also failed to produce stable emulsions.

In FIGS. 28 and 29, stopping the MF processing at 60° C. (lot #002.123.11 and 002.123.13) resulted in stable emulsions with 68-69 nm particle size, whereas the 20° C. end point (lot#002.123.12) resulted in initially smaller ~57 nm particles that shortly increased their size to ~66 nm and stabilized at this level. The ART-207 content measured in resultant emulsion lot#002.123.13 was notably lower (3.7 mg/ml) than in preparations with higher TG/ART-207 and lower PC/TG ratios (experiments #4-5, and 10-12), (4.8-6.1 mg/ml). In contrast to preparations in experiments #4-5, and 10-12, the resultant material obtained in this experiment (lot#002.123.13) was extremely stable.

ART-207 may have destabilizing effect on lipid particles, and therefore stability achieved in lot#002.123.13 is due to lower drug content. Comparison of lot#002.123.13 stability to that of emulsions obtained in experiments #3, 6 and 7 (with similar or even lower drug content) clearly demonstrates improved stability of the current material.

Experiment suggests that TG/ART-207 and PC/TG ratios, addition of 0.25% of P188 at TSPM step, and processing temperature are important in determining stability of the resultant emulsion preparations, but shows that manipulations lead to lower drug incorporation. To achieve both high drug content and stability of lipid formulations, gradual increase of TG/ART-207 ratio above 1.0 and addition of shorter chain phospholipid can be considered.

Experiment 14. Preparation of ART-207 (Lot# AW-001-243) containing emulsion.

Testing the effect of DMPC and decreased TG/ART-207 ratio on ART-207 incorporation, resultant particle size and stability of P188 containing formulation. DMPC was added to the TSPM instead of mass equivalent of PC.

TABLE 14a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 24 Jan. 2013 | 002.125.1 | TSPM | 4085 | 511 | 70 | 150 | 10 | 10 | 503 | 250 | 1053 | 0 |

TABLE 14b

Ratios for major formulation components.

| TG/ART-207 | PC/ART-207 | PC/TG | FC/CE |
|---|---|---|---|
| 1.02 | 10.21 | 10.05 | 0.47 |

Coarse suspension was prepared and MF processed (lot#002.125.2).

TABLE 14c

Resultant particle size, ART-207 content, and particle stability.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 25 Jan. 2013 | 002.125.21 | 67 | 3.97 | 79.0 | 54 | 62 |
| 25 Jan. 2013 | 002.125.22 | 66 | 3.97 | 79.0 | 54 | 64 |

MFP. In FIG. 30, particle size reaches R1 at ~99 nm after 10-20 min of processing at ~60° C. Temperature was lowered to ~20° C. Further processing at lower temperatures resulted in increase of particle size to ~119 nm (R2). Gradual raising the temperature to ~60° C. resulted in particle size decrease to 84 nm after 60 mm of processing and reaching R3. A sample was collected and filtered (Table 14c). Filtration resulted in significant decrease of the particle size from 84 to 67 nm. To investigate effect of increased P188 concentration on processing and stability, P188 was added to the rest of the material to final concentration 0.5% (V/W). Further processing at ~60° C. for 30 more minutes did not result in the particle size change. MFP was stopped, sample was collected and filtered (see also Table 14c). Filtration resulted in decrease of the particle size from 83 to 66 nm.

HPLC Analysis. ART-207 content was determined only in emulsion lot#002.125.22 (Taxane_Test.M, Rev 0) and was equal to 3.97 mg/ml. Data indicate that 79% of the drug used for preparation of this formulation was incorporated into lipid particles (Table 14c). Particle size analysis of ART-207 containing formulation. In FIG. 31 and Table 14c, over 54 days no particle size increase was observed for lot#002.125.21 or lot#002.125.22.

Addition of shorter chain phospholipid (DMPC) along with P188 and lower TG/ART-207 ratio resulted in stable emulsions. The increase of P188 to 0.5% (V/W) does not affect the stability of resultant emulsion. The ART-207 content measured in resultant emulsion lot#002.123.22 was higher and equal to 3.97 mg/ml vs. 3.7 mg/ml observed in experiment #13 where no DMPC was added to formulation.

Experiment 15. Preparation of drug-free emulsion. Investigating the effect of P188 on particle size and stability of drug-free high phospholipid emulsions.

TABLE 15a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 8 Feb. 2013 | 002.131.1 | TSPM | 5190 | 701 | 69 | 148 | 10 | 10 | 0 | 251 | 0 | 0 |

TABLE 15b

Ratios for major formulation components.

| TG/ART-207 | PC/ART-207 | PC/TG | FC/CE |
|---|---|---|---|
| N/A | N/A | 7.40 | 0.47 |

Coarse suspension was prepared and MF processed (lot#002.131.2).

TABLE 15c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size nm |
|---|---|---|---|---|---|---|
| 9 Feb. 2013 | 002.131.2 | 42 | N/A | N/A | 39 | 49 |

MFP. In FIG. 32, particle size reached 41 nm after 20 min of processing at ~60° C. MFP was stopped and filtered. No particle size change was observed after filtration.

HPLC Analysis. ART-207 content in resultant emulsion determined by HPLC Taxane_Test.M, Rev 1) was below detection limit. Particle size analysis of drug-free formulation. The resultant emulsion was stable for 39 days (FIG. 33 and Table 15c). In FIG. 33, particle size increased from 42 to 45 nm in the first two days. From day 3 to day 39 the increase in particle from 45 to 49 nm.

The initial particle size increase in the first 2-3 days was observed for almost all preparations and may reflect equilibrating and stabilizing of emulsion preparations after high pressure and often different from the ambient temperature processing.

Experiment 16. Preparation of ART-207 (Lot# AW-004-13) containing emulsion.

Testing the effect of gradual increase of TG/ART-207 ratio (from 1 to 1.35) on ART-207 incorporation, particle size and stability of formulation.

TABLE 16a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 9 Feb. 2013 | 002.134.1 | TSPM | 5220 | 697 | 69 | 149 | 10 | 10 | 529 | 250 | 0 | 0 |

TABLE 16b

Ratios for major formulation components.

| TG/ART-207 | PC/ART-207 | PC/TG | FC/CE |
|---|---|---|---|
| 1.32 | 9.87 | 7.49 | 0.46 |

Coarse suspension was prepared and MF processed (lot#002.134.2).

TABLE 16c

Resultant particle size, ART-207 content, and particle stability.

| Manufacturing Date | Lot# | Particle size by intensity, nm | ART-207 Content, mg/ml | ART-207 Recovery, % | Formulation Stability Days past mfg | Formulation Stability Particle size nm |
|---|---|---|---|---|---|---|
| 9 Feb. 2013 | 002.134.2 | 76 | 4.71 | 89.0 | 39 | 84 |

MFP. In FIG. 34, particle size reaches R1 at ~81 nm after 30 mm of processing at ~60° C., and the temperature was lowered to ~20° C. Further processing at lower temperatures resulted in increase of particle size to ~84 nm (R2). Raising the temperature to ~60° C. resulted in decrease of the particle size to 76 nm after 50 min of processing and reaching R3. The sample was collected and filtered. No change of the particle size was observed after filtration.

HPLC Analysis. ART-207 content was determined in resultant emulsion (Taxane_Test.M, Rev 1) and was equal to 4.71 mg/ml. Data indicate that 89% of the drug used for preparation of this formulation was incorporated into lipid particles (Table 16c). Particle size analysis of ART-207 containing formulation. In FIG. 35, initial rise of the particle size from 76 to 82 nm takes place in the first two days, whereas during next 37 days particle size did not change.

Thus, increasing of TG/ART-207 ratio form 1 to 1.35 resulted in increased ART-207 incorporation capacity of formulation without affecting its stability. The resultant particles were larger than particles formed at lower TG/ART-207 ratio.

Experiment 17. Preparation of ART-207 (Lot# AW-004-13) containing emulsion.

Testing effect of DMPC and an increase of TG/ART-207 ratio (from 1 to 1.34) on ART-207 incorporation, particle size, and stability of resultant emulsion. DMPC was added to the TSPM instead of mass equivalent of PC.

TABLE 17a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 11 Feb. 2013 | 002.135.1 | TSPM | 4180 | 705 | 68 | 147 | 10 | 10 | 525 | 300 | 1098 | 0 |

TABLE 17b

Ratios for major formulation components.

| TG/ART-207 | PC/ART-207 | PC/TG | FC/CE |
|---|---|---|---|
| 1.34 | 10.05 | 7.49 | 0.46 |

Coarse suspension was prepared and MF processed (lot#002.136.2).

TABLE 17c

Resultant particle size, ART-207 content, and particle stability.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 12 Feb. 2013 | 002.136.21 | 58 | 4.30 | 81.9 | 36 | 61 |
| 12 Feb. 2013 | 002.136.22 | 42 | 4.22 | 80.4 | 36 | 55 |
| 12 Feb. 2013 | 002.136.23 | 59 | 4.50 | 85.7 | 36 | 60 |

MFP. In FIG. 36, particle size reached ~70 nm after 10 mm of processing at ~60° C. MFP was stopped, sample was collected and filtered (Table 17c). Decrease in the particle size from 70 to 58 nm was observed after sterile filtration. Although the first resistance point (R1) was not reached, the particle size was small enough to collect the sample for stability assay. Further processing of remainder material at 60° C. did not result in change of particle size (R1). The temperature was lowered to ~20° C. Processing at lower temperatures for 30 more minutes did not result in change in particle size (R2). MFP was stopped, sample was collected and filtered (see Table 17c). Filtration resulted in dramatic decrease of the particle size from 68 to 42 nm. The temperature was raised to 60° C. and remainder of material was processed for additional 20 min. Additional processing resulted in decrease of particle size from 68 to 66 nm and reached the R3. MFP was stopped and remainder of material collected and filtered (Table 17c). Decrease of particle size from 66 to 59 nm was observed after filtration.

HPLC Analysis. ART-207 content was determined in all resultant emulsions (Taxane_Test.M, Rev 1) and was equal to 4.3 mg/ml (lot#002.136.21), 4.22 mg/ml (lot#002.136.22), and 4.5 mg/ml (lot#002.136.23). Data indicate that 81.9, 80.4, and 85.7% of the drug used for preparation of this formulation was incorporated into lipid particles of lots 002.136.21, 002.136.22 and 002.136.23, respectively (Table 17 c).

Particle size analysis of ART-207 containing formulation. In FIG. 37, after initial 1-3 nm increase of the particle size observed in the first two days for the lots #002.136.21 and 002.136.23, particle size did not change for the next 34 days. The particle size of emulsion lot #002.136.22 increased by 7 nm during the first two days of storage, and from 49 to 55 nm over 34 days. All resultant emulsions can be characterized as stable.

Although processing at higher temperatures resulted in bigger particles relative to lower temperature processed material, the stability of material processed at ~60° C. is higher compared to ~20° C. processed emulsions. Lots #002.136.21 and 002.136.23 processed at 60° C. were markedly more stable over the entire course of monitoring, whereas lot #002.136.22 (processed at ~20° C.) started increasing particle size from 42 to 53 nm on the day 1 and stabilized only on day 10 (FIG. 37). Increasing of TG/ART-207 ratio form 1 to 1.34 and addition of DMPC resulted in smaller particles and essentially the same ART-207 incorporation capacity and stability of the resultant formulation relative to emulsion obtained in experiment #16.

Experiment 18. Preparation of drug-free lipid emulsion.

Investigate effect of phosphotidyl serine (PS) on particle size and stability of drug-free formulation. PS may be used as a formulation component instead of DMPC and P188.

TABLE 18a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 14 Feb. 2013 | 002.137.1 | TSPM | 5360 | 1408 | 70 | 150 | 10 | 10 | 0 | 0 | 0 | 200 |

TABLE 18b

Ratios for major formulation components.

| TG/ART-207 | PC/ART-207 | PC/TG | FC/CE |
|---|---|---|---|
| N/A | N/A | 3.95 | 0.47 |

Coarse suspension was prepared and MF processed (lot#002.137.3).

TABLE 18c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size nm |
|---|---|---|---|---|---|---|
| 15 Feb. 2013 | 002.137.3 | 49 | N/A | N/A | 33 | 51 |

MFP. In FIG. 38, particle size reached 49 nm after 20 mm of processing at ~60° C. MFP was stopped and material was filtered. No particle size change was observed after filtration.

HPLC Analysis. ART-207 content in resultant emulsion determined by HPLC (Taxane_Test.M, Rev 1) was below detection limit. Particle size analysis of drug-free formulation. The resultant emulsion was stable. No significant increase of particle size over 33 days (FIG. 39 and Table 18c).

Experiment 19. Preparation of ART-207 (Lot# AW-004-13) containing lipid emulsion. Investigating the effect of phosphotidyl serine (PS) on particle size and stability of ART-207 containing formulations. The combination of P188 and DMPC, and also lower (1.34) TG/ART-207 ratio were used in experiment #17 to achieve stability and target particle size of resultant emulsion. We also added PS to TSPM that did not contain P188 and DMPC, and had higher (2.7) TG/ART-207 ratio.

TABLE 19a

Formulation composition.

| Date | Lot# | Material | PC | TG | FC | CE | U | Vit E | ART | P188 | DMPC | PS |
|---|---|---|---|---|---|---|---|---|---|---|---|---|
| 14 Feb. 2013 | 002.137.2 | TSPM | 5390 | 1391 | 70 | 148 | 10 | 10 | 524 | 0 | 0 | 200 |

TABLE 19b

Ratios for major formulation components.

| TG/ART-207 | PC/ART-207 | PC/TG | FC/CE |
|---|---|---|---|
| 2.65 | 10.67 | 4.02 | 0.47 |

Coarse suspension was prepared and MF processed (lot#002.137.4).

TABLE 19c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size nm |
|---|---|---|---|---|---|---|
| 15 Feb. 2013 | 002.137.41 | 53 | 4.79 | 91.2 | 33 | 108 |
| 15 Feb. 2013 | 002.137.42 | 84 | 5.01 | 95.4 | 33 | 134 |
| 15 Feb. 2013 | 002.137.43 | 54 | 4.89 | 93.1 | 33 | 183 |

MFP. In FIG. 40, particle size reached R1 at ~86 nm after 30 min of processing at ~60° C. Since particle size was far from targeted no sample was collected, and temperature was lowered to ~20° C. Particle size decrease from 86 to 50 nm was observed during further processing at ~20° C. MFP was stopped, a sample was collected and filtered (Table 19c). No change in particle size was observed after filtration. Although the first resistance point (R1) was not reached, the particle size was small enough to collect the sample for stability assay (R2). The temperature was raised to 60° C. and the remainder of material was processed for 20 more minutes. There was increase of particle size from 50 to 82 nm and reached the R3. MFP was stopped, sample was collected and filtered (FIG. 43 and Table 19c). No change in particle size was observed after filtration. Temperature was lowered to ~25° C. and further processing of remainder material for 20 min resulted in particle size decrease from 82 to 53 nm and reached R4. MFP was stopped, a sample was collected and sterile filtered (FIG. 40 and Table 19c). No change in particle size was observed after filtration.

HPLC Analysis. ART-207 content was determined in all resultant emulsions (Taxane_Test.M, Rev 1) and was equal to 4.79 mg/ml (lot#002.137.41), 5.01 mg/ml (lot#002.137.42), and 4.89 mg/ml (lot#002.137.43). Data indicate that 91.2, 95.4 and 93.1% of the drug used for preparation of this formulation was incorporated into lipid particles of lots 002.137.41, 002.137.42, and 002.137.43, respectively (Table 19c).

Particle size analysis of ART-207 containing formulation. FIG. 41 and Table 19c show that regardless of high ART-207 incorporation capacity, all resultant emulsions were unstable. After 33 days, the particle size increased in all processed lots.

Although processing at higher temperatures results in bigger particles relative to lower temperature processing, the stability of material processed at ~60° C. is higher compared to ~20° C. processed emulsions. For example, lot#002.137.42 processed at 60° C. was relatively stable for 18 days of storage, whereas lots #002.137.41 and 002.137.43 were increasing particle size from day 1 (FIG. 41). Drug incorporation capacity of this PS containing formulation was high probably due to high (2.7) TG/ART-207 ratio. Addition 2.5% (W/W) of negatively charged PS to material with high TG/ART-207 ratio does not improve the stability of resultant emulsion.

Experiment 20. Preparation of drug-free emulsion. Investigate effect of P188, DMPC, and low TG on particle size and stability of drug-free formulation.

TABLE 20a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 21 Feb. 2013 | 002.139.1 | TSPM | 4210 | 700 | 70 | 150 | 10 | 10 | 0 | 297 | 1060 | 0 |

TABLE 20b

Ratios for major formulation components.

| TG/ART-207 | PC/ART-207 | PC/TG | FC/CE |
|---|---|---|---|
| N/A | N/A | 7.53 | 0.47 |

Coarse suspension was prepared and MF processed (lot#002.137.3).

TABLE 20c

Particle size, ART-207 content, and particle stability of resultant emulsion.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 21 Feb. 2013 | 002.139.2 | 38 | N/A | N/A | 27 | 43 |

MFP. FIG. 42 shows that particle size reached 39 nm after 20 min of processing at ~60° C. MFP was stopped and filtered. No particle size change noted after filtration.

HPLC Analysis. ART-207 content in resultant emulsion determined by HPLC (Taxane_Test.M, Rev 1) was below detection limit. Particle size analysis of drug-free formulation. The resultant emulsion was stable. No significant increase of particle size from 38 to 42.5 nm observed during 27 days (FIG. 43 and Table 20 c).

Experiment 21. Preparation of ART-207 (Lot# AW-004-13) containing emulsion. Repeat of experiment #17, to confirm favorable effect of DMPC/P188 and 1.34 TG/ART-207 ratio on ART-207 incorporation, particle size, and stability of resultant emulsion.

TABLE 21a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 21 Feb. 2013 | 002.140.1 | TSPM | 4230 | 703 | 70 | 150 | 10 | 10 | 527 | 298 | 1080 | 0 |

TABLE 21b

Ratios for major formulation components.

| TG/ART-207 | PC/ART-207 | PC/TG | FC/CE |
|---|---|---|---|
| 1.33 | 10.08 | 7.55 | 0.47 |

Coarse suspension was prepared and MF processed (lot#002.140.2).

TABLE 21c

Particle size, ART-207 content, and particle stability of resultant emulsion.

| Manufacturing Date | Lot# | Particle size by intensity, nm | ART-207 Content, mg/ml | ART-207 Recovery, % | Formulation Stability Days past mfg | Formulation Stability Particle size nm |
|---|---|---|---|---|---|---|
| 21 Feb. 2013 | 002.140.21 | 58 | 4.42 | 84.2 | 27 | 58 |
| 21 Feb. 2013 | 002.140.22 | 46 | 4.10 | 78.1 | 27 | 54 |
| 21 Feb. 2013 | 002.140.23 | 59 | 4.50 | 85.7 | 27 | 58 |
| 21 Feb. 2013 | 002.140.24 | 49 | 4.35 | 82.9 | 27 | 55 |

MFP. In FIG. 44, particle size reached R1 at ~68 nm after 20 min of processing at ~60° C. MFP was stopped, sample was collected and filtered (see also Table 21c). Decrease of particle size from 68 to 58 nm noted after filtration. The temperature was lowered to ~23° C. and the remainder of material was processed for 20 more minutes. This resulted in decrease of particle size 65 nm and reached the R2. MFP was stopped, a sample was collected and filtered (FIG. 44 and Table 21c). Decrease of particle size from 65 to 46 nm noted after filtration. Then temperature was raised to ~60° C. and further processing of remainder material for 20 min resulted in increase of particle size 68 nm and reached R3. MFP was stopped, a sample was collected and filtered (FIG. 44 and Table 21c). Decrease of particle size from 68 to 59 nm was observed after filtration. Temperature was lowered to ~20° C. and the remainder of material was processed for an additional 20 mm. This did not change the particle size reached at R4. MFP was stopped, sample was collected and filtered (FIG. 44 and Table 21c). Decrease of particle size from 67 to 49 nm after filtration.

HPLC Analysis. ART-207 content was determined in all resultant emulsions (Taxane_Test.M, Rev 1) and was equal to 4.42 mg/ml (lot#002.140.21), 4.1 mg/ml (lot#002.140.22), 4.5 mg/ml (lot#002.140.23), and 4.35 mg/ml (lot#002.140.24). Data indicate that 84.2, 78.1, 85.7 and 82.9% of the drug used for preparation of this formulation was incorporated into lipid particles of lots 002.140.21, 002.140.22, 002.140.23, and 002.140.24 respectively (Table 21c).

Particle size analysis of ART-207 containing formulation. In FIG. 45, emulsion lots #002.140.21 and 002.140.23 processed at 60° C. were highly stable. An initial ~5-7 nm particle size increase (in the first 5 days of storage) was observed in Lots #002.140.22 and 002.140.24. Both lots stabilized at ~53-55 nm by day 6.

Processing at higher temperatures results in bigger particles relative to lower temperature processing, stability of material processed at ~60° C. was higher compared to ~20° C. processed emulsions. In terms of particle size and stability, this result is similar to outcome of experiment #17. Drug incorporation capacity of lot #002.140.2 formulation was similar to that obtained in other experiments with similar TG/ART-207 ratios. The range of TG/ART-207 ratios ~1.3-1.4 results in reproducible ART-207 incorporation capacity and stability of resultant emulsions.

Preparation of drug-free and Art-207 containing formulations for efficacy and stability studies Experiment 22. Preparation of drug-free emulsion—Vehicle Control. Preparation of drug-free emulsion for efficacy study.

TABLE 22a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 13 Mar. 2013 | 002.150.1 | TSPM | 4344 | 700 | 71 | 151 | 11 | 10 | 0 | 303 | 1076 | 0 |

TABLE 22b

| Ratios for major formulation components. | | | |
|---|---|---|---|
| TG/ART-207 | PC/ART-207 | PC/TG | FC/CE |
| N/A | N/A | 7.74 | 0.47 |

Coarse suspension was prepared and MF processed (lot#002.151.5).

TABLE 22c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 14 Mar. 2013 | 002.151.5 | 37 | N/A | N/A | 42 | 47 |

MFP. In FIG. 46 that particle size reached 41 nm after 20 mm of processing at ~60° C. MFP was stopped and material filtered. Decrease of particle size from 41 to 37 nm was observed after filtration.

HPLC Analysis. ART-207 content in resultant emulsion determined by HPLC (Taxane_Test.M, Rev 2) was below detection limit. Particle size analysis of drug-free formulation. The resultant emulsion was stable for 33 days. In FIG. 50, particle size did not change for 33 days. For the next 9 days (42 days total) particle size increased to 47 nm (FIG. 47 and Table 22c).

Experiment 23. Preparation of ART-207 (Lot# AW-004-24) containing emulsion.

Manufacture of ART-207 containing emulsion preparation for efficacy study.

TABLE 23a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 13 Mar. 2013 | 002.150.4 | TSPM | 4203 | 699 | 70 | 150 | 10 | 10 | 532 | 300 | 1083 | 0 |

TABLE 23b

| Ratios for major formulation components. | | | |
|---|---|---|---|
| TG/ART-207 | PC/ART-207 | PC/TG | FC/CE |
| 1.31 | 9.94 | 7.56 | 0.47 |

150 ml of coarse suspension was prepared and MF processed (lot#002.151.8).

TABLE 23c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 14 Mar. 2013 | 002.151.8 | 62 | 5.26 | 98.9 | 42 | 67 |

MFP. In FIG. 48, particle size reaches 78 nm after 30 min of processing at ~60° C. Additional 30 mm of processing at ~60° C. did not significantly reduce the particle size and was considered as R2. The temperature was lowered to 20° C. and processed for additional 45 min. Processing at 20° C. resulted in increase of particle size and was considered as R2. MFP was stopped and material was sterile filtered. Decrease of the particle size from 76 to 61 nm was observed after filtration.

HPLC Analysis. ART-207 content in resultant emulsion determined by HPLC (Taxane_Test.M, Rev 2) was 5.26 mg/ml. Data indicate that 98.9% of the drug used for preparation of this formulation was incorporated into lipid particles (Table 23c). Particle size analysis of ART-207 containing formulation. The resultant ART-207 containing emulsion was stable. In FIG. 49 and Table 23c, particle size did not change over 33 days. During the next 9 days (42 days total) a increase of ~3.5-4 nm was observed.

MF processing of formulation with TG/ART-207 ratio equal 1.31 resulted in stable emulsion with 98.9% ART-207 incorporation capacity.

Experiment 24. Preparation of ART-207 (Lot# AW-004-24) containing backup emulsion for efficacy study. Manufacturing ART-207 containing emulsion with increased TG/ART-207 ratio to 1.4 as a candidate for efficacy study.

TABLE 24a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 15 Mar. 2013 | 002.152.1 | TSPM | 4277 | 698 | 70 | 150 | 10 | 10 | 501 | 301 | 1067 | 0 |

TABLE 24b

Ratios for major formulation components.

| TG/ART-207 | PC/ART-207 | PC/TG | FC/CE |
|---|---|---|---|
| 1.39 | 10.67 | 7.66 | 0.47 |

130 ml of coarse suspension was prepared and MF processed (lot#002.153.1).

TABLE 24c

Particle size, ART-20 content, and particle stability of resultant emulsion.

| | | Particle size | ART-207 | | Formulation Stability | |
|---|---|---|---|---|---|---|
| Manufacturing Date | Lot# | by intensity, nm | Content, mg/ml | Recovery, % | Days past mfg | Particle size nm |
| 15 Mar. 2013 | 002.153.1 | 66 | 4.68 | 93.5 | 41 | 69 |

MFP. FIG. 50 shows that particle size reaches 78 nm after 39 min of processing at ~60° C. Temperature was lowered to 20° C. and material was processed for additional 39 min MF processing at 20° C. did not result in particle size decrease and was considered as R2. MFP was stopped and filtered. Decrease of the particle size from 78 to 66 nm noted after filtration.

HPLC Analysis. ART-207 content in resultant emulsion determined by HPLC (Taxane_Test.M, Rev 2) was 4.68 mg/ml. Data indicate that 93.5% of the drug used for preparation of this formulation was incorporated into lipid particles (Table 24c).

Particle size analysis of ART-207 containing formulation. The resultant ART-207 containing emulsion was stable. FIG. 51 and Table 24c show that particle size did not significantly change over 41 days.

MF processing of formulation with TG/ART-207 ratio equal 1.39 resulted in stable emulsion with 93.5% ART-207 incorporation capacity.

Experiment 25. Preparation of ART-207 (Lot# AW-004-24) containing backup emulsion for efficacy study. To manufacture ART-207 containing emulsion with further increased TG/ART-207 ratio to 1.5 as a candidate for efficacy study.

TABLE 25a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 15 Mar. 2013 | 002.152.2 | TSPM | 4320 | 698 | 70 | 150 | 10 | 10 | 475 | 304 | 1163 | 0 |

TABLE 25b

Ratios for major formulation components.

| TG/ART-207 | PC/ART-207 | PC/TG | FC/CE |
|---|---|---|---|
| 1.47 | 11.54 | 7.85 | 0.47 |

130 ml of coarse suspension was prepared and MF processed (lot#002.153.2).

TABLE 25c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 15 Mar. 2013 | 002.153.2 | 53 | 4.38 | 92.2 | 49 | 62 |

MFP. In FIG. 52, particle size reaches 72 nm after 52 min of processing at ~60° C. Then temperature was lowered to 20° C. and material was processed for additional 26 min. MF processing at 20° C. resulted in slight decrease of the particle size to 66 nm and reaching R2. MFP was stopped and material was sterile filtered. Decrease of the particle size from 66 to 53 nm was observed after filtration.

HPLC Analysis. ART-207 content in resultant emulsion determined by HPLC (Taxane_Test.M, Rev 2) was 4.38 mg/ml. 92.2% of the drug used for preparation of this formulation was incorporated into lipid particles (Table 25c). Particle size analysis of ART-207 containing formulation. The resultant ART-207 containing emulsion was fairly stable. FIG. 53 and Table 25c show that particle size increased from 53 to 62 nm over 49 days.

MF processing of formulation mix with TG/ART-207 ratio equal 1.47 resulted in stable emulsion with 92.2% ART-207 incorporation capacity. Selection of emulsions for efficacy study. ART-207 containing emulsion lot #002.151.8 was selected for efficacy study based on particle size (62 nm) and ART-207 content (5.26 mg/ml). Drug-free emulsion lot #002.151.5 was selected for efficacy study as a vehicle control (Table 25a and 25d).

TABLE 25d

Resultant emulsions on the day of manufacturing. Particle size, ART-207 content, total solids and lipid concentration (W/V).

| Date | Lot# | Material | Particle size, nm | ART-207, HPLC mg/ml | TS % | TL % |
|---|---|---|---|---|---|---|
| 14 Mar. 2013 | 002.151.5 | Emulsion | 37 | N/A | 6.7 | 6.3 |
| 14 Mar. 2013 | 002.151.6 | Emulsion | 38 | N/A | 7.8 | |
| 14 Mar. 2013 | 002.151.7 | Emulsion | 72 | 5.30 | 7.1 | 7.4 |
| 14 Mar. 2013 | 002.151.8 | Emulsion | 62 | 5.26 | 7.1 | 6.2 |
| 15 Mar. 2013 | 002.153.1 | Emulsion | 66 | 4.68 | 7.1 | 6.3 |
| 15 Mar. 2013 | 002.153.2 | Emulsion | 53 | 4.38 | 7.2 | 6.4 |

Targeted doses of ART-207. The projected doses of formulated ART-207 for the efficacy study were the following: 105.2, 78.9 and 52.6 mg per kg (mpk). All test articles were administered to mice via intravenous (iv) injections. The injection volumes to achieve projected doses are shown in Table 25e.

TABLE 25e

ART-207 content, projected doses, and injection volumes.

| Lot# | Material | ART-207 mg/ml | Dose, mpk | Injection Volume, ml (per 20 g of mouse weight) |
|---|---|---|---|---|
| 002.151.5 | Vehicle Control | BDL | N/A | 0.4 |
| 002.151.8 | Formulated ART-207 | 5.26 | 52.6 | 0.2 |
| 002.151.8 | Formulated ART-207 | 5.26 | 78.9 | 0.3 |
| 002.151.8 | Formulated ART-207 | 5.26 | 105.2 | 0.4 |

Approximately 45 ml of lot#002.151.5 and ~(≥) 80 ml of lot #002.151.8 were shipped to the study site: Lot#002.151.5—Drug-free formulation (vehicle control); Lot#002.151.8—Formulated ART-207 (5.26 mg/ml). ~10 ml samples of each lot were retained.

The Efficacy study consisted of two major phases similar to those described above for the MTD study: Material remaining was returned to Arbor Therapeutics after the end of the treatment phases. ART-207 content was assessed (Taxane_Test.M, Rev 2) for all formulations used in the efficacy study. The assessment of returned material was carried out side by side with material retained. Table 25e shows that material evaluated on the day of manufacturing, returned from the study site, and material retained have similar drug content in all tested lots. The data indicate good stability of formulated ART-207 and also proper material handling at the research sites.

TABLE 25e

HPLC Analyses of ART-207 Content, mg/mL

| Material | On the day of mfg | Returned Material | Retained Material |
|---|---|---|---|
| 002.151.5 | BDL | BDL | BDL |
| 002.151.8 | 5.26 | 5.11 | 5.26 |

Particle size of the material remaining from the Efficacy Study and material returned to Arbor was assessed. The assessment of returned material was carried out side by side with material retained. Stability data are presented in Table 25f and reflect monitoring of particle size over 42 days. The particle size of drug-free emulsions returned from the study site was identical to that of retained material. The particle size of the ART-207 containing emulsions returned from the study site was 10 nm bigger relative to that of retained material.

TABLE 25f

| | Particle size, nm | | |
|---|---|---|---|
| Material | Day of Shipment to study site, (Mar. 18, 2013) | Returned from the study site, (Apr. 25, 2013) | Retained at Arbor Therapeutics, (Apr. 25, 2013) |
| 002.151.5 | 37.4 | 45.7 | 46.6 |
| 002.151.8 | 61.9 | 77.6 | 66.5 |

We extended monitoring of particle size for the emulsions used in the efficacy study, both that shipped from the study site and material retained at Arbor for 55 days. FIG. 54 shows that particle size of the vehicle control did not significantly change over the period, whereas ART-207 containing emulsions were stable for 42 days. Particle size increase was observed for ART-207 containing emulsions starting from day 42. Possible bacterial contamination of ART-207 emulsions. (Previously monitored emulsions showed a similar rapid rise in particle size when they became contaminated due to handling.)

Regardless of the observed change in particle size of ART-207 containing emulsions starting from day 42, both emulsions shipped to/from the study site and retained samples were stable during animal treatment period. The treatment of animals with ART-207 containing emulsion was completed 22 days past the manufacturing date. In study ATL-3 formulated ART-207 clearly demonstrated similar or higher tumor suppression effect, caused significantly less weight loss, and provided a two fold increase in animal survival rate compared to Paclitaxel treated animals (see also formal report "EVALUATION OF THE ANTITUMOR EFFICACY OF FORMAULTED ART-207 WHEN ADMINISTERED INTRAVENOUSLY TO ATHYMIC NUDE MICE IMPLANTED SUBCUTANEOUSLY WITH HUMAN MDA-MB-231 MAMMARY TUMOR XENOGRAFTS. Southern Research Institute, Birmingham, Ala. 35255-5305)

Experiment ATL-3 was performed to evaluate the antitumor activity of the intravenous (IV) treatment with formulated ART-207 when administered on two different schedules to female, athymic NCr-nu/nu mice implanted subcutaneously (SC) with human MDA-MB-231 mammary tumor xenografts. Paclitaxel was included as a reference compound.

Tumor Model:

One-hundred and fifty-eight mice were implanted with fragments of the human MDA-MB-231 mammary tumor from an in vivo passage. Individual tumors of 90 animals grew to 88-216 mg in weight (88-216 mm3 in size) on Day 10 after tumor fragments implantation, the day of treatment initiation. The selected 90 animals with tumors were assigned to nine treatment groups so that the mean tumor weights in all groups on Day 10 were as close to each other as possible (mean tumor weights ranged from 147 to 154 mg, median tumor weights ranged from 144 to 153 mg). Different formulated ART-207 doses were achieved by administering different injection volumes of the 5.26 mg/mL formulation. The formulated ART-207 doses of 105.2, 78.9, and 52.6 mg/kg were 4.9x, 3.7x, 2.5x molar equivalent of a paclitaxel dose of 15 mg/kg, respectively, based on the molecular weight of formulated ART-207 of 1219.6 and molecular weight of paclitaxel of 853.9. The time points are indicated starting from the first day of treatment with formulated ART-207, vehicle control and Paclitaxel.

Study Design:

The study consisted of nine groups of ten mice per group for a total of 90 mice bearing human MDA-MB-231 mammary tumor on the first day of treatment, Day 0 Mice in Group 1 were untreated until formulated ART-207 treatment was added starting on Day 11: formulated ART-207 at a dose of 78.9 mg/kg/injection was administered intravenously (IV) once a day for five consecutive days (Q1Dx5) on Days 11-15. Animals in Groups 2, 3, and 4 were treated with formulated ART-207 which was administered IV on a Q1Dx5 schedule starting on Day 0 (Days 0-4) at doses of 105.2, 78.9, and 52.6 mg/kg/injection, respectively. Animals in Group 5 (Emulsion control) were treated IV on Q1Dx5 schedule starting on Day 0 with a drug free formulation. Animals in Group 6 were treated IV on Q1Dx5 schedule starting on Day 0 with paclitaxel at a dose of 15 mg/kg/injection. Animals in Group 7 were treated with formulated ART-207 which was administered IV once every four days for a total of three injections (Q4Dx3) starting on Day 0 (Days 0, 4, and 8) at a dose of 78.9 mg/kg/injection. Animals in Group 8 (Emulsion control) were treated IV on a Q4Dx3 schedule starting on Day 0 with a drug free formulation. Animals in Group 9 were treated IV on a Q4Dx3 schedule starting on Day 0 with paclitaxel at a dose of 18.9 mg/kg/injection.

Q1Dx5 schedule The IV treatment with formulated ART-207 at a dose of 105.2 mg/kg/injection on a Q1Dx5 schedule (Group 2) was lethal, resulting in death of eight out of ten animals (with deaths occurring on Days 5 and 6) and one more animal being euthanized on Day 5 due to being moribund. The treatment was associated with a maximum mean body weight loss of 8% (1.9 g), observed on Day 4. The one surviving mouse in the group was tumor-free on Day 56 (FIG. 55-57).

The IV treatment with formulated ART-207 at a dose of 78.9 mg/kg/injection on a Q1Dx5 schedule (Group 3) was toxic, resulting in death of six out of ten animals (with deaths occurring on Days 5 and 6) and a maximum mean body weight loss of 7% (1.5 g), observed on Day 4. Growth of the tumors of four surviving mice was inhibited by the formulated ART-207 treatment, with two animals being tumor-free on Day 56 and two other tumors weighing 32-40 mg on Day 56 (FIG. 55-57).

The IV administration with formulated ART-207 at a dose of 52.6 mg/kg/injection on a Q1Dx5 schedule (Group 4) was tolerated without deaths and was associated with a maximum mean body weight loss of 2% (0.4 g), observed on Day 4. The treatment with formulated ART-207 at a dose of 52.6 mg/kg/injection was very effective in the inhibition of the growth of the MDA-MB-231 mammary tumor xenografts. The treatment produced nine complete tumor regressions, with six animals remaining tumor-free on Day 56. Growth of the tumors in the group treated with formulated ART-207 at a dose of 52.6 mg/kg/injection was statistically different from the growth of the tumors in the control group, when individual animals' times to reach three tumor mass doublings were compared (Group 1 vs. Group 4: $P<0.001$) (FIG. 55-57).

The IV treatment with Emulsion Control on a Q1Dx5 schedule (Group 5) was tolerated without deaths or mean body weight loss. The median tumor reached three tumor mass doublings in 9.2 days, and reached 1,680 mg in weight on Day 11. Growth of the tumors in untreated control group and the group treated with Emulsion Control on a Q1Dx5 schedule was not statistically different, when individual animals' times to reach three tumor mass doublings were compared (Group 1 vs. Group 5: $P=0.810$) (FIG. 55-57).

The IV treatment with paclitaxel at a dose of 15 mg/kg/injection on a Q1Dx5 schedule (Group 6) resulted in death of one out of ten animals (with death occurring on Day 2). One more animal was euthanized on Day 12 due to ataxia. Treatment resulted in a mean body weight loss of 10% (2.2 g), observed on Day 6. Treatment with paclitaxel at a dose of 15 mg/kg/injection was effective in the inhibition of the growth of the MDA-MB-231 mammary tumor xenografts. The treatment produced five complete tumor regressions, with four animals remaining tumor-free on Day 56. Growth of the tumors in the group treated with paclitaxel at a dose of 15 mg/kg/injection on a Q1Dx5 schedule was statistically different from the growth of the tumors in the control group, when individual animals' times to reach three tumor mass doublings were compared (Group 1 vs. Group 6: P<0.001) (FIG. 55-57). Re-growth of the tumors in the group treated with formulated ART-207 at a dose of 52.6 mg/kg/injection (group 4) was slower than in the group treated with paclitaxel (group 6) at a dose of 15 mg/kg/dose when both were administered IV on a Q1D×5 schedule (Group 4 median tumor growth delay of >45.9 days, 6 tumor-free mice on Day 56 vs. Group 6 median tumor growth delay of 31.8 days, 4 tumor-free mice on Day 56); the difference in tumor growth was not statistically different between the two groups, when individual animals' times to reach three tumor mass doublings were compared (Group 4 vs. Group 6: P=0.133) (FIG. 55).

FIG. 55 Mice were divided into 5 groups (10 mice in each group). All test articles were administered to mice for five consecutive days via intravenous (iv) injections starting from day 0. Groups #2-4 received 105.2 (solid green), 78.9 (solid red), and 52.6 (solid yellow) mg/kg of formulated ART-207. Group #5 received drug-free lipid formulation (black dotted line, open squares). Group #6 received 15 mg/kg of Paclitaxel (blue dotted line, open circles). Each point on the curves represents mean tumor weight of each drug and vehicle treated group at the corresponding day of assessment. The mean group cutoff is two animals per group.

FIG. 56 Mice were divided into 5 groups (10 mice in each group). All test articles were administered to mice for five consecutive days via intravenous (iv) injections starting from day 0. Groups #2-4 received 105.2 (solid green), 78.9 (solid red), and 52.6 (solid yellow) mg/kg of formulated ART-207. Group #5 received drug-free lipid formulation (black dotted line, open squares). Group #6 received 15 mg/kg of Paclitaxel (blue dotted line, open circles). Each point on the curves represents mean mouse weight of each drug and vehicle treated group at the day of assessment. Tumored mouse weight was corrected for the weight of tumor. The mean group cutoff is two animals per group.

FIG. 57 Mice were divided into 6 groups (10 mice in each group). All test articles were administered to mice for five consecutive days via intravenous (iv) injections starting from day 0. Groups #2-4 received 105.2 (solid green), 78.9 (solid red), and 52.6 (solid yellow) mg/kg of formulated ART-207. Group #5 received drug-free lipid formulation (black dotted line, open squares). Group #6 received 15 mg/kg of Paclitaxel (blue dotted line, open circles). Each point on the curves represents mean tumor weight of each drug and vehicle treated group at the corresponding day of assessment. The mean group cutoff is two animals per group.

To elucidate the effect of tumor size on the toxicity of a high (78.9 mg/kg) ART-207 dose, and to test the ability of formulated ART-207 to suppress the growth of advanced tumors, an experiment on mice with the mean tumor size ~1460 mg was carried out. The human MDA-MB-231 mammary tumor xenografts in the untreated control group (Group 1) grew progressively in all ten mice until Day 11. The animals gained weight until Day 11. The median tumor reached three tumor mass doublings in 10.1 days and reached 1,461 mg (mean group tumor weight) in weight on Day 11 (see formal report). Three animals were euthanized on Day 11 due to tumor ulceration. The remaining seven mice were treated IV with formulated ART-207 at a dose of 78.9 mg/kg/injection on a Q1D×5 schedule starting on Day 11. Two out of seven animals died (with deaths occurring on Day 18) and animals experienced a maximum mean body weight loss of 15% (3.5 g), observed on Day 18 (FIG. 58). The lethality associated with the administration of formulated ART-207 in this group was less (2 out of 7 mice died, 29%) than the lethality associated with the administration of formulated ART-207 in Group 5 at the same dose, (6 out of 10 mice died, 60%) (Table 25g).

TABLE 25g

Dependence of formulated ART-207 toxicity on tumor size.

| Tumor size, mg | Dose, mpk | Toxicity Driven Death rate, % |
|---|---|---|
| 150 | 78.9 | 60 |
| 1461 | 78.9 | 33 |

FIG. 58. Mice were divided into 2 groups (10 mice in each group). All test articles were administered to mice for five consecutive days via intravenous (iv) injections starting from day 0. Group #1 received no injections (black solid line, open squares) from day 0 to day 11 and then a new sequence of Q1D×5 with 78.9 mg/kg was begun. Group #5 received drug-free lipid formulation (black dotted line, open squares). Each point on the curves represents mean mouse weight of each drug and vehicle treated group at the day of assessment. Tumored mouse weight was corrected for the weight of tumor. The mean group cutoff is two animals per group. The formulated ART-207 treatment resulted in an effective inhibition of the tumor growth: the median tumor weight decreased from 1,029 mg on Day 11 (based on seven mice) to 104 mg on Day 60 (FIG. 59).

FIG. 59. Mice were divided into 2 groups (10 mice in each group). All test articles were administered to mice for five consecutive days via intravenous (iv) injections starting from day 0. Group #1 received no injections (black solid line, open squares) from day 0 to day 11 and then a new sequence of Q1D×5 with 78.9 mg/kg was begun. Group #5 received drug-free lipid formulation (black dotted line, open squares). Each point on the curves represents mean tumor weight of each drug and vehicle treated group at the corresponding day of assessment. The mean group cutoff is two animals per group.

The data obtained demonstrate effective suppression of advanced tumors by formulated ART-207 while its toxic effect was notably decreased. The decreased lethality associated with the administration of high doses of ART-207 into animals with advanced tumors supports the selective cellular uptake of formulated ART-207 by tumor tissue and provides the opportunity to safely adjust the dose in patients with various tumor sizes. The continuous regression of the tumors following a single course of dosing suggests that pseudoLDL nanoparticle formulated ART-207 shows an extended efficacy. The slower regrowth of tumors treated with formulated ART-207 in both the initial ATL 3 study with a single Q1D×5 course (FIG. 55) and in the second study where animals with much larger tumors were dosed (FIG. 59. This can be explained by tumor up take and sequestration of prodrug/drug into tumor cells not actively dividing but still growing. When those cells reach entry into cell division the sequestered drug exerts its toxic effect. (Paclitaxel is only effective in cells undergoing division.)

Q4D×3 schedule The IV administration of formulated ART-207 at a dose of 78.9 mg/kg/injection on a Q4D×3 schedule (Group 7) was tolerated without deaths and resulted in a mean body weight loss of 2% (0.4 g), observed on Day 8. Treatment with formulated ART-207 at a dose of 78.9 mg/kg/injection was very effective in the inhibition of the growth of the MDA-MB-231 mammary tumor xenografts. The treatment produced three complete tumor regressions, with all three animals remaining tumor-free on Day 56. Growth of the tumors in the group treated with formulated ART-207 at a dose of 78.9 mg/kg/injection was statistically different from the growth of the tumors in the untreated control group (Group 1 vs. Group 7: P<0.001) and from the Emulsion Control group (Group 7 vs. Group 8: P<0.001), when individual animals' times to reach three tumor mass doublings were compared (FIGS. 60a and 60b).

The IV treatment with Emulsion Control on a Q4D×3 schedule (Group 8) was tolerated without deaths or mean body weight loss. The median tumor reached three tumor mass doublings in 10.7 days, and reached 1,163 mg in weight on Day 11. Growth of the tumors in untreated control group and the group treated with Emulsion Control administered on a Q4D×3 schedule was not statistically different (Group 1 vs. Group 8: P=0.252) nor was the growth of the tumors in the two Emulsion Control groups (when administered on Q1D×5 and Q4D×3 schedules, Group 5 vs. Group 8: P=0.348), when individual animals' times to reach three tumor mass doublings were compared (FIGS. 60a and 60b).

The IV treatment with paclitaxel at a dose of 18.9 mg/kg/injection on a Q4D×3 schedule (Group 9) was tolerated without deaths or mean body weight loss (FIG. 60b). The treatment with paclitaxel at a dose of 18.9 mg/kg/injection was very effective in the inhibition of the growth of the MDA-MB-231 mammary tumor xenografts (FIG. 60a). The treatment produced one complete tumor regression. Growth of the tumors in the group treated with paclitaxel at a dose of 18.9 mg/kg/injection on a Q4D×3 schedule was statistically different from the growth of the tumors in the untreated control group (Group 1 vs. Group 9: P<0.001) and from the Emulsion Control group (Group 8 vs. Group 9: P<0.001), when individual animals' times to reach three tumor mass doublings were compared.

FIG. 60a. Mice were divided into 3 groups (10 mice in each group). All test articles were administered to mice on day 0, 5, and 9 via intravenous (iv) injections. Group #7 received 78.9 mg/kg of formulated ART-207 (solid red line, filled squares). Group #8 received drug-free lipid formulation (black dotted line, open squares). Group #9 received 18.9 mg/kg of Paclitaxel (blue dotted line, open circles). Each point on the curves represents mean tumor weight of each drug and vehicle treated group at the corresponding day of assessment. The mean group cutoff is two animals per group.

FIG. 60b. Mice were divided into 3 groups (10 mice in each group). All test articles were administered to mice on day 1, 5, and 9 via intravenous (iv) injections. Group #7 received 78.9 mg/kg of formulated ART-207 (solid red line, filled squares). Group #8 received drug-free lipid formulation (black dotted line, open squares). Group #9 received 18.9 mg/kg of Paclitaxel (blue dotted line, open circles). Each point on the curves represents mean mouse weight of each drug and vehicle treated group at the day of assessment. Tumored mouse weight was corrected for the weight of tumor. The mean group cutoff is two animals per group. Both the MTD (ATL-1,2)) and Efficacy (ATL-3) studies clearly demonstrated similar or higher tumor suppression effect of formulated ART-207 compared to Paclitaxel at concentrations below the MTD. In contrast to Paclitaxel the tumor suppression effect of formulated ART-207 was not accompanied by any significant weight loss. Relative to Paclitaxel, the treatment with formulated ART-207 consistently resulted in a significant increase in animal survival rate and higher number of tumor free animals (Table 25h).

TABLE 25h

Comparative Effect of Formulated ART-207 and Paclitaxel on End of Study Animal Survival and Number of Tumor-Free Animals.

| Study # | Compound | Tumor size, mg | Treatment Schedule | Dose, mpk | Particle size, nm | Survival rate, % | Tumor free mice, % |
|---|---|---|---|---|---|---|---|
| 1 | Formulated ART-207 | 270 | Q1D×5 | 72.6 | 120 | 100 | 40 |
|   | Paclitaxel | 270 | Q1D×5 | 15 | N/A | 20 | 0 |
| 2 | Formulated ART-207 | 150 | Q1D×5 | 52.6 | 65 | 80 | 60 |
|   | Paclitaxel | 150 | Q1D×5 | 15 | N/A | 40 | 40 |

Experiment 26. Preparation of ART-207 (Lot# AW-004-24) containing emulsion.

Purpose: To systematically investigate effect of TG/ART-207 ratio-on particle size, stability and ART-207 incorporation capacity of formulation.

TABLE 26a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 21 Mar. 2013 | 002.155.1 | TSPM | 4300 | 490 | 69 | 148 | 11 | 10 | 505 | 300 | 1107 | 0 |

TABLE 26b

Ratios for major formulation components.

| TG/ART-207 | PC/ART-207 | PC/TG | FC/CE |
|---|---|---|---|
| 0.97 | 10.72 | 11.03 | 0.47 |

Coarse suspension was prepared and MF processed (lot#002.156.1).

TABLE 26c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 22 Mar. 2013 | 002.156.1 | 63 | 4.05 | 80.3 | 42 | 59 |

MFP. FIG. 61 shows that particle size reaches R1 at 69 nm after 30 mm of processing at ~60° C. MFP was stopped and material was sterile filtered. Decrease of the particle size from 69 to 62 nm was observed after filtration.

HPLC Analysis. ART-207 content in resultant emulsion determined by HPLC (Taxane_Test.M, Rev 2) was 4.05 mg/ml. Data shoes 83% of the drug used for preparation of this formulation was incorporated into lipid particles (Table 26c). Particle size analysis of ART-207 containing formulation. The resultant ART-207 containing emulsion was highly stable. In FIG. 62 and Table 26c, particle did not increase over 42 days.

MF processing of formulation with TG/ART-207 ratio equal to 0.97 resulted in highly stable ~60 nm particles. ART-207 incorporation capacity of this formulation was 83%. The lower drug incorporation capacity was expected based on the TG/ART-207 ratio of 1.

Preparation of Art-207 Containing Formulation for PK/PD Studies

Experiment 27. Preparation of ART-207 (Lot# AW-004-24) containing emulsion. To prepare of ART-207 containing formulation for PK/PD studies and to systematically investigate effect of TG/ART-207 ratio on particle size, stability, and ART-207 incorporation capacity of formulation.

MFP. FIG. 63 shows that particle size reaches R1 at 75 nm after 50 mm of processing at ~60° C. Temperature was lowered to 20° C. and material was processed for an additional 20 min. MF processing at 20° C. resulted in slight increase of the particle size to 78 nm and reached R2. MFP was stopped and material was sterile filtered. Decrease of the particle size from 78 to 62 nm was observed after filtration.

HPLC Analysis. ART-207 content in resultant emulsion determined by HPLC (Taxane_Test.M, Rev 2) was 4.8 mg/ml. The data indicate that 94% of the drug used for preparation of this formulation was incorporated into lipid particles (Table 27c). Particle size analysis of ART-207 containing formulation. ART-207 containing emulsion was highly stable. In FIG. 64 and Table 27c that particle size did not change over 43 days.

TMF processing of formulation with TG/ART-207 ratio equal to 1.17 resulted in highly stable ~60 nm particles. ART-207 incorporation capacity of this formulation was 94%. Higher drug incorporation capacity (relative to formulation described in experiment 26) was expected based on the higher TG/ART-207 ratio. A sample of ≥30 ml of the lot #002.156.3 was shipped to the study site; ~10 ml sample of the lot #002.156.3 was retained.

TABLE 27a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 25 Mar. 2013 | 002.156.2 | TSPM | 4340 | 600 | 70 | 150 | 10 | 10 | 511 | 300 | 1126 | 0 |

TABLE 27b

Ratios for major formulation components.

| TG/ART-207 | PC/ART-207 | PC/TG | FC/CE |
|---|---|---|---|
| 1.17 | 10.70 | 9.11 | 0.47 |

Coarse suspension was prepared and MF processed (lot#002.156.3).

TABLE 27c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 25 Mar. 2013 | 002.156.3 | 62 | 4.80 | 94.0 | 39 | 61 |

The material was characterized on the day of shipment. Data noted in Table 27d.

TABLE 27d

Formulated ART-207. Content and particle size.

| Lot# | Material | ART-207, mg/ml | Particle size, nm |
|---|---|---|---|
| 002.156.3 | Formulated ART-207 | 4.49 | 61.9 |

Table 27d shows that ART-207 content as determined by HPLC was slightly lower compared to that on the day of manufacture, whereas particle size did not change. The treatment of animals was performed via single intravenous injection.

TABLE 27e

ART-207 content and doses.

| Lot# | Material | ART-207 mg/ml | Dose, mg/kg | Injection Volume, ml (per 20 g of mouse weight) |
|---|---|---|---|---|
| 002.156.3 | Formulated ART-207 | 4.49 | 70 | 0.31 |

Material unused for dosing of animals was shipped back to Arbor Therapeutics after the end of the treatment. ART-207 content was assessed. The assessment of material shipped back was carried out side by side with material retained. Table 27f shows that material returned from the PK/PD study site evaluated by Taxane_Test.M Rev. 2 method and material retained have similar drug content. ART-207 content was not significantly lower compared to that on the day of shipment. Decrease of ART-207 content relative to that on the day of manufacture was observed (Tables 27c and 27f).

TABLE 27f

HPLC Analyses of ART-207 Content, mg/mL

| Material | Taxane_Test.M Rev 2 On the day of shipment | Taxane_Test.M Rev 2 Returned Material | Taxane_Test.M Rev 2 Retained Material |
|---|---|---|---|
| 002.156.3 | 4.49 | 4.34 | 4.30 |

Particle size of the material remaining from the PK/PD Study and that returned to Arbor was assessed on the day of its delivery. Assessment of returned material was carried out side by side with material retained. Data are presented in Table 27g and reflect monitoring of particle size from day 0 to the end of PK/PD treatment phase. The particle size of emulsions received back from the study site was slightly (not significantly) higher relative to that of retained material. Particle size of the formulated ART-207 did not change from its day of manufacture until the dosing date of the PK/PD study (Tables 27c and 27g). There was no significant difference of the particle size of returned and retained material as well.

TABLE 27g

Particle size, nm

| Material | Day of Shipment to study site, (14 May 2013) | Returned from study site, (31 May 2013) | Retained at Arbor Therapeutics, (31 May 2013) |
|---|---|---|---|
| 002.156.3 | 61.9 | 67.1 | 65.8 |

The formulated ART-207 demonstrated selectivity in the PK/PD Study (ATL-4 and 5). Data suggest selective cellular uptake of formulated ART-207 by the organs actively expressing LDL-receptors (see also formal report "DETERMINATION OF PLASMA AND TISSUE CONCENTRATIONS OF ART-207 AND PACLITAXEL IN NONTUMORED AND TUMORED MICE AFTER A SINGLE INTRAVENOUS INJECTION WITH FORMULATED ART-207 OR PACLITAXEL. Southern Research Institute, Birmingham, Ala. 35255-5305)

Experiments ATL-4 and ATL-5. To determine the concentration of paclitaxel and ART-207 derived paclitaxel in plasma, brain, heart, liver, lungs and tumor (experiment ATL-5 only) after a single intravenous (IV) injection of formulated paclitaxel or ART-207 to nontumored female athymic NCr-nu/nu mice and female athymic NCr-nu/nu mice bearing a subcutaneous (SC) human MDA-MB-231 mammary tumor.

Tumor Model; Experiment ATL-4. Animals were nontumored.

Experiment ATL-5: Mice were implanted with fragments of the human MDA-MB-231 mammary tumor from an in vivo passage. The day of tumor fragments implantation was designated as Day 0. Individual tumors of 30 animals grew to 908-1,437 mg in weight (908-1,437 mm3 in size) on Day 23 after tumor fragments implantation, one day before the treatment day. Thirty selected animals were assigned to ten treatment groups so that the mean tumor weights in all groups on Day 23 were as close to each other as possible (mean tumor weights ranged from 1,056 to 1,178 mg, median tumor weights ranged from 908 to 1,152 mg). Treatment in both experiments ATL-4 and ATL-5 was administered on the same day.

Experiment ATL-4: The study consisted of ten groups of three nontumored mice per group for a total of 30 mice on Day 1, one day before the treatment. All treatments were administered as a single IV injection on Day 2. Animals in Groups 1-5 were treated with formulated ART-207 at a dose of 70 mg/kg. Animals in Groups 6-10 were treated with paclitaxel at a dose of 18.9 mg/kg. The formulated ART-207 dose of 70 mg/kg was 2.6x molar equivalent of a paclitaxel dose of 18.9 mg/kg, based on the molecular weight of formulated ART-207 of 1219.6 and molecular weight of paclitaxel of 853.9.

Experiment ATL-5

The study consisted of ten groups of three mice per group for a total of 30 mice bearing human MDA-MB-231 mammary tumor on Day 23 after tumor fragment implantation, one day before the treatment. All treatments were administered as a single IV injection on Day 24. Animals in Groups 1-5 were treated with formulated ART-207 at a dose of 70 mg/kg. Animals in Groups 6-10 were treated with paclitaxel at a dose of 18.9 mg/kg. The formulated ART-207 dose of 70 mg/kg was 2.6x molar equivalent of a paclitaxel dose of 18.9 mg/kg.

Plasma levels of Paclitaxel, ART-207, and ART-207 derived Paclitaxel. For mice administered a single IV dose of formulated ART-207, a mean peak plasma concentration ($C_{max}$) of ART-207 of 640 µg/mL was observed at 5 minutes (0.083 hours) after dosing (earliest time point); the mean concentration of paclitaxel in plasma at this time was 2.24 8 µg/mL (2237 ng/mL). ART-207 subsequently was eliminated from plasma with an apparent terminal elimination half-life of 2.8 hrs; the apparent terminal elimination half-life of paclitaxel in plasma for animals administered formulated ART-207 was slower and was 11.5 hr. The low rate of clearance of ART-207 (22.0 mL/hr/kg) and small volume of distribution at steady state of ART-207 (88.0 mL/kg) were indicative of limited metabolism/elimination/tissue distribution of the compound. The AUClast for ART-207 in plasma was 2794 hr·µg/mL and that for paclitaxel was 14.4 hr·µg/mL, indicating that the systemic exposure to ART-207 was approximately 200-fold greater than that to paclitaxel (FIG. 65). For mice administered a single IV dose of paclitaxel, a mean peak plasma concentration of paclitaxel of 32.9 µg/mL was observed at 5 minutes (0.083 hours) after dosing (earliest time point); thereafter, paclitaxel was eliminated from plasma with an apparent terminal elimination half-life of 1.0 hour. AUClast for paclitaxel in plasma was 37.7 hr·µ/mL. The total body clearance of paclitaxel (500 mL/hr/kg) and volume of distribution of paclitaxel at steady state (658 mL/kg) were higher than the corresponding values determined for ART-207. Although the relative tissue distribution of paclitaxel was similar to that observed for mice given formulated ART-207, mean peak tissue concentrations of paclitaxel were higher for mice administered paclitaxel than for mice administered a 2.6-fold higher molar equivalent dose of formulated ART-207.

Change in Mean Concentration of ART-207 and Paclitaxel in Plasma Over Time

FIG. 65 Tumored and/or non-tumored mice were subdivided into 5 groups (3 mice per each group). All mice were injected intravenously with 70 mg/kg of formulated ART-207. Blood samples were collected at 5, 30, 60, 240 and 480 min after single bolus injection. Each time point represents 3 mice. Plasma concentration is expressed as area under the concentration curve (AUC) for each time point analyzed. Based on AUClast values (areas under the mean concentration versus time curve from 0 to the last quantifiable sample), the systemic exposure to Paclitaxel in mice injected with Paclitaxel was similar for non-tumored and tumored mice. The difference between Paclitaxel levels of Non-tumored and Tumored mice injected with Paclitaxel was not significant (FIG. 66). Data indicated that absence or presence of tumor did not affect plasma Paclitaxel content, and therefore inability of Paclitaxel to selectively target tumor tissue.

FIG. 66. Non-tumored mice were subdivided into 5 groups (3 mice per each group). All mice were injected intravenously with 18.9 mg/kg of Paclitaxel. Blood samples were collected at 5, 30, 60, 240, and 480 mm after single bolus injection. Each time point represents 3 mice. Tissue concentration is expressed as area under the concentration curve (AUC) from 0 to last time point analyte was quantifiable (8 hrs). Areas under the mean concentration versus time curve from 0 to the time of the last quantifiable sample (AUClast) were calculated using the linear/log trapezoidal rule. Plasma levels of ART-207 derived Paclitaxel in ART-207 treated tumored animals are significantly lower compared to that in ART-207 treated non-tumored mice (FIG. 67). Data demonstrate significant impact of tumor on plasma levels of ART-207 derived paclitaxel suggesting improved targeting capability of the formulated ART-207 relative to Paclitaxel.

FIG. 67. Tumored mice were subdivided into 5 groups (3 mice per each group). All mice were injected intravenously with 70 mg/kg of formulated ART-207. Blood samples collected at 5, 30, 60, 240, and 480 mm after single bolus injection. Each time point represents 3 mice. Tissue concentration is expressed as area under the concentration curve (AUC) from 0 to last time point analyte was quantifiable (8 hrs). Areas under the mean concentration versus time curve from 0 to the time of the last quantifiable sample (AUC last) calculated using the linear/log trapezoidal rule. Difference between Paclitaxel plasma levels of non-tumored and tumored mice injected with formulated ART-207 was significant. When the Volume of Distribution of formulated ART-207 and Paclitaxel were evaluated post iv dosing, the Volume of Distribution of formulated ART-207 was significantly lower (6 fold) than that of Paclitaxel indicating formulated ART-207 remains within the vascular system and is not distributed into tissues. The long circulating pseudo LDL nanoparticulate formulation can continue to concentrate into tumor tissues. This is consistent with the observed extended efficacy of formulated ART-207 in both ATL 2 and ATL 3 studies. Also, tumor tissue cellular up take of the formulation into growing but not dividing tumor cells would provide a reservoir of prodrug/drug to exert a cytotoxic effect once those cells begin cell division. The cytotoxic effect of taxanes is only present for dividing cells. A reservoir of drug in growing but not dividing cells is desirable since not all tumor cells are dividing at any given time so that when these quiescent cells do begin to divide leading to tumor recurrence, they are killed by the reservoir of drug presence.

Organ distribution of Paclitaxel in mice injected with Paclitaxel and ART-207. Organs were harvested and then analyzed without prior perfusion or rinsing in PBS or saline. With the small volume of distribution observed and reported for formulated ART-207, we will focus our data analysis on distribution of ART-207 derived Paclitaxel which is a more specific indicator of formulated ART-207 tissue distribution and processing that result in local release of the Paclitaxel moiety. Non-tumored mice Tissue levels of Paclitaxel were significantly lower in mice injected with ART-207 relative to that in mice injected with Paclitaxel (FIG. 68).

FIG. 68. Non-tumored mice were subdivided into 5 groups (3 mice per each group). All mice were injected intravenously with 70 mg/kg of formulated ART-207 or 18.9 mg/kg of Paclitaxel. Blood samples and organs were collected at 5, 30, 60, 240, and 480 min after single bolus injection. Each time point represents 3 mice. Tissue concentration is expressed as area under the concentration curve (AUC) from 0 to last time point analyte was quantifiable (8 hrs). Areas under the mean concentration versus time curve from 0 to the time of the last quantifiable sample (AUClast) were calculated using the linear/log trapezoidal rule. Difference between Paclitaxel levels of non-tumored mice injected with Paclitaxel or formulated ART-207 was significant for all assessed tissues ($p<0.05$). Tumored mice Paclitaxel levels were lower in all non-target organs of mice injected with ART-207 relative to that in mice injected with Paclitaxel, whereas Paclitaxel concentration in tumor tissue was significantly higher in mice injected with formulated ART-207 (FIGS. 69, 70). Results are in agreement with Paclitaxel plasma concentration data and suggest selective targeting of tumor site by formulated ART-207.

FIG. 69. Tumored mice were subdivided into 5 groups (3 mice per each group). All mice were injected intravenously with 70 mg/kg of formulated ART-207 or 18.9 mg/kg of Paclitaxel. Blood samples and organs were collected at 5, 30, 60, 240 and 480 min after single bolus injection. Each time point represents 3 mice. Tissue concentration is expressed as area under the concentration curve (AUC) from 0 to last time point analyte was quantifiable (8 hrs). Areas under the mean concentration versus time curve from 0 to the time of the last quantifiable sample (AUClast) were calculated using the linear/log trapezoidal rule. Difference between Paclitaxel levels of non-tumored mice injected with Paclitaxel or formulated ART-207 was significant for all assessed tissues ($p<0.05$).

FIG. 70. Tumored mice were subdivided into 5 groups (3 mice per each group). All mice were injected intravenously with 70 mg/kg of formulated ART-207 or 18.9 mg/kg of Paclitaxel. Tumors were collected at 5, 30, 60, 240 and 480 min after single bolus injection. Each time point represents 3 mice. Tissue concentration is expressed as area under the concentration curve (AUC) from 0 to last time point analyte was quantifiable (8 hrs). Areas under the mean concentration versus time curve from 0 to the time of the last quantifiable sample (AUClast) were calculated using the linear/log trapezoidal rule. In both non-tumored and tumored mice treated with formulated ART-207 the highest and comparable concentrations of Paclitaxel were observed in the liver, lung and tumor tissues (FIGS. 68, 69), which are the major LDL-receptor expressing sites. Data obtained suggest selective cellular uptake of formulated ART-207 by the organs actively expressing LDL-receptors and support LDL-receptor dependent mechanism for cellular internalization of formulated ART-207. The PK/PD data are in agreement with the results from the efficacy and toxicity studies which show similar or higher potency of formulated ART-207 compared to Paclitaxel while lower toxicity is observed for formulated ART-207.

Experiment 28. Preparation of ART-207 (Lot# AW-004-24) containing emulsion. To systematically investigate effect of TG/ART-207 ratio (Table 28b) on particle size, stability and ART-207 incorporation capacity of the formulation.

TABLE 28a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 26 Mar. 2013 | 002.158.1 | TSPM | 4345 | 698 | 70 | 150 | 11 | 10 | 529 | 301 | 1130 | 0 |

TABLE 28b

Ratios for major formulation components.

| TG/ART-207 | PC/ART-207 | PC/TG | FC/CE |
|---|---|---|---|
| 1.32 | 10.35 | 7.84 | 0.47 |

Coarse suspension was prepared and MF processed (lot#002.158.2).

TABLE 28c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 27 Mar. 2013 | 002.158.2 | 80 | 4.74 | 89.6 | 37 | 72 |

MFP. In FIG. 71, particle size reaches 102 nm after 10 mm of processing at ~60° C. MFP was stopped and material was sterile filtered. Decrease of the particle size from 102 to 81 nm was observed after filtration.

HPLC Analysis. ART-207 content in resultant emulsion determined by HPLC (Taxane_Test.M, Rev 2) was 4.74 mg/ml. Data indicate that 89.6% of the drug used for preparation of this formulation was incorporated into lipid particles (Table 28c). Particle size analysis of ART-207 containing formulation. The ART-207 containing emulsion was stable. In FIG. 72 and Table 28c, particle size did not increase over 37 days.

MF processing of formulation with TG/ART-207 ratio equal to 1.32 resulted in highly stable ~70 nm particles. ART-207 incorporation capacity of this formulation was 89.6%. Drug incorporation capacity did not increase compared to the formulation with TG/ART-207 ratio equal to 1.17 (experiment 27).

Experiment 29. Preparation of ART-207 containing emulsion. To systematically investigate effect of TG/ART-207 ratio (Table 33b) on particle size, stability and ART-207 incorporation capacity of the formulation.

TABLE 29a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 28 Mar. 2013 | 005.1.1 | TSPM | 4340 | 850 | 70 | 150 | 11 | 10 | 530 | 300 | 1130 | 0 |

TABLE 29b

Ratios for major formulation components.

| TG/ART-207 | PC/ART-207 | PC/TG | FC/CE |
|---|---|---|---|
| 1.60 | 10.32 | 6.44 | 0.47 |

Coarse suspension was prepared and MF processed (lot#005.1.2).

TABLE 29c

Particle size, ART-207 content, and particle stability of resultant emulsion.

| Manufacturing Date | Lot# | Particle size by intensity, nm | ART-207 Content, mg/ml | Recovery, % | Formulation Stability Days past mfg | Particle size nm |
|---|---|---|---|---|---|---|
| 29 Mar. 2013 | 005.1.2 | 74 | 4.74 | 89.5 | 35 | 78 |

MFP In FIG. 73, particle size reaches 77 nm after 10 min of processing at ~60° C. MFP was stopped and filtered. No change of the particle size was observed after filtration.

HPLC Analysis. ART-207 content in resultant emulsion determined by HPLC (Taxane_Test.M, Rev 2) was 4.74 mg/ml. The data indicate that 89.5% of the drug used for preparation of this formulation was incorporated into lipid particles (Table 29c). Particle size analysis of ART-207 containing formulation. The resultant ART-207 containing emulsion was fairly stable. In FIG. 74 and Table 29c, particle size increased by 4 nm over 35 days.

MF processing of formulation with TG/ART-207 ratio equal to 1.6 resulted in relatively stable ~75 nm particles. A slight increase of particle size observed for lot#005.1.2 over monitoring period suggests initial signs of instability accompanying higher TG/ART ratio. ART-207 incorporation capacity of this formulation was 89.5% and did not increase compared to formulation with TG/ART-207 ratio equal to 1.17 and 1.32 (experiment 27 and 28, respectively). Data suggest that the optimum for TG/ART-207 ratio is in the range of 1.2-1.3.

Experiment 30. Preparation of ART-207 (Lot# AW-004-24) containing emulsion. To generate ~90-100 nm ART-207 containing particles and to assess their drug-incorporation capacity and stability. Since resultant particle size in experiments 28 and 29 was significantly below targeted (~90-100 nm) the MF processing pressure was lowered to 10,000 PSI. The TG/ART ratio was 1.35.

TABLE 30a

Formulation composition.

| | | | Components Weighed, mg (per 100 ml) | | | | | | | | | |
|---|---|---|---|---|---|---|---|---|---|---|---|---|
| Date | Lot# | Material | PC | TG | FC | CE | U | Vit E | ART | P188 | DMPC | PS |
| 29 Mar. 2013 | 005.2.1 | TSPM | 4250 | 735 | 70 | 150 | 10 | 10 | 543 | 300 | 1123 | 0 |

TABLE 30b

Ratios for major formulation components.

| TG/ART-207 | PC/ART-207 | PC/TG | FC/CE |
|---|---|---|---|
| 1.35 | 9.90 | 7.31 | 0.47 |

Coarse suspension was prepared and MF processed (lot#005.2.2).

TABLE 30c

Particle size, ART-207 content, and particle stability of resultant emulsion.

| Manu-facturing Date | Lot# | Particle size by intensity, nm | ART-207 Content, mg/ml | ART-207 Recovery, % | Formulation Stability Days past mfg | Particle size nm |
|---|---|---|---|---|---|---|
| 29 Mar. 2013 | 005.2.2 | 102 | 4.85 | 89.3 | 35 | 101 |

MFP. In FIG. 75 that particle size reaches 105 nm after 10 mm of processing at ~60° C. MFP was stopped and material filtered. No significant change of the particle size was observed after filtration.

HPLC Analysis. ART-207 content in resultant emulsion determined by HPLC (Taxane_Test.M, Rev 2) was 4.85 mg/ml. This data indicate that 89.3% of the drug used for preparation of this formulation was incorporated into lipid particles (Table 30c). Particle size analysis of ART-207 containing formulation. The resultant ART-207 containing emulsion was highly stable. FIG. 76 and Table 30c show that particle size did not change over 35 days.

MF processing of formulation with TG/ART-207 ratio equal to 1.35 resulted in highly stable ~105 nm particles. ART-207 incorporation capacity of this formulation was 89.3% as expected for this TG/ART-207 ratio. Data obtained indicate that the current formulation has the capacity to generate stable particles in at least 40-100 nm range.

Composition and Ratios. Unique composition with specific ratios of formulation components that produces stable drug-free and drug-containing nanoparticles in the range from 40 to 100 nm. The optimal range of total solids calculated as Weight/Volume (W/V) percent is 6.5-7.5% (TS, %). The optimal range of total lipids calculated as Weight/Volume (W/V) percent is 5.5-6.5% (TL, %). Ratios for major components are given in the Tables 30d.

TABLE 30d

Ratios for major formulation components.

| TG/ART-207 | PC/ART-207 | PC/TG | FC/CE | PC/TC | TG/TC |
|---|---|---|---|---|---|
| 0.97-1.6 | 7.5-12 | 3.5-11 | 0.3-0.6 | 17-25 | 2-7 |

For exact composition and details see Appendix, Master Tables 2 and 3.

TG/ART-207 Ratio. The concentration of TG and specifically TG/ART-207 ratio is the major factor that determines stability of drug-containing emulsion. The optimum range of TG/ART-207 ratios is 0.97-1.4. FIG. 77 shows that increase of the TG/ART-207 ratio above 0.97 facilitates ART-207 incorporation while resulting in stable particles. ART-207 incorporation reaches the maximum and plateaus at TG/ART-207 ratio ~1.3-1.4. Further increase of TG/ART-207 ratio does not enhance drug incorporation capacity of the formulation and moreover, results in unstable nanoparticles.

FIG. 77. Effect of TG/ART-207 ratio on ART-207 incorporation capacity of formulation (black solid line, left axis) and particle size increase (black dotted line, right axis). ART-207 incorporation capacity (i.e. drug content of resultant emulsion) is expressed as percent of amount of drug weighed for preparation of this emulsion. Particle size increase is expressed as percent of particle size change over time relative to that on the day of manufacturing.

Processing Temperature. Although processing of material at lower temperatures (~20° C.) yields smaller particles, processing at 60° C. results in more stable emulsions. FIG. 78 shows that processing at ~20° C. results in ~55 nm drug-containing nanoparticles, whereas 60° C. processing yields ~65 nm drug-containing nanoparticles. ~15% particle size increase during the storage was observed only in the material processed at ~20° C. (FIG. 78). Both "smaller" and "bigger" nanoparticles contained similar amounts of ART-207.

FIG. 78. Dependence of particle size (black solid line, left axis) and percent of particle size increase during the storage (black dotted line, right axis) on processing temperature.

Development of lipid-based formulations for incorporation of 287. Optimization of 287 incorporation capacity, particle size and stability. For all examples described below, see also Master Tables 1, 2, and 3 (Appendix II).

Experiment 31. Preparation of 287 (Lot# ISI-30052013-1) containing lipid emulsion. Investigate the capacity of formulation developed for preparation of ART-207-containing nanoparticles to incorporate structurally different 287, a lipophilic drug, not a prodrug derivative.

TABLE 31a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 4 Jun. 2013 | 005.16.1 | TSPM | 5370 | 606 | 71 | 149 | 10 | 10 | 508 | 300 | 0 | 0 |

TABLE 31b

Ratios for major formulation components.

| TG/ART 287 | PC/ART 287 | PC/TG | FC/CE |
|---|---|---|---|
| 1.19 | 10.57 | 8.86 | 0.47 |

Coarse suspension was prepared and MF processed (lot#005.16.2). Buffer: 10 mM Tris-HCl pH 7.4.

TABLE 31c 287 content and stability of resultant emulsion.

| | | 287 | | Formulated 287 Stability | | |
|---|---|---|---|---|---|---|
| Manufacturing Date | Lot# | Content, mg/ml | Recovery 1, % | Days past mfg | Content, mg/ml | Recovery 2, % |
| 4 Jun. 2013 | 005.16.2 | 2.81 | 55.3 | 28 | 2.64 | 94.0 |

Recovery 1, %—relative to amount of 287 used for formulation; Recovery 2, %—relative to 287 content determined in emulsion on the day of manufacturing;

TABLE 31d

Particle size and stability of resultant emulsion.

| | | Particle size | Formulation Stability | |
|---|---|---|---|---|
| Manufacturing Date | Lot# | by intensity, nm | Days past mfg | Particle size nm |
| 4 Jun. 2013 | 005.16.2 | 56.4 | 28 | 67.4 |

MFP. In FIG. 79, particle size reached R1 at ~80.6 nm after 100 min of processing at 55-65° C. MFP was stopped and filtered. A decrease of particle size from 80.6 to 56.4 nm was observed after filtration (FIG. 79).

Figure 85:
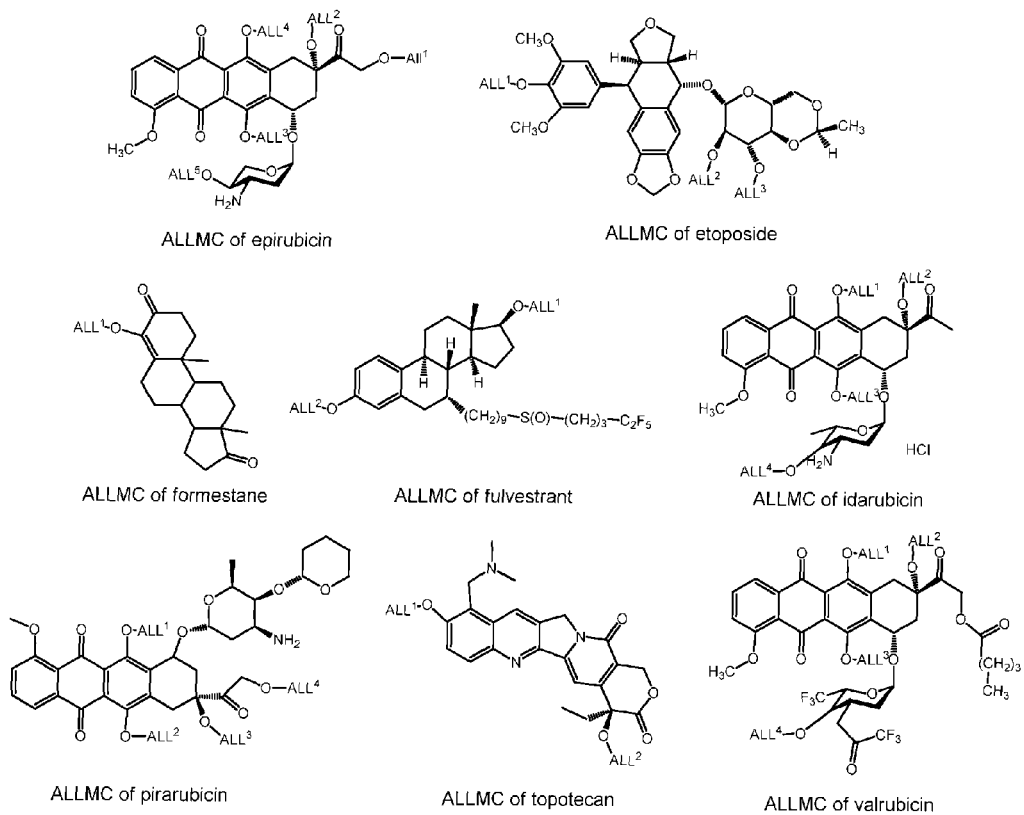
FIG. 85 describes some embodiments of the Acid Labile Lipophilic Molecular Conjugates.

HPLC Analysis. 287 content in resultant emulsion determined by HPLC (Taxane_Prodrug.M) was 2.81 mg/ml. Data indicate that only 55.3% of the drug used for preparation of this formulation was incorporated into lipid particles (Table 31c). HPLC determined drug content of the unfiltered emulsion was 4.40 mg/ml. Data indicate that 86.6% of the drug used for preparation of this formulation was incorporated into lipid particles and suggests that substantial portion (~36%) of formulated 287 was lost during final filtration step at the end of MF processing. The HPLC data are in line with notable decrease of the particle size after filtration. Data suggest particle size heterogeneity of resultant emulsion and retention of large 287 containing particles on the filter. No decrease of 287 content from 2.81 to 2.64 mg/ml (6%) was observed in resultant emulsion after 28 days of storage at room temperature (Table 31c). Particle size analysis of 287 containing formulation. FIG. 85 and Table 39d show that particle size increased from 53.2 to 72.6.4 nm over 6 days and then stabilized in the range of 67 nm No further change of particle size observed up to day 28 (FIG. 80).

Particle size analysis data are in line with HPLC data indicates: a) decrease of nanoparticle size and 287 content after final filtration step; and b) relative stability of resultant emulsion and formulated 287. Emulsion was prepared in 10 mM Tris-HCl buffer, pH 7.4.

Experiment 32. Preparation of 287 containing lipid emulsion. Investigate the capacity of DMPC-containing formulation developed for preparation of ART-207-containing stable nanoparticles to incorporate structurally different 287.

TABLE 32a

Formulation composition.

Components Weighed, mg (per 100 ml)

| Date | Lot# | Material | PC | TG | FC | CE | U | Vit E | ART | P188 | DMPC | PS |
|---|---|---|---|---|---|---|---|---|---|---|---|---|
| 5 Jun. 2013 | 005.17.1 | TSPM | 4360 | 602 | 71 | 150 | 10 | 10 | 507 | 302 | 1089 | 0 |

TABLE 32b

Ratios for major formulation components.

| TG/ART 287 | PC/ART 287 | PC/TG | FC/CE |
|---|---|---|---|
| 1.19 | 10.75 | 9.05 | 0.47 |

Coarse suspension was prepared and MF processed (lot#005.14.2). Buffer: Acetate (10 mM) buffered saline pH 5.5.

TABLE 32c 287 content and stability of resultant emulsion.

| | | 287 | | Formulated 287 Stability | |
|---|---|---|---|---|---|
| Manufacturing Date | Lot# | Content, mg/ml | Recovery 1, % | Days past mfg | Content, mg/ml | Recovery 2, % |
| 6 Jun. 2013 | 005.18.1 | 2.81 | 55.4 | 26 | 2.82 | 100.4 |

Recovery 1, %—relative to amount of 287 used for formulation; Recovery 2, %—relative to 287 content determined in emulsion on the day of manufacturing.

TABLE 32d

Particle size and stability of resultant emulsion.

| | | Particle size | Formulation Stability | |
|---|---|---|---|---|
| Manufacturing Date | Lot# | by intensity, nm | Days past mfg | Particle size nm |
| 6 Jun. 2013 | 005.18.1 | 47.5 | 26 | 51.7 |

MFP In FIG. 81, particle size reached R1 at ~99 nm after 30 min of processing at ~60° C. Lowering the temperature to ~20° C. resulted in increase of the particle size to 161.7 nm. Raising the temperature to 60° C. and processing for 30 min resulted in particle size decrease to 97 nm and reaching R2 (FIG. 81). MFP was stopped and material was filtered. Decrease of particle size from 97.7 to 47.5 nm was observed after filtration (FIG. 81).

HPLC Analysis. 287 content in resultant emulsion determined by HPLC (Taxane_Prodrug.M) was 2.81 mg/ml. Data indicate that only 55.4% of the drug used for preparation of this formulation was incorporated into lipid particles (Table 32c). HPLC determined drug content of the unfiltered emulsion was 4.56 mg/ml. Data indicate that 89.9% of the drug used for preparation of this formulation was incorporated into lipid particles and suggests that substantial portion (~38%) of formulated 287 was lost during final filtration step. HPLC data are in line with notable decrease of the particle size after filtration. Data suggest particle size heterogeneity of resultant emulsion and retention of large 287 containing particles on the filter. No change of 287 content or particle size was observed in resultant emulsion after 26 days of storage at room temperature (Table 32c). Particle size analysis of 287 containing formulation. No significant particle size change observed during 26 days (FIG. 82 and Table 32c). Data indicate high stability of the resultant emulsion similar to that of ART-207 containing emulsions when the same lipid formulation was used.

Particle size analysis data are in line with HPLC data indicating: a) notable decrease of nanoparticle size and 287 content after final filtration step; and b) high stability of resultant emulsion and formulated 287. Emulsion was prepared in 10 mM Tris-HCl buffer, pH 7.4. Addition of DMPC markedly improves stability of 287-containing emulsion. A similar effect of DMPC was observed for ART-207-containing emulsions.

Composition and Ratios. Unique composition with specific ratios of formulation components that produces stable drug-free and drug-containing nanoparticles in the range from 40 to 100 nm. The optimal range of total solids calculated as Weight/Volume (W/V) percent is 6.9-7.1% (TS, %). The optimal range of total lipids calculated as Weight/Volume (W/V) percent is 6.1-6.3% (TL, %). Data indicate that lipid formulation optimized for ART-207 is suitable for generation of stable nanoparticular emulsions containing a broad variety of lipophilic structurally diverse compounds. Examples of ratios for major components are in the Table 32e.

TABLE 32e

Ratios for major formulation components.

| TG/287 | PC/287 | PC/TG | FC/CE | PC/TC | TG/TC |
|---|---|---|---|---|---|
| 0.97-1.6 | 7.5-12 | 3.5-11 | 0.3-0.6 | 17-25 | 2-7 |

For exact composition and details see Master Tables 5 and 6.

MASTER TABLE 1

Total Solids Pre-Mixes (TSPM) and corresponding resultant emulsions.

| Material | Preparation date | Lot# | Material | Processing date | Lot# |
|---|---|---|---|---|---|
| TSPM | 17 Dec. 2012 | 002.102.1 | Emulsion | 18 Dec. 2012 | 002.103.1 |
| TSPM | 17 Dec. 2012 | 002.102.2 | Emulsion | 19 Dec. 2012 | 002.104.1 |
| TSPM | 18 Dec. 2012 | 002.103.2 | Emulsion | 19 Dec. 2012 | 002.105.1 |
| TSPM | 9 Jan. 2013 | 002.107.2 | Emulsion | 9 Jan. 2013 | 002.108.1 |
| TSPM | 9 Jan. 2013 | 002.108.2 | Emulsion | 9 Jan. 2013 | 002.109.1 |
| TSPM | 10 Jan. 2013 | 002.109.2 | Emulsion | 10 Jan. 2013 | 002.110.1 |
| TSPM | 10 Jan. 2013 | 002.109.3 | Emulsion | 11 Jan. 2013 | 002.111.1 |
| TSPM | 11 Jan. 2013 | 002.110.4 | Emulsion | 11 Jan. 2013 | 002.111.2 |
| TSPM | 15 Jan. 2013 | 002.115.4 | Emulsion | 16 Jan. 2013 | 002.116.1 |
| TSPM | 15 Jan. 2013 | 002.115.1 | Emulsion | 19 Jan. 2013 | 002.118.0 |
| TSPM | 15 Jan. 2013 | 002.118.1 | Emulsion | 19 Jan. 2013 | 002.118.00 |
| TSPM | 15 Jan. 2013 | 002.115.2 | Emulsion | 20 Jan. 2013 | 002.119.4 |
| TSPM | 15 Jan. 2013 | 002.115.3 | Emulsion | 21 Jan. 2013 | 002.121.4 |
| TSPM | 15 Jan. 2013 | 002.115.3 | Emulsion | 22 Jan. 2013 | 002.122.0 |
| TSPM | 22 Jan. 2013 | 002.122.1 | Emulsion | 23 Jan. 2013 | 002.123.11 |
| TSPM | 22 Jan. 2013 | 002.122.1 | Emulsion | 23 Jan. 2013 | 002.123.12 |
| TSPM | 22 Jan. 2013 | 002.122.1 | Emulsion | 23 Jan. 2013 | 002.123.13 |

MASTER TABLE 1-continued

Total Solids Pre-Mixes (TSPM) and corresponding resultant emulsions.

| Material | Preparation date | Lot# | Material | Processing date | Lot# |
|---|---|---|---|---|---|
| TSPM | 24 Jan. 2013 | 002.125.1 | Emulsion | 25 Jan. 2013 | 002.125.21 |
| TSPM | 24 Jan. 2013 | 002.125.1 | Emulsion | 25 Jan. 2013 | 002.125.22 |
| TSPM | 8 Feb. 2013 | 002.131.1 | Emulsion | 9 Feb. 2013 | 002.131.2 |
| TSPM | 9 Feb. 2013 | 002.134.1 | Emulsion | 9 Feb. 2013 | 002.134.2 |
| TSPM | 11 Feb. 2013 | 002.135.1 | Emulsion | 12 Feb. 2013 | 002.136.21 |
| TSPM | 11 Feb. 2013 | 002.135.1 | Emulsion | 12 Feb. 2013 | 002.136.22 |
| TSPM | 11 Feb. 2013 | 002.135.1 | Emulsion | 12 Feb. 2013 | 002.136.23 |
| TSPM | 14 Feb. 2013 | 002.137.1 | Emulsion | 15 Feb. 2013 | 002.137.3 |
| TSPM | 14 Feb. 2013 | 002.137.2 | Emulsion | 15 Feb. 2013 | 002.137.41 |
| TSPM | 14 Feb. 2013 | 002.137.2 | Emulsion | 15 Feb. 2013 | 002.137.42 |
| TSPM | 14 Feb. 2013 | 002.137.2 | Emulsion | 15 Feb. 2013 | 002.137.43 |
| TSPM | 21 Feb. 2013 | 002.139.1 | Emulsion | 21 Feb. 2013 | 002.139.2 |
| TSPM | 21 Feb. 2013 | 002.140.1 | Emulsion | 21 Feb. 2013 | 002.140.21 |
| TSPM | 21 Feb. 2013 | 002.140.1 | Emulsion | 21 Feb. 2013 | 002.140.22 |
| TSPM | 21 Feb. 2013 | 002.140.1 | Emulsion | 21 Feb. 2013 | 002.140.23 |
| TSPM | 21 Feb. 2013 | 002.140.1 | Emulsion | 21 Feb. 2013 | 002.140.24 |
| TSPM | 13 Mar. 2013 | 002.150.1 | Emulsion | 14 Mar. 2013 | 002.151.5 |
| TSPM | 13 Mar. 2013 | 002.150.2 | Emulsion | 14 Mar. 2013 | 002.151.6 |
| TSPM | 13 Mar. 2013 | 002.150.3 | Emulsion | 14 Mar. 2013 | 002.151.7 |
| TSPM | 13 Mar. 2013 | 002.150.4 | Emulsion | 14 Mar. 2013 | 002.151.8 |
| TSPM | 15 Mar. 2013 | 002.152.1 | Emulsion | 15 Mar. 2013 | 002.153.1 |
| TSPM | 15 Mar. 2013 | 002.152.2 | Emulsion | 15 Mar. 2013 | 002.153.2 |
| TSPM | 21 Mar. 2013 | 002.155.1 | Emulsion | 22 Mar. 2013 | 002.156.1 |
| TSPM | 25 Mar. 2013 | 002.156.2 | Emulsion | 25 Mar. 2013 | 002.156.3 |
| TSPM | 26 Mar. 2013 | 002.158.1 | Emulsion | 27 Mar. 2013 | 002.158.2 |
| TSPM | 28 Mar. 2013 | 005.1.1 | Emulsion | 29 Mar. 2013 | 005.1.2 |
| TSPM | 29 Mar. 2013 | 005.2.1 | Emulsion | 29 Mar. 2013 | 005.2.2 |
| TSPM | 1 Apr. 2013 | 005.2.1 | Emulsion | 1 Apr. 2013 | 005.2.3 |

MASTER TABLE 2

Composition of TSPM (Total Solids Pre-Mix).

| | | | | | | | | Components Weighed, mg (per 100 ml) | | | | | TS, % W/V | TL, % W/V |
|---|---|---|---|---|---|---|---|---|---|---|---|---|---|---|
| Date | Lot# | PC | TG | FC | CE | U | VitE | ART | P188 | DMPC | PS | | | |
| 17 Dec. 2012 | 002.102.1 | 2330 | 1239 | 206 | 153 | 10 | 10 | 0 | 0 | 0 | 0 | | 3.9 | 3.9 |
| 17 Dec. 2012 | 002.102.2 | 2338 | 1247 | 203 | 152 | 10 | 10 | 0 | 0 | 0 | 0 | | 4.0 | 3.9 |
| 18 Dec. 2012 | 002.103.2 | 2176 | 1145 | 184 | 141 | 10 | 10 | 320 | 0 | 0 | 0 | | 4.0 | 3.6 |
| 9 Jan. 2013 | 002.107.2 | 4157 | 1397 | 70 | 347 | 10 | 10 | 648 | 0 | 0 | 0 | | 6.6 | 6.0 |
| 9 Jan. 2013 | 002.108.2 | 5025 | 1397 | 71 | 216 | 10 | 10 | 648 | 0 | 0 | 0 | | 7.4 | 6.7 |
| 10 Jan. 2013 | 002.109.2 | 5155 | 1390 | 70 | 213 | 10 | 10 | 648 | 0 | 0 | 0 | | 7.5 | 6.8 |
| 10 Jan. 2013 | 002.109.3 | 5170 | 1392 | 70 | 213 | 10 | 10 | 213 | 0 | 0 | 0 | | 7.1 | 6.8 |
| 11 Jan. 2013 | 002.110.4 | 5900 | 652 | 69 | 150 | 10 | 10 | 648 | 0 | 0 | 0 | | 7.4 | 6.8 |
| 15 Jan. 2013 | 002.115.4 | 5123 | 1390 | 70 | 212 | 10 | 10 | 648 | 1000 | 0 | 0 | | 8.5 | 6.8 |
| 15 Jan. 2013 | 002.115.1 | 5200 | 1390 | 70 | 213 | 10 | 10 | 0 | 0 | 0 | 0 | | 6.9 | 6.9 |
| 15 Jan. 2013 | 002.118.1 | 5209 | 1387 | 69 | 213 | 10 | 10 | 0 | 0 | 0 | 0 | | 6.9 | 6.9 |
| 15 Jan. 2013 | 002.115.2 | 5200 | 1389 | 70 | 213 | 10 | 10 | 673 | 0 | 0 | 0 | | 7.6 | 6.9 |
| 15 Jan. 2013 | 002.115.3 | 5185 | 1393 | 70 | 213 | 10 | 10 | 671 | 0 | 0 | 0 | | 7.6 | 6.9 |
| 15 Jan. 2013 | 002.115.3 | 5185 | 1393 | 70 | 213 | 10 | 10 | 671 | 250 | 0 | 0 | | 7.8 | 6.9 |
| 22 Jan. 2013 | 002.122.1 | 5085 | 501 | 70 | 148 | 10 | 10 | 500 | 256 | 0 | 0 | | 6.6 | 5.8 |
| 22 Jan. 2013 | 002.122.1 | 5085 | 501 | 70 | 148 | 10 | 10 | 500 | 256 | 0 | 0 | | 6.6 | 5.8 |
| 22 Jan. 2013 | 002.122.1 | 5085 | 501 | 70 | 148 | 10 | 10 | 500 | 256 | 0 | 0 | | 6.6 | 5.8 |
| 24 Jan. 2013 | 002.125.1 | 4085 | 511 | 70 | 150 | 10 | 10 | 503 | 250 | 1053 | 0 | | 6.6 | 5.9 |
| 24 Jan. 2013 | 002.125.1 | 4085 | 511 | 70 | 150 | 10 | 10 | 503 | 475 | 1053 | 0 | | 6.9 | 5.9 |
| 8 Feb. 2013 | 002.131.1 | 5190 | 701 | 69 | 148 | 10 | 10 | 0 | 251 | 0 | 0 | | 6.4 | 6.1 |
| 9 Feb. 2013 | 002.134.1 | 5220 | 697 | 69 | 149 | 10 | 10 | 529 | 250 | 0 | 0 | | 6.9 | 6.1 |
| 11 Feb. 2013 | 002.135.1 | 4180 | 705 | 68 | 147 | 10 | 10 | 525 | 300 | 1098 | 0 | | 7.0 | 6.2 |
| 11 Feb. 2013 | 002.135.1 | 4180 | 705 | 68 | 147 | 10 | 10 | 525 | 300 | 1098 | 0 | | 7.0 | 6.2 |
| 11 Feb. 2013 | 002.135.1 | 4180 | 705 | 68 | 147 | 10 | 10 | 525 | 300 | 1098 | 0 | | 7.0 | 6.2 |
| 14 Feb. 2013 | 002.137.1 | 5360 | 1408 | 70 | 150 | 10 | 10 | 0 | 0 | 0 | 200 | | 7.2 | 7.2 |
| 14 Feb. 2013 | 002.137.2 | 5390 | 1391 | 70 | 148 | 10 | 10 | 524 | 0 | 0 | 200 | | 7.7 | 7.2 |
| 14 Feb. 2013 | 002.137.2 | 5390 | 1391 | 70 | 148 | 10 | 10 | 524 | 0 | 0 | 200 | | 7.7 | 7.2 |
| 14 Feb. 2013 | 002.137.2 | 5390 | 1391 | 70 | 148 | 10 | 10 | 524 | 0 | 0 | 200 | | 7.7 | 7.2 |
| 21 Feb. 2013 | 002.139.1 | 4210 | 700 | 70 | 150 | 10 | 10 | 0 | 297 | 1060 | 0 | | 6.5 | 6.2 |
| 21 Feb. 2013 | 002.140.1 | 4230 | 703 | 70 | 150 | 10 | 10 | 527 | 298 | 1080 | 0 | | 7.1 | 6.2 |
| 21 Feb. 2013 | 002.140.1 | 4230 | 703 | 70 | 150 | 10 | 10 | 527 | 298 | 1080 | 0 | | 7.1 | 6.2 |
| 21 Feb. 2013 | 002.140.1 | 4230 | 703 | 70 | 150 | 10 | 10 | 527 | 298 | 1080 | 0 | | 7.1 | 6.2 |
| 21 Feb. 2013 | 002.140.1 | 4230 | 703 | 70 | 150 | 10 | 10 | 527 | 298 | 1080 | 0 | | 7.1 | 6.2 |
| 13 Mar. 2013 | 002.150.1 | 4344 | 700 | 71 | 151 | 11 | 10 | 0 | 303 | 1076 | 0 | | 6.7 | 6.3 |

MASTER TABLE 2-continued

Composition of TSPM (Total Solids Pre-Mix).

| | | Components Weighed, mg (per 100 ml) | | | | | | | | | | TS, % W/V | TL, % W/V |
|---|---|---|---|---|---|---|---|---|---|---|---|---|---|
| Date | Lot# | PC | TG | FC | CE | U | VitE | ART | P188 | DMPC | PS | | |
| 13 Mar. 2013 | 002.150.2 | 5057 | 840 | 85 | 180 | 13 | 12 | 0 | 361 | 1269 | 0 | 7.8 | 7.4 |
| 13 Mar. 2013 | 002.150.3 | 4233 | 705 | 70 | 150 | 10 | 10 | 532 | 300 | 1083 | 0 | 7.1 | 6.2 |
| 13 Mar. 2013 | 002.150.4 | 4203 | 699 | 70 | 150 | 10 | 10 | 532 | 300 | 1083 | 0 | 7.1 | 6.2 |
| 15 Mar. 2013 | 002.152.1 | 4277 | 698 | 70 | 150 | 10 | 10 | 501 | 301 | 1067 | 0 | 7.1 | 6.3 |
| 15 Mar. 2013 | 002.152.2 | 4320 | 698 | 70 | 150 | 10 | 10 | 475 | 304 | 1163 | 0 | 7.2 | 6.4 |
| 21 Mar. 2013 | 002.155.1 | 4300 | 490 | 69 | 148 | 11 | 10 | 505 | 300 | 1107 | 0 | 6.6 | 6.1 |
| 25 Mar. 2013 | 002.156.2 | 4340 | 600 | 70 | 150 | 10 | 10 | 511 | 300 | 1126 | 0 | 7.1 | 6.3 |
| 26 Mar. 2013 | 002.158.1 | 4345 | 698 | 70 | 150 | 11 | 10 | 529 | 301 | 1130 | 0 | 7.2 | 6.4 |
| 28 Mar. 2013 | 005.1.1 | 4340 | 850 | 70 | 150 | 11 | 10 | 530 | 300 | 1130 | 0 | 7.4 | 6.5 |
| 29 Mar. 2013 | 005.2.1 | 4250 | 735 | 70 | 150 | 10 | 10 | 543 | 300 | 1123 | 0 | 7.2 | 6.3 |
| 1 Apr. 2013 | 005.2.1 | 4250 | 735 | 70 | 150 | 10 | 10 | 543 | 300 | 1123 | 0 | 7.2 | 6.3 |

MASTER TABLE 3

Major components ratios. Particle size, stability and ART-207 content of resultant emulsion.

| | | Ratios of major components | | | | On the day of MFG | | | Formulation Stability | |
|---|---|---|---|---|---|---|---|---|---|---|
| MFG Date | Lot# | TG/ART-207 | PC/ART-207 | PC/TG | FC/CE | Particle size nm | ART-207 content mg/ml | ART-207 recovery, % | Days past MFG | Particle size nm |
| 18 Dec. 2012 | 002.103.1 | N/A | N/A | 1.88 | 1.35 | 63 | N/A | N/A | 36 | 79 |
| 19 Dec. 2012 | 002.104.1 | N/A | N/A | 1.87 | 1.34 | 45 | N/A | N/A | 35 | 82 |
| 19 Dec. 2012 | 002.105.1 | 3.58 | 6.80 | 1.90 | 1.30 | 82 | 3.1 | 98.1 | 35 | 196 |
| 9 Jan. 2013 | 002.108.1 | 2.16 | 6.42 | 2.98 | 0.20 | 129 | 4.8 | 74.2 | 14 | 184 |
| 9 Jan. 2013 | 002.109.1 | 2.16 | 7.75 | 3.60 | 0.33 | 74 | 5.5 | 84.9 | 33 | 169 |
| 10 Jan. 2013 | 002.110.1 | 2.15 | 7.96 | 3.71 | 0.33 | 70 | 6.1 | 94.4 | 13 | 156 |
| 11 Jan. 2013 | 002.111.1 | 6.54 | 24.27 | 3.71 | 0.33 | 47 | 1.9 | 87.3 | 24 | 66 |
| 11 Jan. 2013 | 002.111.2 | 1.01 | 9.10 | 9.05 | 0.46 | 66 | 3.9 | 59.9 | 38 | 75 |
| 16 Jan. 2013 | 002.116.1 | 2.15 | 7.91 | 3.69 | 0.33 | 62 | 6.1 | 93.7 | 4 | 146 |
| 19 Jan. 2013 | 002.118.0 | N/A | N/A | 3.74 | 0.33 | 47 | N/A | N/A | 60 | 70 |
| 19 Jan. 2013 | 002.118.00 | N/A | N/A | 3.75 | 0.33 | 47 | N/A | N/A | 60 | 79 |
| 20 Jan. 2013 | 002.119.4 | 2.07 | 7.73 | 3.74 | 0.33 | 78 | 6.9 | 100.0 | 22 | 218 |
| 21 Jan. 2013 | 002.121.4 | 2.07 | 7.72 | 3.72 | 0.33 | 110 | 6.1 | 90.2 | 0 | N/A |
| 22 Jan. 2013 | 002.122.0 | 2.07 | 7.72 | 3.72 | 0.33 | 80 | 5.6 | 83.9 | 57 | 197 |
| 23 Jan. 2013 | 002.123.11 | 1.00 | 10.17 | 10.15 | 0.47 | 68 | 3.7 | 74.2 | 56 | 73 |
| 23 Jan. 2013 | 002.123.12 | 1.00 | 10.17 | 10.15 | 0.47 | 57 | 3.7 | 74.2 | 30 | 67 |
| 23 Jan. 2013 | 002.123.13 | 1.00 | 10.17 | 10.15 | 0.47 | 69 | 3.7 | 74.2 | 56 | 70 |
| 25 Jan. 2013 | 002.125.21 | 1.02 | 10.21 | 10.05 | 0.47 | 67 | 4.0 | 79.0 | 54 | 62 |
| 25 Jan. 2013 | 002.125.22 | 1.02 | 10.21 | 10.05 | 0.47 | 66 | 4.0 | 79.0 | 54 | 64 |
| 9 Feb. 2013 | 002.131.2 | N/A | N/A | 7.40 | 0.47 | 42 | N/A | N/A | 39 | 49 |
| 9 Feb. 2013 | 002.134.2 | 1.32 | 9.87 | 7.49 | 0.46 | 76 | 4.7 | 89.0 | 39 | 84 |
| 12 Feb. 2013 | 002.136.21 | 1.34 | 10.05 | 7.49 | 0.46 | 58 | 4.3 | 81.9 | 36 | 61 |
| 12 Feb. 2013 | 002.136.22 | 1.34 | 10.05 | 7.49 | 0.46 | 42 | 4.2 | 80.4 | 36 | 55 |
| 12 Feb. 2013 | 002.136.23 | 1.34 | 10.05 | 7.49 | 0.46 | 59 | 4.5 | 85.7 | 36 | 60 |
| 15 Feb. 2013 | 002.137.3 | N/A | N/A | 3.95 | 0.47 | 49 | N/A | N/A | 33 | 51 |
| 15 Feb. 2013 | 002.137.41 | 2.65 | 10.67 | 4.02 | 0.47 | 53 | 4.8 | 91.2 | 33 | 108 |
| 15 Feb. 2013 | 002.137.42 | 2.65 | 10.67 | 4.02 | 0.47 | 84 | 5.0 | 95.4 | 33 | 134 |
| 15 Feb. 2013 | 002.137.43 | 2.65 | 10.67 | 4.02 | 0.47 | 54 | 4.9 | 93.1 | 33 | 183 |
| 21 Feb. 2013 | 002.139.2 | N/A | N/A | 7.53 | 0.47 | 38 | N/A | N/A | 27 | 43 |
| 21 Feb. 2013 | 002.140.21 | 1.33 | 10.08 | 7.55 | 0.47 | 58 | 4.4 | 84.2 | 27 | 58 |
| 21 Feb. 2013 | 002.140.22 | 1.33 | 10.08 | 7.55 | 0.47 | 46 | 4.1 | 78.1 | 27 | 54 |
| 21 Feb. 2013 | 002.140.23 | 1.33 | 10.08 | 7.55 | 0.47 | 59 | 4.5 | 85.7 | 27 | 58 |
| 21 Feb. 2013 | 002.140.24 | 1.33 | 10.08 | 7.55 | 0.47 | 49 | 4.4 | 82.9 | 27 | 55 |
| 14 Mar. 2013 | 002.151.5 | N/A | N/A | 7.74 | 0.47 | 37 | N/A | N/A | 42 | 47 |
| 14 Mar. 2013 | 002.151.6 | N/A | N/A | 7.53 | 0.47 | 38 | N/A | N/A | 42 | 43 |
| 14 Mar. 2013 | 002.151.7 | 1.33 | 9.99 | 7.54 | 0.47 | 72 | 5.3 | 99.6 | 42 | 71 |
| 14 Mar. 2013 | 002.151.8 | 1.31 | 9.94 | 7.56 | 0.47 | 62 | 5.3 | 98.9 | 42 | 67 |
| 15 Mar. 2013 | 002.153.1 | 1.39 | 10.67 | 7.66 | 0.47 | 66 | 4.7 | 93.5 | 41 | 69 |
| 15 Mar. 2013 | 002.153.2 | 1.47 | 11.54 | 7.85 | 0.47 | 53 | 4.4 | 92.2 | 53 | 64 |
| 22 Mar. 2013 | 002.156.1 | 0.97 | 10.72 | 11.03 | 0.47 | 63 | 4.1 | 80.3 | 42 | 59 |
| 25 Mar. 2013 | 002.156.3 | 1.17 | 10.70 | 9.11 | 0.47 | 62 | 4.8 | 94.0 | 43 | 61 |
| 27 Mar. 2013 | 002.158.2 | 1.32 | 10.35 | 7.84 | 0.47 | 80 | 4.7 | 89.6 | 37 | 72 |
| 29 Mar. 2013 | 005.1.2 | 1.60 | 10.32 | 6.44 | 0.47 | 74 | 4.7 | 89.5 | 35 | 78 |
| 29 Mar. 2013 | 005.2.2 | 1.35 | 9.90 | 7.31 | 0.47 | 102 | 4.9 | 89.3 | 35 | 101 |
| 1 Apr. 2013 | 005.2.3 | 1.35 | 9.90 | 7.31 | 0.47 | 92 | 4.3 | 89.3 | 26 | 95 |

Example composition and ratios for major components for formulations incorporating 287 are given in the Master Tables 4 and 5 below:

MASTER TABLE 4

Total Solids Pre-Mixes (TSPM) and corresponding resultant emulsions.

| Material | Preparation date | Lot# | Material | Processing date | Lot# |
|---|---|---|---|---|---|
| TSPM | 30 May 2013 | 005.14.1 | Emulsion | 31 May 2013 | 005.14.2 |
| TSPM | 4 Jun. 2013 | 005.16.1 | Emulsion | 4 Jun. 2013 | 005.16.2 |
| TSPM | 5 Jun. 2013 | 005.17.1 | Emulsion | 6 Jun. 2013 | 005.18.1 |

MASTER TABLE 5

Composition of TSPM (Total Solids Pre-Mix).

| | | Components Weighed, mg (per 100 ml) | | | | | | | | | | TS, % W/V | TL, % W/V |
|---|---|---|---|---|---|---|---|---|---|---|---|---|---|
| Date | Lot# | PC | TG | FC | CE | U | Vit E | ART | P188 | DMPC | PS | | |
| 30 May 2013 | 005.14.1 | 5300 | 596 | 71 | 150 | 10 | 10 | 501 | 300 | 0 | 0 | 6.9 | 6.1 |
| 4 Jun. 2013 | 005.16.1 | 5370 | 606 | 71 | 149 | 10 | 10 | 508 | 300 | 0 | 0 | 7.0 | 6.2 |
| 5 Jun. 2013 | 005.17.1 | 4360 | 602 | 71 | 150 | 10 | 10 | 507 | 302 | 1089 | 0 | 7.1 | 6.3 |

MASTER TABLE 6

Major components ratios. Particle size, stability and 287 content ot resultant emulsion.

| MFG | | Ratios of major components | | | | On the day of MFG | | | Formulation Stability | |
|---|---|---|---|---|---|---|---|---|---|---|
| | | | | | | Particle size | 287 content | 287 recovery, | Days past | Particle size |
| Date | Lot# | TG/287 | PC/287 | PC/TG | FC/CE | nm | mg/ml | % | MFG | nm |
| 30 May 2013 | 005.14.1 | 1.19 | 10.58 | 8.89 | 0.47 | 53.2 | 2.73 | 54.5 | 32 | 67.2 |
| 4 Jun. 2013 | 005.16.1 | 1.19 | 10.57 | 8.86 | 0.47 | 56.4 | 2.81 | 55.3 | 28 | 67.4 |
| 5 Jun. 2013 | 005.17.1 | 1.19 | 10.75 | 9.05 | 0.47 | 47.5 | 2.80 | 55.2 | 26 | 51.7 |

In addition to the above representative experiments and formulations of ART-207 and compounds disclosed herein, the above procedures are also performed on selected compounds disclosed in the present application, and the results are substantially consistent with the results described above.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

We claim:

1. A method for the treatment of cancer in a patient in need of such treatment comprising administering to the patient a therapeutically effective amount of the stable, synthetic low density lipoprotein (LDL) nanoparticle comprising:

a) a lipophilic anti-cancer agent of the formula 1a, 1b or formula 2a:

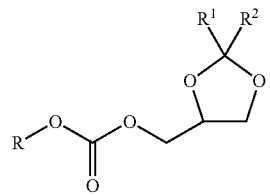

1a

-continued

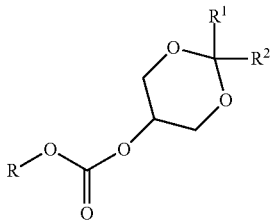

1b

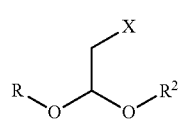

2a wherein:
for formula 1a or 1b $R^1$ is hydrogen, $C_1$-$C_4$ alkyl or $C_5$-$C_{22}$ alkyl; and $R^2$ is $C_5$-$C_{22}$ alkyl;
for formula 2a: $R^2$ is $C_1$-$C_{22}$ alkyl; and X is hydrogen or is selected from the group consisting of Cl, Br and I; and
R is a hydroxyl bearing cancer chemotherapeutic agent (HBCCA) selected from the group consisting of a taxane, abeo-taxane, camptothecin, epothilone, cucurbitacin, quassinoid, anthracycline, aclarubicin, camptothecin, masoprocol, pentostatin, amrubicin, cladribine, cytarabine, gemcitabine, elliptinium acetate, epirubicin, etoposide, formestane, fulvestrant, idarubicin, pirarubicin, topotecan, valrubicin and vinblastine;
   b) phospholipids (PL) wherein the phospholipids is selected from the group consisting of phosphotidylcholine, phosphotidylethanolamine, symmetric or asymmetric 1,2-diacyl-sn-glycero-3-phosphorylcholines, 1,2-dimyristoyl-sn-glycero-3-phosphorylcholine, 1,2-dimyristoyl-sn-glycero-3-phosphorylethanolamine, egg phospholipids, egg phosphatidyl glycerol, dipalmitoylphosphatidyl glycerol, egg lecithin, soy lecithin, lecithin (NOS) and mixtures thereof; and
   c) triglycerides (TG);
wherein the LDL nanoparticle has a mean particle size of 40-80 nm;
and where the cancer is breast cancer.

2. The method of claim 1, wherein the LDL nanoparticle has a mean size distribution of 60 nm.

3. The method of claim 1, further comprising cholesterol ester (CE) or cholesterol (C), or mixtures of cholesterol ester and cholesterol.

4. The method of claim 3, wherein the cholesterol ester is selected from the group consisting of $C_{16-22}$ esters of cholesterol and mixtures thereof; and the triglycerides is selected from the group consisting of soybean oil, triolein, glyceryl tripalmitate and mixtures thereof.

5. The method of claim 1, wherein the stable, synthetic low density lipoprotein (LDL) nanoparticle further comprises an agent selected from the group consisting of triolein, BHT, ubiquinol, ubiquinol 10, vitamin E, alpha-tocopherol, gamma-tocopherol, lycopene, retinyl derivative, betacarotene, and mixtures thereof.

6. The method of claim 1, wherein the anti-cancer agent is selected from the group consisting of a taxane, abeo-taxane, camptothecin, epothilone, cucurbitacin, quassinoid and an anthracycline.

7. The method of claim 1, wherein the anticancer agent is selected from the group consisting of aclarubicin, camptothecin, masoprocol, pentostatin, amrubicin, cladribine, cytarabine, gemcitabine, elliptinium acetate, epirubicin, etoposide, formestane, fulvestrant, idarubicin, pirarubicin, topotecan, valrubicin and vinblastine.

8. The method of claim 1, wherein the lipophilic anti-cancer agent has a logP greater than 6.0.

9. The method of claim 3, wherein the weight ratio of PL:TG:CE:C ranges from 73:12:2:1 to 78:12:2:1; optionally further comprising an additive selected from the group consisting of triolein, BHT, ubiquinol, ubiquinol 10, vitamin E, alpha-tocopherol, gamma-tocopherol, lycopene, retinyl derivative, betacarotene, and mixtures thereof.

10. The method of claim 9, wherein the weight ratio of PL:TG:CE:C is 77:10:2:1.

11. The method of claim 1, wherein the stable, synthetic low density lipoprotein (LDL) nanoparticle further comprises poloxamers that are nonionic triblock copolymers composed of a central hydrophobic chain of polyoxypropylene (poly(propylene oxide)) flanked by two hydrophilic chains of polyoxyethylene (poly(ethylene oxide)), or mixtures thereof.

\* \* \* \* \*